US012714334B2

(12) United States Patent
Chapman et al.

(10) Patent No.: US 12,714,334 B2
(45) Date of Patent: Aug. 25, 2026

(54) METHOD FOR MANUFACTURING MICRONEEDLE BIOSENSORS

(71) Applicant: One Health Biosensing Inc., New York, NY (US)

(72) Inventors: Matthew Chapman, Oakland, CA (US); Ashwin Pushpala, San Francisco, CA (US); Jeffrey Dachis, Brooklyn, NY (US)

(73) Assignee: One Health Biosensing Inc., New York, NY (US)

( * ) Notice: Subject to any disclaimer, the term of this patent is extended or adjusted under 35 U.S.C. 154(b) by 1150 days.

(21) Appl. No.: 17/578,386

(22) Filed: Jan. 18, 2022

(65) Prior Publication Data

US 2022/0225901 A1 Jul. 21, 2022

Related U.S. Application Data

(60) Provisional application No. 63/139,203, filed on Jan. 19, 2021.

(51) Int. Cl.
*G01R 31/28* (2006.01)
*A61B 5/145* (2006.01)

(52) U.S. Cl.
CPC ...... *A61B 5/14514* (2013.01); *A61B 5/14532* (2013.01); *A61B 5/14546* (2013.01);
(Continued)

(58) Field of Classification Search
CPC ............ A61B 5/14514; A61B 5/14532; A61B 5/14546; A61B 5/1495; A61B 2562/046;
(Continued)

(56) References Cited

U.S. PATENT DOCUMENTS 4,953,552 A 9/1990 DeMarzo
5,215,088 A 6/1993 Normann et al.
(Continued)

FOREIGN PATENT DOCUMENTS

CN 1735375 2/2006
CN 102469941 5/2012
(Continued)

OTHER PUBLICATIONS

European Patent Office, International Search Report and Written Opinion, counterpart PCT Application No. PCT/US2022/012825, Filed: Jan. 18, 2022, Applicant: Informed Data Systems Inc. d/b/a One Drop, Mailed: Jun. 28, 2022, 19 pages.
(Continued)

*Primary Examiner* — Paul D Kim
(74) *Attorney, Agent, or Firm* — Ashurst Perkins Coie US LLP

(57) ABSTRACT

Systems and methods for manufacturing biosensors are disclosed herein. The biosensors can be used for personal biomonitoring and providing personalized healthcare assessments. The manufacturing method can include gathering production data throughout production of the biosensors and using the production data to track performance of one or more components and predict performance metrics for each biosensor. The manufacturing method can include mapping locations along a wafer and measuring wafer components. The predicted performance metrics can then be used by a biomonitoring system to adjust operating parameters of the biosensor before a user relies on the healthcare assessments from the biomonitoring system.

21 Claims, 17 Drawing Sheets

(52) U.S. Cl.
CPC ................ *A61B 2560/0223* (2013.01); *A61B 2560/0266* (2013.01); *A61B 2562/046* (2013.01); *A61B 2562/12* (2013.01)

(58) Field of Classification Search
CPC ........ A61B 2562/12; A61B 2560/0223; A61B 2560/0266
See application file for complete search history.

(56) References Cited

U.S. PATENT DOCUMENTS 5,863,833 A 1/1999 Shin
5,949,739 A 9/1999 Reese
6,001,067 A 12/1999 Shults et al.
6,091,975 A 7/2000 Daddona et al.
6,275,717 B1 8/2001 Gross et al.
6,424,847 B1 7/2002 Mastrototaro et al.
6,451,240 B1 9/2002 Sherman et al.
6,501,976 B1 12/2002 Sohrab
6,560,471 B1 5/2003 Heller et al.
6,582,573 B2 6/2003 Douglas et al.
6,619,093 B2 9/2003 Dawson et al.
6,690,959 B2 2/2004 Thompson
6,699,667 B2 3/2004 Keen
6,743,211 B1 6/2004 Prausnitz et al.
6,749,792 B2 6/2004 Olson
6,790,179 B2 9/2004 Skover
6,793,632 B2 9/2004 Sohrab
6,837,988 B2 1/2005 Leong et al.
6,863,833 B1 3/2005 Bloom et al.
6,875,613 B2 4/2005 Shartle et al.
6,923,764 B2 8/2005 Aceti et al.
6,931,277 B1 8/2005 Yuzhakov et al.
7,029,444 B2 4/2006 Shin et al.
7,295,867 B2 11/2007 Berner et al.
7,322,960 B2 1/2008 Yamamoto et al.
7,361,307 B2 4/2008 Shartle et al.
7,399,585 B2 7/2008 Gau
7,585,278 B2 9/2009 Aceti et al.
7,591,801 B2 9/2009 Brauker et al.
7,732,002 B2 6/2010 Kodas et al.
7,753,888 B2 7/2010 Mukerjee et al.
7,783,442 B2 8/2010 Mueller et al.
7,885,697 B2 2/2011 Brister et al.
7,920,906 B2 4/2011 Goode et al.
7,946,984 B2 5/2011 Brister et al.
7,949,382 B2 5/2011 Jina
7,951,300 B2 5/2011 Bhandari et al.
8,080,385 B2 12/2011 Heller et al.
8,114,269 B2 2/2012 Cooper et al.
8,224,414 B2 7/2012 Kellogg et al.
8,280,475 B2 10/2012 Brister et al.
8,280,476 B2 10/2012 Jina
8,290,559 B2 10/2012 Shariati et al.
8,361,037 B2 1/2013 Gonnelli
8,386,027 B2 2/2013 Chuang et al.
8,478,557 B2 7/2013 Hayter et al.
8,565,849 B2 10/2013 Kamath et al.
8,604,810 B2 12/2013 Sheppard
8,608,924 B2 12/2013 Cooper et al.
8,615,282 B2 12/2013 Brister et al.
8,641,672 B2 2/2014 Yodfat et al.
8,663,106 B2 3/2014 Stivoric et al.
8,668,645 B2 3/2014 Drucker et al.
8,677,188 B2 3/2014 Eickmeyer et al.
8,700,114 B2 4/2014 Gottlieb et al.
8,718,742 B2 5/2014 Beck et al.
8,734,348 B2 5/2014 Say et al.
8,744,545 B2 6/2014 Say et al.
8,744,547 B2 6/2014 Budiman et al.
8,774,887 B2 7/2014 Say et al.
8,792,953 B2 7/2014 Brister et al.
8,808,532 B2 8/2014 Yang et al.
8,858,912 B2 10/2014 Boyden et al.
8,865,288 B2 10/2014 Bhandari et al.
8,882,670 B2 11/2014 Hancock
8,886,279 B2 11/2014 Tathireddy et al.
8,965,477 B2 2/2015 Hoss et al.
9,008,745 B2 4/2015 Pushpala et al.
9,011,332 B2 4/2015 Heller et al.
9,044,199 B2 6/2015 Brister et al.
9,055,901 B2 6/2015 Brister et al.
9,182,368 B2 11/2015 Pushpala et al.
9,192,328 B2 11/2015 Brauker et al.
9,195,799 B2 11/2015 Sze et al.
9,215,995 B2 12/2015 Gottlieb et al.
9,220,483 B2 12/2015 Frankhouser et al.
9,278,174 B2 3/2016 Gray
9,357,951 B2 6/2016 Simpson et al.
9,387,000 B2 7/2016 Corrie et al.
9,402,544 B2 8/2016 Yee et al.
9,414,777 B2 8/2016 Brister et al.
9,424,532 B1 8/2016 Abedini et al.
9,474,478 B2 10/2016 Bhavaraju et al.
9,498,159 B2 11/2016 Heller et al.
9,504,411 B2 11/2016 Engelhardt et al.
9,532,741 B2 1/2017 Brauker et al.
9,603,557 B2 3/2017 Brister et al.
9,615,851 B2 4/2017 Neinast et al.
9,632,060 B2 4/2017 Shah et al.
9,662,047 B2 5/2017 Barman et al.
9,675,790 B2 6/2017 Stoeber et al.
9,737,247 B2 8/2017 Wang et al.
9,743,870 B2 8/2017 Wang et al.
9,814,389 B2 11/2017 DeHennis
9,945,807 B2 * 4/2018 Baghbani-Parizi .... H10D 86/01
9,974,471 B1 5/2018 Kam et al.
10,046,114 B1 8/2018 Biederman et al.
10,070,820 B2 9/2018 Huang
10,136,846 B2 11/2018 Wang et al.
10,173,042 B2 1/2019 Pushpala et al.
10,238,289 B2 3/2019 Hagi
10,321,858 B2 6/2019 Maiz-Aguinaga et al.
10,327,678 B2 6/2019 Gottlieb et al.
10,383,558 B2 8/2019 Cho et al.
10,466,194 B2 * 11/2019 deSa ................ G01N 33/5438
10,524,730 B2 1/2020 Reitz et al.
10,549,080 B2 2/2020 Pushpala et al.
10,595,754 B2 3/2020 Pushpala et al.
10,667,733 B2 6/2020 Simpson et al.
10,765,369 B2 9/2020 Antonio et al.
10,799,158 B2 10/2020 Brister et al.
10,799,159 B2 10/2020 Brister et al.
10,806,384 B2 10/2020 Frey et al.
10,813,577 B2 10/2020 Brister et al.
10,820,860 B2 11/2020 Pushpala et al.
10,827,954 B2 11/2020 Hoss et al.
10,835,161 B2 11/2020 Simpson et al.
10,874,335 B2 12/2020 Cho et al.
11,123,532 B2 9/2021 Pushpala et al.
11,197,985 B2 12/2021 Pushpala et al.
11,684,298 B2 * 6/2023 Tehrani ............. A61B 5/14865 600/345
2002/0015963 A1 2/2002 Keen
2002/0062202 A1 5/2002 Arai
2002/0123048 A1 9/2002 Gau
2003/0100821 A1 5/2003 Heller et al.
2004/0060902 A1 4/2004 Evans et al.
2004/0260241 A1 12/2004 Yamamoto et al.
2005/0004438 A1 1/2005 Ward et al.
2005/0245839 A1 11/2005 Stivoric et al.
2006/0015058 A1 1/2006 Kellogg et al.
2006/0016700 A1 1/2006 Brister et al.
2006/0258929 A1 11/2006 Goode et al.
2006/0264716 A1 11/2006 Zander
2007/0032717 A1 2/2007 Brister et al.
2007/0179371 A1 8/2007 Peyser et al.
2007/0208245 A1 9/2007 Brauker et al.
2007/0219480 A1 9/2007 Kamen et al.
2008/0033254 A1 2/2008 Kamath et al.
2008/0058726 A1 3/2008 Jina et al.
2008/0138582 A1 6/2008 Bhandari et al.
2008/0154107 A1 6/2008 Jina
2008/0319285 A1 12/2008 Hancock

(56) References Cited

U.S. PATENT DOCUMENTS

2008/0319298 A1 12/2008 Huys et al.
2009/0036794 A1 2/2009 Stubhaug et al.
2009/0099502 A1 4/2009 Tokumoto et al.
2009/0156924 A1 6/2009 Shariati et al.
2009/0177068 A1 7/2009 Stivoric et al.
2009/0259118 A1 10/2009 Feldman et al.
2009/0294307 A1 12/2009 Liu et al.
2009/0301994 A1 12/2009 Bhandari et al.
2009/0321277 A1 12/2009 Heller et al.
2010/0010601 A1 1/2010 Negi et al.
2010/0016687 A1 1/2010 Brauker et al.
2010/0030045 A1 2/2010 Gottlieb et al.
2010/0075353 A1 3/2010 Heaton
2010/0112195 A1 5/2010 Kodas et al.
2010/0113897 A1 5/2010 Brenneman et al.
2010/0152651 A1 6/2010 Boyden et al.
2010/0298895 A1 11/2010 Ghaffari et al.
2010/0324392 A1 12/2010 Yee et al.
2011/0009824 A1 1/2011 Yodfat et al.
2011/0029269 A1 2/2011 Hayter et al.
2011/0053121 A1 3/2011 Heaton
2011/0089957 A1 4/2011 Sheppard
2011/0125058 A1 5/2011 Levinson et al.
2011/0237917 A1 9/2011 Roy et al.
2011/0237925 A1 9/2011 Yue et al.
2011/0257456 A1 10/2011 Kinn et al.
2011/0257495 A1 10/2011 Hoss et al.
2011/0319734 A1 12/2011 Gottlieb et al.
2012/0035442 A1 2/2012 Barman et al.
2012/0046533 A1 2/2012 Voskanyan et al.
2012/0078071 A1 3/2012 Bohm et al.
2012/0108931 A1 5/2012 Taub et al.
2012/0165639 A1 6/2012 Engelhardt et al.
2012/0190950 A1 7/2012 Yang et al.
2012/0190952 A1 7/2012 Stafford
2012/0203078 A1 8/2012 Sze et al.
2012/0209244 A1 8/2012 Gray
2012/0209303 A1 8/2012 Frankhouser et al.
2012/0215087 A1 8/2012 Cobelli et al.
2012/0238841 A1 9/2012 Castle et al.
2012/0265042 A1 10/2012 Neinast et al.
2013/0130215 A1 5/2013 Bock et al.
2013/0178726 A1 7/2013 Wang et al.
2013/0190583 A1 7/2013 Grosman et al.
2013/0225956 A1 8/2013 Huang et al.
2013/0230913 A1 9/2013 Florescu
2013/0248364 A1 9/2013 Kahn et al.
2013/0267811 A1 10/2013 Pryor et al.
2013/0310665 A1 11/2013 Crean et al.
2013/0328578 A1 12/2013 Shah et al.
2013/0331676 A1 12/2013 Morgan et al.
2013/0338598 A1 12/2013 Gyrn
2014/0012510 A1 1/2014 Mensinger et al.
2014/0066735 A1 3/2014 Engelhardt et al.
2014/0073892 A1 3/2014 Randloev et al.
2014/0275897 A1 9/2014 Pushpala et al.
2014/0336487 A1 11/2014 Wang
2015/0150505 A1 6/2015 Kaskoun et al.
2015/0347707 A1 12/2015 Albisser et al.
2016/0038180 A1 2/2016 Kube et al.
2016/0113556 A1 4/2016 Simpson et al.
2016/0157764 A1 6/2016 Di Palma et al.
2016/0278672 A1 9/2016 Choo et al.
2017/0095187 A1 4/2017 Svoboda et al.
2017/0128009 A1 5/2017 Pushpala et al.
2017/0172475 A1 6/2017 Pushpala et al.
2017/0188898 A1 7/2017 Jina et al.
2018/0140235 A1 5/2018 Pushpala et al.
2018/0279929 A1 10/2018 Huang et al.
2018/0340902 A1 11/2018 Fouroghalzaman
2018/0368771 A1 12/2018 Gray et al.
2019/0013425 A1 1/2019 Huang
2019/0053759 A1 2/2019 Cho et al.
2019/0076601 A1 3/2019 Newberry et al.
2019/0117135 A1 4/2019 Wieder
2019/0125223 A1 5/2019 Wang et al.
2019/0209057 A1 7/2019 Simpson et al.
2019/0350500 A1 11/2019 Ebejer et al.
2019/0357830 A1 11/2019 Visweswara et al.
2020/0015718 A1 1/2020 Maiz-Aguinaga et al.
2020/0121902 A1 4/2020 Pushpala et al.
2020/0178853 A1 6/2020 Pushpala et al.
2020/0390395 A1 12/2020 Pushpala et al.
2020/0405234 A1 12/2020 Pushpala et al.
2021/0100504 A1 4/2021 Pushpala et al.
2021/0100505 A1 4/2021 Pushpala et al.
2022/0192551 A1* 6/2022 LaBelle ............. A61B 5/14546
2023/0255527 A1* 8/2023 Chapman ............... G16H 10/60

FOREIGN PATENT DOCUMENTS

CN 103458810 12/2013
EP 1266608 8/2006
EP 2327362 6/2011
JP 4112499 7/2008
JP 4373604 11/2009
JP 4439733 3/2010
JP 4574847 11/2010
JP 4905906 3/2012
JP 5021115 9/2012
JP 2013502978 1/2013
JP 5591715 9/2014
JP 5640110 12/2014
JP 2015505251 2/2015
JP 5680960 3/2015
JP 5749751 7/2015
JP 5795584 10/2015
JP 2016508763 3/2016
JP 2016518881 6/2016
JP 2016517601 4/2017
WO 1994020602 9/1994
WO 1999019507 4/1999
WO 1999045375 9/1999
WO 1999045387 9/1999
WO 1999056613 11/1999
WO 1999058709 11/1999
WO 2000074763 12/2000
WO 2002058537 8/2002
WO 2002062202 8/2002
WO 2002097414 12/2002
WO 2003085372 10/2003
WO 2008028087 3/2008
WO 2008157820 12/2008
WO 2009082699 7/2009
WO 2009105145 8/2009
WO 2011025549 3/2011
WO 2013058879 4/2013
WO 2013070794 5/2013
WO 2013163035 10/2013
WO 2014106263 7/2014
WO 2014145001 9/2014
WO 2014145049 9/2014

OTHER PUBLICATIONS

Lopez Subrebost et al., Silicon-based microdialysis chip with integrated fraction collection and biofouling control, Oct. 1, 2055, ISBN: 978-0-542-56242-6, Retrieved from the Internet: https://www.ri.cmu.edu/pub_files/pub4/subrebost_george_lopez_2005_1/subrebost_george_lopez_2005_1.pdf.

Yang et al., "Microfabricated glucose biosensorwith glucose oxidase entrapped in sol-gel matrix," Talanta, Elsevier, Amsterdam, NL, vol. 47, No. 3, Nov. 1, 1998, pp. 735-743, XP002468331, ISSN: 0039-9140, DOI: 10.1016/S0039-9140(98)00119-2.

Adhikari, Basudam, et al., "Polymers in sensor applications", Prog. Polym. Sci. vol. 29, pp. 699-766, Jan. 1, 2004.

Agarwal et al., "Machine Learning to Predict Hypoglycemic Events from Continuous Glucose Monitoring Data," American Diabetes Association, Diabetes, Jun. 2019, 68 (Supplement 1), 6 pages.

Aliberti et al., "A Multi-Patient Data-Driven Approach to Blood Glucose Prediction," IEEE Explore, vol. 7, May 27, 2019, pp. 69311-69325.

(56) References Cited

OTHER PUBLICATIONS

AliveCor "AliveCor" retrieved from the internet at https://www.alivecor.com on Jun. 29, 2021, 10 pages.
Apple, "Apple Watch: Helping your patients identify early warning signs" retrieved from the internet at https://www.apple.com/healthcare/apple-watch/ on Jun. 29, 2021, 9 pages.
Baron et al. "Investigations of development process of high hollow beveled microneedles using a combination of ICP RIE and dicing saw," Microsys. Technol., 2008, vol. 14, pp. 1475-1480.
Battelino, T. et al. Clinical Targets for Continuous Glucose Monitoring Data Interpretation: Recomendations From the International Consensus on Time in Range, Diabetes Care Jun. 2019, 11 pages.
Bhandari et al. "Wafer-scale fabrication of penetrating neural microelectrode arrays." Biomed Microdevices, 2010, vol. 12, pp. 797-807.
Caffrey M. COVID-19 is Changing the A1C vs Time-in-Range Debate, Expert Says. American Journal of Managed Care website, Jun. 15, 2020, Accessed Oct. 8, 2020, https://www.ajmo.com/view/covid19-is-changing-the-a1c-ys-timeinrange-debate-expert-says, 8 pages.
Chen et al. "Xgboost: A scalable tree boosting system," in Proceedings of the 22nd acm sigkdd international conference on knowledge discovery and data mining (ACM, 2016), 13 pages.
Clark et al., "Evaluating Clinical Accuracy of Systems for Self-Monitoring of Blood Glucose," American Diabetes Association, Diabetes Care, Sep.-Oct. 1987, 10(5), pp. 622-628.
Fiorini et al. "Data-driven strategies for robust forecast of continuous glucose monitoring time-series", IEEE 2017, pp. 1680-1683.
Friedman, J. "Greedy Function Approximation: A Gradient Boosting Machine" IMS 1999 Reitz Lecture, Feb. 24, 1999, 39 pages.
GitHub, "The Gluon API Specification" 2017. Retrieved from https://github.com/gluon-api/gluon-api/ Jan. 25, 2021, 5 pages.
Goldner, D.R. "A Machine-Learning Model Accurately Predicts Projected Blood Glucose" Diabetes 2018, 67 (Supplement 1), 3 pages.
Hayeri, "Predicting Future Glucose Fluctuations Using Machine Learning and Wearable Sensor Data," Diabetes, Jul. 2018, 67 (Supplement 1):738-P, 5 pages.
ISA: United States Patent and Trademark Office, International Search Report and Written Opinion, International Patent Application No. PCT/US2014/027655, Mail Date: Sep. 5, 2014, 10 pages.
ISA: United States Patent and Trademark Office, International Search Report and Written Opinion, International Patent Application No. PCT/US2015/020586, Mail Date: Jun. 24, 2015, 9 pages.
ISA: European Patent Office, International Search Report and Written Opinion for PCT Application No. PCT/US2019/049270, Mail Date: Dec. 12, 2019, 10 pages.
ISA: European Patent Office, International Search Report and Written Opinion for PCT Application No. PCT/US2020/035330, Mail Date: Aug. 20, 2020, 15 pages.
ISA: European Patent Office, International Search Report and Written Opinion for PCT Application No. PCT/US2021/016624, Mail Date: May 18, 2021, 14 pages.
ISA: European Patent Office, International Search Report and Written Opinion for PCT Application No. PCT/US21/28445, Mai Date: Nov. 24, 2021, 26 pages.
JCHR, "A Randomized Clinical Trial to Assess the Efficacy and Safety of Real-Time Continuous Glucose Monitoring in the Management of Type 1 Diabetes in Young Children (4 to <10 Year Olds)" 2011, retrieved from https://public.jaeb.org/direcnet/stdy/162, Jan. 25, 2021, 4 pages.
Li, et al. "Smartphone-based personalized blood glucose prediction" ICT Express 2 (2016), pp. 150-154.
Lundberg et al. "A Unified Approach to Interpreting Model Predictions" 31st Conference on Neural Information Processing Systems, 2017, 10 pages.
Mhaskar et al. "A Deep Learning Approach to Diabetic Blood Glucose Prediction" Frontiers in Applied Mathematics and Statistics, 3(14), 2017, 11 pages.
Pappada et al. "Neural Network-Based Real-Time Prediction of Glucose in Patients with Insulin-Dependent Diabetes" Diabetis Technology & Therapeutics, 13(2), 2011, 9 pages.
Stahl et al. "Ensemble Glucose Prediction in Insulin-Dependent Diabetes" Advancements of Medical Electronics, 2014, pp. 37-71.
Verily, "Verily Patch: Measuring body temperature through a novel adhesive patch and connected mobile app" Retrieved from the internet at https://verily.com/solutions/verily-patch/ on Jun. 29, 2021, 9 pages.
Wexler et al., "One- to Six-Month Forecasts of Time-in-Range," One Drop Poster, 2020, 1 page.
Wexler et al., "Hypo- and Hyperglycemiarediction from Pooled Continuous Glucose Monitor Data," One Drop Poster, 2020, 1 page.
Wexler Y, et al. 38-LB—One- to Six-Month Outcomes Forecasts for Diabetes and Related Conditions. American Diabetes Association 80th Scientific Sessions. Jun. 12-16, 2020, Accessed: Oct. 12, 2020, https://plan.core-apps.com/tristar_ada20/abstract/7b031725-d051-4ca7-8b00-084c4824bbd6.
Wexler, "Blood Glucose Prediction from Pooled Continuous Glucose Monitor Data," Journal of Diabetes Science and Technology, 2019 DTM Abstracts, In press: Mar. 1, 2020, A121, 6 pages.

* cited by examiner

METHOD FOR MANUFACTURING MICRONEEDLE BIOSENSORS

CROSS-REFERENCE TO RELATED APPLICATION

The present application claims the benefit of U.S. Provisional Patent Application No. 63/139,203, filed Jan. 19, 2021, the entirety of which is incorporated herein by reference.

TECHNICAL FIELD

This disclosure relates generally to personalized healthcare and, in particular, to systems and methods for tracking, monitoring, and calibrating biosensors for use in biomonitoring and healthcare guidance.

BACKGROUND

Many individuals suffer from chronic health conditions, such as diabetes, pre-diabetes, hypertension, hyperlipidemia, and the like. For example, diabetes mellitus (DM) is a group of metabolic disorders characterized by high blood glucose levels over a prolonged period. Typical symptoms of such conditions include frequent urination, increased thirst, increased hunger, etc. If left untreated, diabetes can cause many complications. There are three main types of diabetes: Type 1 diabetes, Type 2 diabetes, and gestational diabetes. Type 1 diabetes results from the pancreas' failure to produce enough insulin. In Type 2 diabetes, cells fail to respond to insulin properly. Gestational diabetes occurs when pregnant women without a previous history of diabetes develop high blood glucose levels.

Diabetes affects a significant percentage of the world's population. Timely and proper diagnoses and treatment are essential to maintaining a relatively healthy lifestyle for individuals with diabetes. Application of treatment typically relies on accurate determination of glucose concentration in the blood of an individual at a present time and/or in the future. However, conventional blood glucose monitoring systems may be unable to provide real-time analytics, personalized analytics, or blood glucose concentration forecasting, or may not provide such information in a rapid, reliable, and accurate manner. Thus, there is a need for improved systems and methods for biomonitoring and/or providing personalized healthcare recommendations or information for the treatment of diabetes and other chronic conditions.

DETAILED DESCRIPTION

I. Overview

Figure 1:
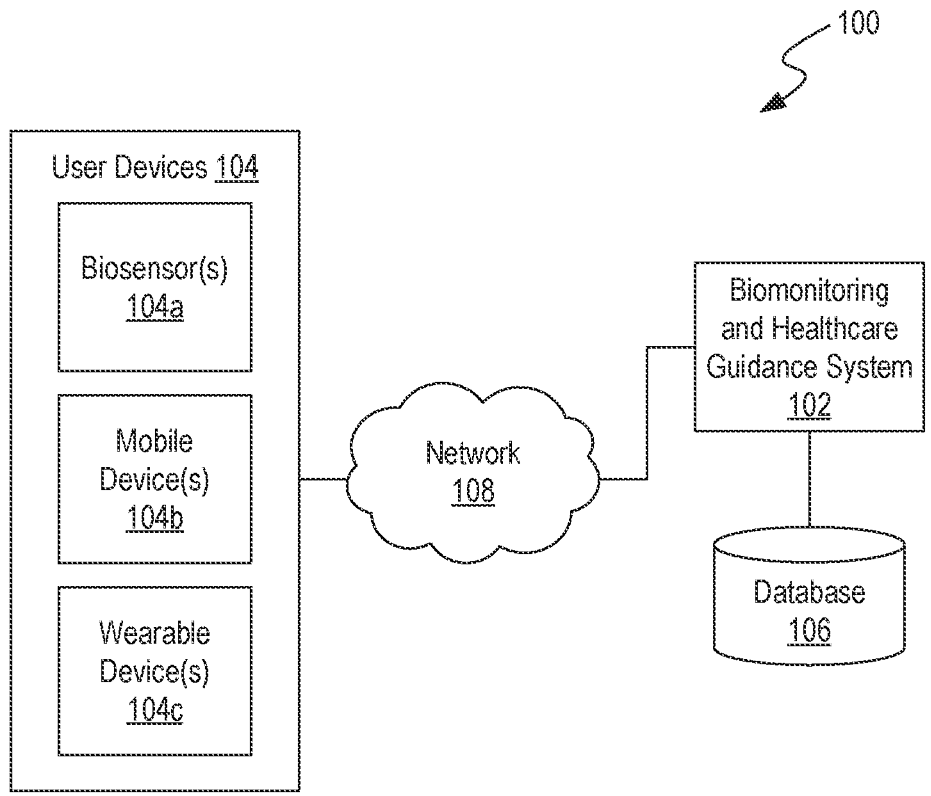
FIG. 1 is a schematic diagram of an exemplary computing environment in which a biomonitoring and healthcare guidance system operates in accordance with some embodiments of the present technology.

Biomonitoring and healthcare guidance systems are configured to generate personalized self-care recommendations (e.g., recommendations relating to sleep, exercise, diet, etc.) to guide a patient in effectively managing and/or improving a chronic condition (e.g., diabetes, pre-diabetes, hypertension, hyperlipidemia, etc.). An individual system can continuously or periodically update and/or adapt the self-care recommendations, e.g., based on data from the particular patient, data from a plurality of other patients, and the data generated during manufacturing. The system can then guide individuals toward self-care changes that are likely to improve their chronic health conditions, support them in making those changes, and adapt and/or update continuously over time.

The present technology generally relates to systems and methods for improving personal biomonitoring and providing personalized healthcare. For example, aspects of the present technology can increase the accuracy of measurements made by biosensors that are used to monitor personal health and/or make personalized healthcare decisions. In another example, aspects of the present technology can reduce the price of individual biosensors by increasing manufacturing throughput.

In some embodiments, methods for manufacturing a one or more components of a biosensor (or the biosensor in whole) include numerous points of data gathering and analyses to generate highly individualized calibration adjustments for the operation of the biosensor and/or interpretation of measurements made by the biosensor. For example, the components of a biosensor (e.g., electrode sensors, microneedle arrays for electrode sensors, disposable electronics, reusable electronics, and the like) can be manufactured in bulk, such as in a batch-wafer process. In such embodiments, the method can include generating a map of the wafer with a plurality of locations that each correspond to one or more components. Each of the locations can be associated with a unique identifier (e.g., an alpha-numeric serial number, location number/symbol, code, etc.) that allows data specific to one or more components in the location to be linked to the one or more components. For example, after a stage of manufacturing (e.g., after a deposition process to deposit a conductive layer, chemical-sensing layer, and/or an insulation layer; an etching or other removal process to remove sections of a layer and/or to isolate structures; a cutting process; and the like), the method can include generating production data related to the development of the component(s) in one or more of the locations (sometimes referred to herein as "selected locations" and/or "sampled locations"). The production data can include sensor and/or wafer-level measurements of the development of the component(s), metrics related to the manufacturing history for the wafer, in-line metrics from the manufacturing equipment, and/or any other suitable information.

In some embodiments with sensor-level measurements, the method directly measures only a subset of the locations on the wafer. Said another way, the sampled locations can include only a subset of the locations on the wafer. The method can then include extrapolating from the production data in the sampled locations to generate production data for a portion of (or all) of the other locations on the wafer. In some embodiments, the sampled locations are selected based on their relative position on the wafer and the extrapolation depends on the relative positions of the remaining locations. Purely by way of example, the sampled locations can include a first location in a peripheral region of the wafer and a second location in a central region of the wafer. The method can include extrapolating to a third location also in the central region of the wafer. In this example, the extrapolation can weight the production data for the second location above the production data for the first location since the third location is expected to have development more similar to the second location. Additionally, or alternatively, the method can include extrapolating to a fourth location in the peripheral region of the wafer. In this example, the extrapolation can weight the production data for the first location above the production data for the second location since the fourth location is expected to have development more similar to the first location. Once generated, the production data can be linked to the components in each of the locations using the unique identifiers (e.g., stored in a database using the unique identifiers as a reference number) and used in later processes. Because the production data can be updated with numerous measurements and is individualized to each of the locations, the production data can provide an accurate, granular reference to understand the development of each of the components throughout and/or after manufacturing.

Additionally, or alternatively, the production data can be used to predict the performance of the component(s) (e.g., an electro-chemical response of microneedles to one or more analytes of interest) and/or generate one or more calibration adjustments (e.g., changes to operational parameters for the biosensor with the components installed (e.g., an input bias), component-specific calibration routines before (or during) operation of the biosensor, and/or signal filters) based on the expected response of the microneedles to the analyte(s) of interest. The predicted performance and/or calibration adjustments can then be linked to the one or more components in the sampled locations using the unique identifier. In a specific, non-limiting example, the production data can include an optical measurement of an array of microneedles that indicates the array is missing a microneedle (e.g., that broke off during manufacturing). The missing microneedle can result in slightly weaker signals being generated in response to the analyte(s) of interest than a complete array. Accordingly, the production data can be used to generate a signal filter that amplifies the signals to account for the missing microneedle.

In some embodiments, the method includes extrapolating from the sampled locations to generate calibration adjustments for a portion of (or all) of the other locations on the wafer in a similar manner to the extrapolations discussed above. Because the calibration adjustments are generated at an individual sensor level (or wafer-level), the adjustments can account for minute differences during manufacturing and improve the overall accuracy of a biosensor using the components. Purely by way of example, the calibration adjustments can increase the response accuracy of a microsensor patch resulting from the method and/or the accuracy of determinations made using signals generated by the microsensor patch.

Additionally, or alternatively, the production data can be used to generate adjustments to the manufacturing process (e.g., additional, fewer, or altered deposition processes to correct and/or alter the development of the microneedles). For example, the production data can indicate that an electrode (or microneedles in the electrode) are more active than expected (e.g., when a deposition layer is thicker than expected). In this example, the adjustments to the manufacturing process can include shortening further deposition processes to reduce (or avoid) over-deposition. In another example, the production data can indicate that an electrode (or microneedles in the electrode) are less active than required (e.g., when a deposition layer is less conductive than required). In this example, the adjustments to the manufacturing process can include redoing a deposition process and/or lengthening further deposition processes. Relatedly, the production data can be used to generate adjustments to later manufacturing processes on the manufacturing equipment. For example, the production data can indicate that a manufacturing apparatus is consistently over (or under) depositing material, and future processes can be adjusted to account for the over (or under) deposition.

Additionally, or alternatively, the production data can be used to monitor the health of manufacturing equipment. For example, the production data can be used to analyze and/or track a tool health (e.g., by tracking the usage of equipment (e.g., tracking the 'milage' of the equipment) and any errors in manufacturing), adjust manufacturing stages as equipment ages, predict when maintenance may be needed, plan around expected maintenance, and the like.

In some embodiments, the wafer can be substituted for another substrate and/or carrier to complete manufacturing in bulk. Purely by way of example, individual components can be manufactured in wells on a carrier, such that they do not require singulation after manufacturing is complete. In some embodiments, the components are manufactured only partially in a bulk wafer process. Purely by way of example, the manufacturing process can include partially (or fully) forming a plurality of microneedles in a bulk wafer process, dicing the wafer into arrays of one or more microneedles, and placing the diced arrays to complete manufacturing (e.g., to form remaining components of an electrode, form bond sites, form redistribution layers, and the like). In some embodiments, the components are manufactured entirely individually. Purely by way of example, a microsensor patch comprised of one or more electrode sensors can be manufactured in an individual well process rather than on a wafer. In each of the alternatives discussed above, the method can still include assigning a unique identifier to each of the components, generating production data after one or more stages of manufacturing, linking the production data to the components using the unique identifier, generating calibration adjustments for each of the components, and/or linking the calibration adjustments to the components using the unique identifier.

In some embodiments, the production data and/or the calibration adjustments are stored in a user-accessible database and the unique identifier is stored on the components for a user to receive when they use a biosensor with the component. Purely by way of example, as discussed above, an exemplary biosensor can employ disposable microsensor patches with microneedles that access the interstitial fluid of a user's skin to detect one or more analytes of interest. Each microsensor patch can represent a component from the wafer and be associated with a unique identifier. In some embodiments, the unique identifier is communicated through a physical label (e.g., listing of the alpha-numeric code, a scannable feature such as a QR code and/or bar code, and the like) on the microsensor patch packaging and/or the microsensor patch itself. In some embodiments, the microsensor patch includes a memory storing the unique identifier and communicates the unique identifier to the biosensor and/or a user device when installed. Purely by way of example, the biosensor can read from the memory (e.g., via wired or wireless communication) and relay the unique identifier to a user device (e.g., a smartphone) whenever a microsensor patch is installed. The user (e.g., via the biosensor and/or their smartphone) can then retrieve the production data and/or the calibration adjustments from the user-accessible database. The user can then update operation of the biosensor and/or interpretation of the signals based on the retrieved production data and/or the calibration adjustments. In some embodiments, the biosensor can directly retrieve the production data and/or the calibration adjustments from the user-accessible database.

In some embodiments, the retrieval process is automatically executed between a biosensor and a networked device each time a microsensor patch is installed. In some embodiments, the user prompts the biosensor and networked device to execute the retrieval process. In some embodiments, each microsensor patch (or other component) includes a memory storing the production data and/or the calibration adjustments in addition to the unique identifier. For example, a final step in the manufacturing process can include writing production data and/or the calibration adjustments directly into the memory based on a unique identifier, allowing each microsensor patch (or other component) to be installed and accurately without requiring access to an external database.

The unique identifiers can also (or alternatively) be used to provide updates for each of the components after they are deployed. For example, when an error in manufacturing and/or the performance of a deployed component is detected, a recall order can be linked to any related component using the unique identifier. In a specific, non-limiting example, after a user installs a microsensor patch into a biosensor the user can indicate an error to the user-accessible database. The user-accessible database can then take corrective actions for related microsensor patches using the unique identifiers (e.g., using the unique identifier to identifier the relevant wafer, region of the wafer, and/or one or more related microsensor patches). In various embodiments, the corrective actions can include one or more updates to calibration adjustments, one or more warnings to a user of the related microsensor patches, and/or a recall for malfunctioning microsensor patches. In some embodiments involving a recall, the corrective action can include preventing any biosensor from operating with a recalled microsensor patch. The prevention can reduce the likelihood that a user employs a microsensor patch that may provide them with inaccurate and/or unreliable readings.

In some embodiments, the unique identifiers are used to prevent the use of a component in the biosensor. In some embodiments, for example, the unique identifiers are used to help prevent a microsensor from being reused, which can help maintain accurate performance of the biosensor and/or help maintain sanitary uses. In some embodiments, because a knockoff may not be configured for the biosensor's operational parameters and/or may not be compatible with various calibration adjustments, the unique identifiers (or lack thereof) are used to prevent knockoff components from being deployed. In still further embodiments, the unique identifiers are used to identify components that are not interoperable with a specific biosensor. For example, a microsensor patch may not be configured for use with the user's biosensor model, and may therefore result in accurate measurements if used. In such embodiments, the unique identifier can help identify incompatible components, thereby helping prevent the user from relying on inaccurate measurements.

In some embodiments, features of biosensors can be manufactured from a semiconductor substrate. The features can include, for example, microneedles, tissue-penetrating electrodes, sensors, circuitry, or the like. Production data can be generated during manufacturing of the elements and can include, without limitation, one or more processing parameters (e.g., deposition parameters, etching parameters, cutting parameters, diagnostic or probing parameters, etc.), probing outputs, measurements, characteristics of biosensors, or other production information that can be related to biosensor performance. The production data can be used to generate analyte detection information that is indicative of performance of features of the biosensor, and is sometimes referred to herein as predicting a performance of the biosensors and/or components thereof. Biosensor calibration routines, biosensor operational settings, manufacturing protocols, production data, acquisition protocols, and/or control programs (e.g., biosensor control programs, manufacturing equipment control programs, etc.) can be generated based on the analyte detection information in order to, for example, adjust a response to analyte concentrations of the biosensor and/or components thereof, increase and/or decrease operational service life, manage power consumption, and/or address various other goals set by physicians or users. The analyte detection information can vary based on the biosensor design. For detecting analytes in a user's skin, a biosensor can include one or more microneedles configured to be positioned in the user's skin. The analyte detection information can include, without limitation, data collected from operation of the microneedles analyzing interstitial fluid in the user's skin. For detecting analytes below the user's skin, the biosensor can have tissue-penetrating elements (e.g., needles, electrodes implanted using removable needles, etc.) with active regions configured to be located in subcutaneous tissue. In some embodiments, the biosensors draw fluids from the user to analyze the fluids.

In some embodiments, the production data can be analyzed to determine performance characteristics of the biosensors. The characteristics can be correlated to one or more candidate biosensor calibrations. The candidate biosensor calibrations can be used to generate biosensor control routines. In some embodiments, a trained machine-learning engine can evaluate multiple candidate calibrations to identify candidate calibrations suitable for achieving one or more target outcomes, such as threshold detection accuracy, biosensor performance life, etc. In some embodiments, a set of the production data can be selected based on identified correlations between the set and collected biosensor performance data. The biosensor performance data can include, without limitation, user biometric data, operational data, power usage data, malfunction or error data, user inputted data, etc. The set of the production data can be used to generate the candidate biosensor calibrations. The production data can include multianalyte related fabrication data and the biosensor calibration routine can be configured to calibrate the biosensor to increase accuracy of detection of analytes. The biosensor calibration routine can be generated based on one or more characteristics of, for example, microneedles of the biosensor.

When processing sequence of multiple substrates (e.g., wafers), characteristics of substrates can vary based on the order of substrate processing in the sequence. In some embodiments, the production data can include semiconductor fabrication data, including, without limitation, substrate-to-substrate variance data for a substrate incorporated into the biosensor. In this manner, wafer-level production data can be obtained and used to determine biosensor calibration routines, manufacturing routines, probing routines, or the like.

The methods disclosed herein can be used to evaluate biosensor performance data to determine, for example, known good features, known bad features, or other feature characteristics. The determination can be based on, for example, testing performance of the features, performing one or more measurements of the features, or other techniques disclosed herein. For example, a biosensor calibration routine can be configured to eliminate usage of known bad microneedles by, for example, avoiding sending drive signals to the known bad microneedles. In some embodiments, the signal processing, filters, and other features can be used to compensate for known bad microneedles. Compensation routines can be related to the number of known bad microneedles. For example, the calibration routine can amplify detection signals proportional to the number of known bad microneedles that do not provide detection signals. The criteria for identifying known and bad microneedles can be inputted by a user, determined using one or more machine learning engines, or other input source. In some embodiments, biosensor performance data collected from users can be used to periodically retrain machine-learning engines to periodically or continuously determine criteria for identifying and categorizing known and bad microneedles, features of biosensors, or the like. This process can be used to enhance the performance of the biosensors by, for example, increasing detection accuracy, detection sensitivity, detection life, or other performance characteristics. Machine-learning engines can determine threshold detection accuracy values for biosensors. The biosensors can be controlled to achieve the threshold detection accuracy value. In some embodiments, the biosensor can be rendered inoperative or disabled if a threshold detection accuracy value is not reached. A notification can be sent to the user to replace the biosensor or biosensor device. Data from the biosensor device can be sent to biosensor systems to enable analysis of inaccurate data collected by the biosensor.

In some embodiments, a system can manufacture biosensors configured to detect analytes in body fluids. The system can analyze received biosensor performance data from biosensors worn by users and corresponding biosensor production data to determine one or more biosensor inspection routines, biosensor calibration routines, control settings for biosensors, or the like. In some embodiments, the system can analyze received analyte detection data to determine one or more correlations between performance of the biosensors and their associated production data. A set of the production data related to performance of those biosensors can be identified based on one or more correlations and/or measurable parameters associated with the biosensor. Machine learning engines or other techniques disclosed herein can be used to identify the set of production data. In some embodiments, the production data includes measurements of biosensors, manufacturing parameters, or combinations thereof. The system can continuously or periodically analyze the data collected to provide real-time calibration of biosensor devices. Manufacturing techniques can also be periodically modified based on the collected data to provide an adaptive and dynamic manufacturing protocol.

Embodiments of the present technology will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

For ease of reference, exemplary biosensors and their components are sometimes described herein with reference to top and bottom, upper and lower, upwards and downwards, and/or horizontal plane, x-y plane, vertical, or z-direction relative to the spatial orientation of the embodiments shown in the figures. It is to be understood, however, that the biosensors (and their components) can be moved to, and used in, different spatial orientations without changing the structure and/or function of the disclosed embodiments of the present technology.

Further, although aspects of the technology are discussed primarily herein to track the development of microneedles and calibrating a biosensor based on the tracked development, one of skill in the art will understand that the scope of the invention is not so limited. Purely by way of example, the systems and methods disclosed herein can also be used to track the development of other components of a biosensor, such as alternative electrodes types (e.g., non-microneedles), components of a printed circuit board and/or semiconductor dies thereon, and the like. Accordingly, the scope of the invention is not confined to any subset of embodiments.

The headings provided herein are for convenience only and do not interpret the scope or meaning of the claimed present technology.

II. Systems for Biomonitoring and Healthcare Guidance

FIG. 1 is a schematic diagram of an exemplary computing environment 100 in which a biomonitoring and healthcare guidance system 102 ("system 102") operates, in accordance with embodiments of the present technology. As shown in FIG. 1, the system 102 is operably coupled to one or more user devices 104 via a network 108. The system 102 is also operably coupled to at least one database or storage component 106 ("database 106"). The system 102 can include processors, memory, and/or other software and/or hardware components configured to implement the various methods described herein. For example, the system 102 can be configured to monitor a patient's health state and provide predictive self-care guidance, as described in greater detail below.

The health state can be any status, condition, parameter, etc. that is associated with or otherwise related to the patient's health. In some embodiments, the system 102 can be used to identify, manage, monitor, and/or provide recommendations relating to diabetes, hypoglycemia, hyperglycemia, pre-diabetes, hypertension, hyperlipidemia, ketoacidosis, liver failure, congestive heart failure, hypoxia, kidney function, intoxication, dehydration, hyponatremia, shock, sepsis, trauma, water retention, bleeding, endocrine disorders, asthma, lung conditions, muscle breakdown, malnutrition, body function (e.g., lung functions, heart functions, etc.), physical performance (e.g., athletic performance), anaerobic activity, weight loss/gain, nutrition, wellness, mental health, focus, effects of medication, medication levels, health indicators, and/or user compliance. In some embodiments, the system 102 receives input data and performs monitoring, processing, analysis, forecasting, interpretation, etc. of the input data in order to generate instructions, notifications, recommendations, support, and/or other information to the patient that may be useful for self-care of diseases or conditions, such as chronic conditions (e.g., diabetes (type 1 and type 2), pre-diabetes, hypertension, hyperlipidemia, etc.).

The input data for the system 102 can include health-related information, contextual information, and/or any other information relevant to the patient's health state. For example, health-related information can include levels or concentrations of a biomarker, such as glucose, electrolytes, neurotransmitters, amino acids, hormones, alcohols, gases (e.g. oxygen, carbon dioxide, etc.), creatinine, blood urea nitrogen (BUN), lactic acid, drugs, pH, cell count, and/or other biomarkers. Health-related information can also include physiological and/or behavioral parameters, such as vitals (e.g., heart rate, body temperature (such as skin temperature), blood pressure (such as systolic and/or diastolic blood pressure), respiratory rate), cardiovascular data (e.g., pacemaker data, arrhythmia data), body function data, meal or nutrition data (e.g., number of meals; timing of meals; number of calories; amount of carbohydrates, fats, sugars, etc.), physical activity or exercise data (e.g., time and/or duration of activity; activity type such as walking, running, swimming; strenuousness of the activity such as low, moderate, high; etc.), sleep data (e.g., number of hours of sleep, average hours of sleep, variability of hours of sleep, sleep-wake cycle data, data related to sleep apnea events, sleep fragmentation (such as fraction of nighttime hours awake between sleep episodes, etc.), stress level data (e.g., cortisol and/or other chemical indicators of stress levels, perspiration), alc data, etc. Health-related information can also include medical history data (e.g., weight, age, sleeping patterns, medical conditions, cholesterol levels, disease type, family history, patient health history, diagnoses, tobacco usage, alcohol usage, etc.), diagnostic data (e.g., molecular diagnostics, imaging), medication data (e.g., timing and/or dosages of medications such as insulin), personal data (e.g., name, gender, demographics, social network information, etc.), and/or any other data, and/or any combination thereof. Contextual information can include user location (e.g., GPS coordinates, elevation data), environmental conditions (e.g., air pressure, humidity, temperature, air quality, etc.), and/or combinations thereof.

In some embodiments, the system 102 receives the input data from one or more user devices 104. The user devices 104 can be any device associated with a patient or other user, and can be used to obtain healthcare information, contextual information, and/or any other relevant information relating to the patient and/or any other users or patients (e.g., appropriately anonymized patient data). In the illustrated embodiment, for example, the user devices 104 include at least one biosensor 104*a* (e.g., blood glucose sensors, pressure sensors, heart rate sensors, sleep trackers, temperature sensors, motion sensors, or other biomonitoring devices), at least one mobile device 104*b* (e.g., a smartphone or tablet computer), and, optionally, at least one wearable device 104*c* (e.g., a smartwatch, fitness tracker). In other embodiments, however, one or more of the devices 104*a-c* can be omitted and/or other types of user devices can be included, such as computing devices (e.g., personal computers, laptop computers, etc.). Additionally, although FIG. 1 illustrates the biosensor(s) 104*a* as being separate from the other user devices 104, in other embodiments the biosensor(s) 104*a* can be incorporated into another user device 104.

The biosensor 104*a* can include various types of sensors, such as chemical sensors, electrochemical sensors, optical sensors (e.g., optical enzymatic sensors, opto-chemical sensors, fluorescence-based sensors, etc.), spectrophotometric sensors, spectroscopic sensors, polarimetric sensors, calorimetric sensors, iontophoretic sensors, radiometric sensors, and the like, and combinations thereof. In some embodiments, the biosensor 104*a* is or includes a blood glucose sensor. The blood glucose sensor can be any device capable of obtaining blood glucose data from the patient, such as implanted sensors, non-implanted sensors, invasive sensors, minimally invasive sensors, non-invasive sensors, wearable sensors, etc. The blood glucose sensor can be configured to obtain samples from the patient (e.g., blood samples) and determine glucose levels in the sample. Any suitable technique for obtaining patient samples and/or determining glucose levels in the samples can be used. In some embodiments, for example, the blood glucose sensor can be configured to detect substances (e.g., a substance indicative of glucose levels), measure a concentration of glucose, and/or measure another substance indicative of the concentration of glucose. The blood glucose sensor can be configured to analyze, for example, body fluids (e.g., blood, interstitial fluid, sweat, etc.), tissue (e.g., optical characteristics of body structures, anatomical features, skin, or body fluids), and/or vitals (e.g., heat rate, blood pressure, etc.) to periodically or continuously obtain blood glucose data. Optionally, the blood glucose sensor can include other capabilities, such as processing, transmitting, receiving, and/or other computing capabilities. In some embodiments, the blood glucose sensor can include at least one continuous glucose monitoring (CGM) device or sensor that measures the patient's blood glucose level at predetermined time intervals. For example, the CGM device can obtain at least one blood glucose measurement every minute, 2 minutes, 5 minutes, 10 minutes, 15 minutes, 30 minutes, 30 minutes, 60 minutes, 2 hours, etc. In some embodiments, the time interval is within a range from 5 minutes to 10 minutes. Additional details of biosensors suitable for use with the present technology are provided below. Example biosensor devices, biosensors, and components of biosensors are discussed in connection with, for example, FIGS. 2-3C, 13A-13C, and 15A-15D and other biosensors disclosed herein are suitable for use with the biomonitoring and healthcare guidance system 102 of FIG. 1.

In some embodiments, some or all of the user devices 104 are configured to continuously obtain any of the above data (e.g., health-related information and/or contextual information) from the patient over a particular time period (e.g., hours, days, weeks, months, years). For example, data can be obtained at a predetermined time interval (e.g., once every minute, 2 minutes, 5 minutes, 10 minutes, 15 minutes, 30 minutes, 30 minutes, 60 minutes, 2 hours, etc.), at random time intervals, or combinations thereof. The time interval for data collection can be set by the patient, by another user (e.g., a physician), by the system 102, or by the user device 104 itself (e.g., as part of an automated data collection program). The user device 104 can obtain the data automatically or semi-automatically (e.g., by automatically prompting the patient to provide such data at a particular time), or from manual input by the patient (e.g., without prompts from the user device 104). The continuous data may be provided to the system 102 at predetermined time intervals (e.g., once every minute, 2 minutes, 5 minutes, 10 minutes, 15 minutes, 30 minutes, 30 minutes, 60 minutes, 2 hours, etc.), continuously, in real-time, upon receiving a query, manually, automatically (e.g., upon detection of new data), semi-automatically, etc. The time interval at which the user device 104 obtains data may or may not be the same as the time interval at which the user device 104 transmit the data to the system 102.

The user devices 104 can obtain any of the above data and can provide output in various ways, such as using one or more of the following components: a microphone (either a separate microphone or a microphone imbedded in the device), a speaker, a screen (e.g., using a touchscreen, a stylus pen, and/or in any other fashion), a keyboard, a mouse, a camera, a camcorder, a telephone, a smartphone, a tablet computer, a personal computer, a laptop computer, a sensor (e.g., a sensor included in or operably coupled to the user device 104), and/or any other device. The data obtained by the user devices 104 can include metadata, structured content data, unstructured content data, embedded data, nested data, hard disk data, memory card data, cellular telephone memory data, smartphone memory data, main memory images and/or data, forensic containers, zip files, files, memory images, and/or any other data/information. The data can be in various formats, such as text, numerical, alpha-numerical, hierarchically arranged data, table data, email messages, text files, video, audio, graphics, etc. Optionally, any of the above data can be filtered, smoothed, augmented, annotated, or otherwise processed (e.g., by the user devices 104 and/or the system 102) before being used.

In some embodiments, any of the above data can be queried by one or more of the user devices 104 from one or more databases (e.g., the database 106, a third-party database, etc.). The user device 104 can generate a query and transmit the query to the system 102, which can determine which database may contain requisite information and then connect with that database to execute a query and retrieve appropriate information. In other embodiments, the user device 104 can receive the data directly from the third-party database and transmit the received data to the system 102, or can instruct the third-party database to transmit the data to the system 102. In some embodiments, the system 102 can include various application programming interfaces (APIs) and/or communication interfaces that can allow interfacing between user devices 104, databases, and/or any other components.

Optionally, the system 102 can also obtain any of the above data from various third-party sources, e.g., with or without a query initiated by a user device 104. In some embodiments, the system 102 can be communicatively coupled to various public and/or private databases that can store various information, such as census information, health statistics (e.g., appropriately anonymized), demographic information, population information, and/or any other information. Additionally, the system 102 can also execute a query or other command to obtain data from the user devices 104 and/or access data stored in the database 106. The data can include data related to the particular patient and/or a plurality of patients or other users (e.g., health-related information, contextual information, etc.) as described herein.

The database 106 can be used to store various types of data obtained and/or used by the system 102. For example, any of the above data can be stored in the database 106. The database 106 can also be used to store data generated by the system 102, such as previous predictions or forecasts produced by the system 102. In some embodiments, the database 106 includes data for multiple users, such as a plurality of patients (e.g., at least 50, 100, 200, 500, 1000, 2000, 3000, 4000, 5000, or 10,000 different patients). The data can be appropriately anonymized to ensure compliance with various privacy standards. The database 106 can store information in various formats, such as table format, column-row format, key-value format, etc. (e.g., each key can be indicative of various attributes associated with the user and each corresponding value can be indicative of the attribute's value (e.g., measurement, time, etc.)). In some embodiments, the database 106 can store a plurality of tables that can be accessed through queries generated by the system 102 and/or the user devices 104. The tables can store different types of information (e.g., one table can store blood glucose measurement data, another table can store user health data, etc.), where one table can be updated as a result of an update to another table.

In some embodiments, one or more users can access the system 102 via the user devices 104, e.g., to send data to the system 102 (e.g., health-related information and/or contextual information) and/or receive data from the system 102 (e.g., predictions, notifications, recommendations, instructions, support, etc.). The users can be individual users (e.g., patients, healthcare professionals, etc.), computing devices, software applications, objects, functions, and/or any other types of users and/or any combination thereof. For example, upon obtaining any of the input data discussed above, the user device 104 can generate an instruction and/or command to the system 102, e.g., to process the obtained data, store the data in the database 106, extract additional data from one or more databases, and/or perform analysis of the data. The instruction/command can be in a form of a query, a function call, and/or any other type of instruction/command. In some implementations, the instructions/commands can be provided using a microphone (either a separate microphone or a microphone imbedded in the user device 104), a speaker, a screen (e.g., using a touchscreen, a stylus pen, and/or in any other fashion), a keyboard, a mouse, a camera, a camcorder, a telephone, a smartphone, a tablet computer, a personal computer, a laptop computer, and/or using any other device. The user device 104 can also instruct the system 102 to perform an analysis of data stored in the database 106 and/or inputted via the user device 104.

As discussed further below, the system 102 can analyze the obtained input data, including historical data, current real-time data, continuously supplied data, calibration data, and/or any other data (e.g., using a statistical analysis, machine learning analysis, etc.), and generate output data. The output data can include predictions of a patient's health state, interpretations, recommendations, notifications, instructions, support, and/or other information related to the obtained input data. The system 102 can perform such analyses at any suitable frequency and/or any suitable number of times (e.g., once, multiple times, on a continuous basis, etc.). For example, when updated input data is supplied to the system 102 (e.g., from the user devices 104), the system 102 can reassess and update its previous output data, if appropriate. In performing its analysis, the system 102 can also generate additional queries to obtain further information (e.g., from the user devices 104, the database 106, or third party sources). In some embodiments, the user device 104 can automatically supply the system 102 with such information. Receipt of updated/additional information can automatically trigger the system 102 to execute a process for reanalyzing, reassessing, or otherwise updating previous output data.

In some embodiments, the system 102 is configured to analyze the input data and generate the output data using one or more machine learning models. The machine learning models can include supervised learning models, unsupervised learning models, semi-supervised learning models, and/or reinforcement learning models. Examples of machine learning models suitable for use with the present technology include, but are not limited to: regression algorithms (e.g., ordinary least squares regression, linear regression, logistic regression, stepwise regression, multivariate adaptive regression splines, locally estimated scatterplot smoothing), instance-based algorithms (e.g., k-nearest neighbor, learning vector quantization, self-organizing map, locally weighted learning, support vector machines), regularization algorithms (e.g., ridge regression, least absolute shrinkage and selection operator, elastic net, least-angle regression), decision tree algorithms (e.g., classification and regression trees, Iterative Dichotomiser 3 (ID3), C4.5, C5.0, chi-squared automatic interaction detection, decision stump, M5, conditional decision trees), Bayesian algorithms (e.g., naïve Bayes, Gaussian naïve Bayes, multinomial naïve Bayes, averaged one-dependence estimators, Bayesian belief networks, Bayesian networks), clustering algorithms (e.g., k-means, k-medians, expectation maximization, hierarchical clustering), association rule learning algorithms (e.g., apriori algorithm, ECLAT algorithm), artificial neural networks (e.g., perceptron, multilayer perceptrons, back-propagation, stochastic gradient descent, Hopfield networks, radial basis function networks), deep learning algorithms (e.g., convolutional neural networks, recurrent neural networks, long short-term memory networks, stacked auto-encoders, deep Boltzmann machines, deep belief networks), dimensionality reduction algorithms (e.g., principle component analysis, principle component regression, partial least squares regression, Sammon mapping, multidimensional scaling, projection pursuit, discriminant analysis), time series forecasting algorithms (e.g., exponential smoothing, autoregressive models, autoregressive with exogenous input (ARX) models, autoregressive moving average (ARMA) models, autoregressive moving average with exogenous inputs (ARMAX) models, autoregressive integrated moving average (ARIMA) models, autoregressive conditional heteroskedasticity (ARCH) models), and ensemble algorithms (e.g., boosting, bootstrapped aggregation, AdaBoost, blending, stacking, gradient boosting machines, gradient boosted trees, random forest).

Although FIG. 1 illustrates a single set of user devices 104, it will be appreciated that the system 102 can be operably and communicably coupled to multiple sets of user devices, each set being associated with a particular patient or user. Accordingly, the system 102 can be configured to receive and analyze data from a large number of patients (e.g., at least 50, 100, 300, 500, 1000, 3000, 3000, 4000, 5000, or 10,000 different patients) over an extended time period (e.g., weeks, months, years). The data from these patients can be used to train and/or refine one or more machine learning models implemented by the system 102, as described below.

The system 102 and user devices 104 can be operably and communicatively coupled to each other via the network 108. The network 108 can be or include one or more communications networks, and can include at least one of the following: a wired network, a wireless network, a metropolitan area network ("MAN"), a local area network ("LAN"), a wide area network ("WAN"), a virtual local area network ("VLAN"), an internet, an extranet, an intranet, and/or any other type of network and/or any combination thereof. Additionally, although FIG. 1 illustrates the system 102 as being directly connected to the database 106 without the network 108, in other embodiments the system 102 can be indirectly connected to the database 106 via the network 108. Moreover, in other embodiments one or more of the user devices 104 can be configured to communicate directly with the system 102 and/or database 106, rather than communicating with these components via the network 108.

The various components 102-108 illustrated in FIG. 1 can include any suitable combination of hardware and/or software. In some embodiment, components 102-108 can be disposed on one or more computing devices, such as, server(s), database(s), personal computer(s), laptop(s), cellular telephone(s), smartphone(s), tablet computer(s), and/or any other computing devices and/or any combination thereof. In some embodiments, the components 102-108 can be disposed on a single computing device and/or can be part of a single communications network. Alternatively, the components can be located on distinct and separate computing devices. For example, although FIG. 1 illustrates the system 102 as being a single component, in other embodiments the system 102 can be implemented across a plurality of different hardware components at different locations.

Figure 2:
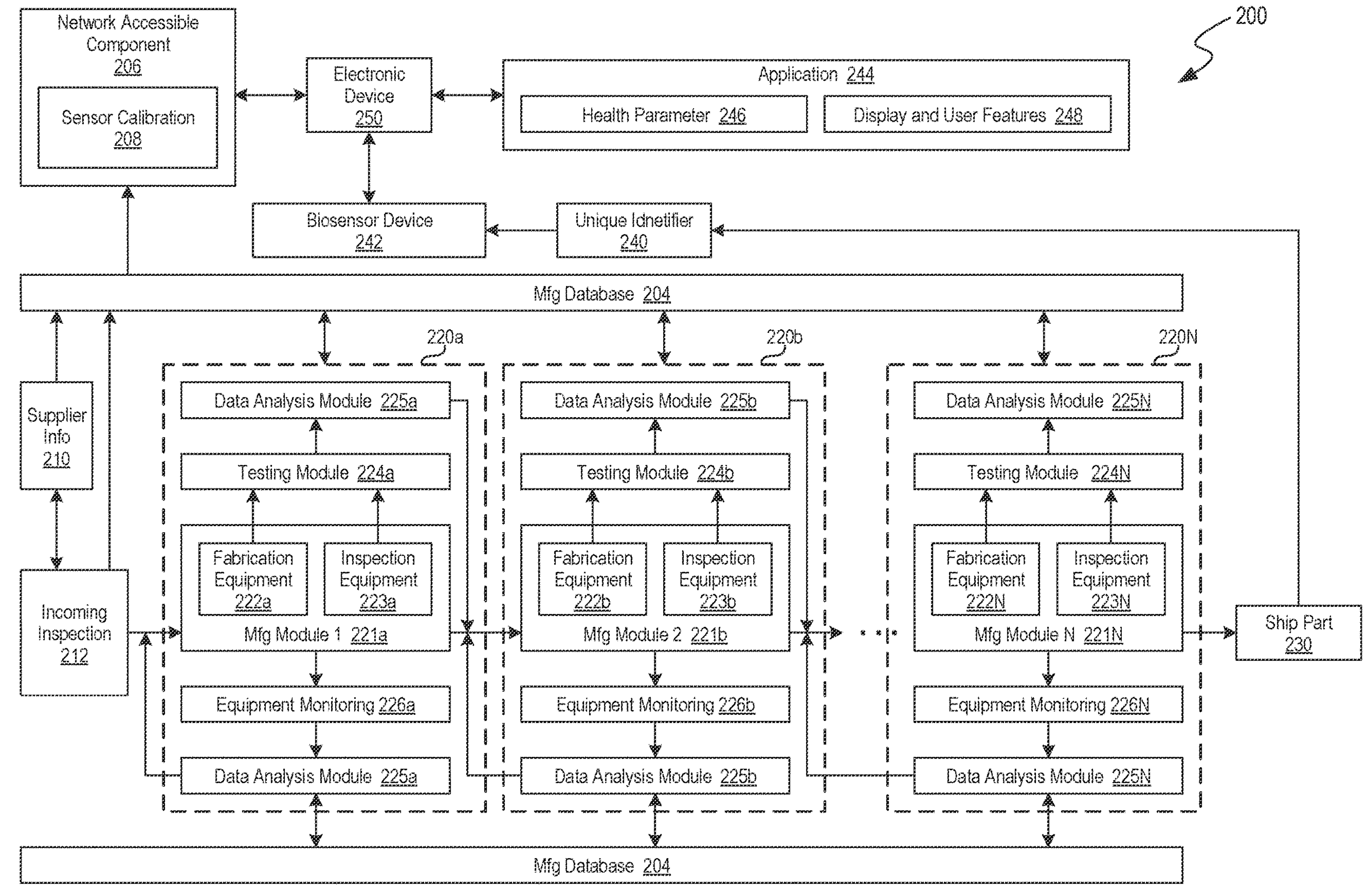
FIG. 2 is a schematic block diagram illustrating a system for monitoring and/or tracking biosensors in accordance with some embodiments of the present technology.

FIG. 2 is a schematic block diagram illustrating a system 200 for monitoring and/or tracking one or more biosensors 242 (one shown schematically) during and after manufacturing in accordance with some embodiments of the present technology. The system 200 can be used to perform any of the methods described herein.

In the illustrated embodiment, the system 200 includes a manufacturing database 204 and a network accessible component 206 in communication with the manufacturing database 204. The system 200 also includes a variety of supplier, inspection, measurement, and manufacturing modules that are in communication with the manufacturing database 204. As a result, the manufacturing database 204 can receive, store, and/or communicate data related to the development and/or a performance of the biosensor components (e.g., production data) at various stages of the manufacturing process. For example, as illustrated, the manufacturing database 204 can receive information from a supplier information module 210 ("supplier info module 210") that includes specification information from suppliers, an incoming inspection module 212 used to evaluate materials before substantive fabrication, and/or from any manufacturing modules 220 (shown schematically as first, second, and N manufacturing modules 220*a*-220N, sometimes referred to collectively as "manufacturing modules 220").

Each of the manufacturing modules 220*a*-220N can be associated with one or more stages of manufacturing and can include production modules 221 that include fabrication equipment 222 and/or inspection equipment 223. The fabrication equipment 222 can execute stages of manufacturing (e.g., various etching, dicing, cutting, deposition, and/or patterning processes) and/or generate production data related to various in-line metrics on the fabrication process (e.g., characteristics and/or operating parameters of the fabrication equipment 222, date of manufacturing, run time of fabrication equipment 222 before and/or during production, and the like). Similarly, the inspection equipment 223 can monitor and/or test the components of the biosensors during and/or after the manufacturing stage to generate additional (or alternative) production data (e.g., by performing an imaging analysis of the wafer, and/or any other suitable tests described in more detail below). In various embodiments, the production data can include sensor-level data, wafer-level data, batch-level data, and/or machine-level data.

Once the production data is generated, the production module 221 can communicate the production data to a testing module 224 and/or a data analysis module 225. The testing module 224 can review the production data to determine if any measurements are missing and prompt the production module 221 for the missing data. Additionally, or alternatively, the testing module 224 can perform one or more additional measurements (e.g., electro-chemical measurements) that temporarily remove the components from production. In various embodiments, the additional measurements can be performed at the sensor level, wafer level and/or batch level.

The testing module 224 can then send the production data to a data analysis module 225. The data analysis module 225 can parse and/or combine the production data to generate aggregate scores and/or otherwise filter the production data. Additionally, or alternatively, the data analysis module 225 can review the production data to evaluate the development of the components, predict performance parameters of the components (e.g., an expected response to an analyte of interest), generate calibration routines for the components, generate calibration adjustments and/or factors, generate alterations to the manufacturing process when a shortcoming is detected, and/or perform any other suitable determination. Additional details on examples of the evaluations performed that can be performed by the data analysis module 225 are discussed in more detail below with respect to FIGS. 7 and 8. The data analysis module 225 can then send the production data and/or any evaluations of the production data (e.g., the calibration adjustments) to the manufacturing database 204.

As further illustrated in FIG. 2, the production module 221 can communicate metrics (e.g., equipment monitoring data) on the manufacturing equipment to an equipment monitoring module 226. The equipment monitoring module 226 can help track metrics on the use of the fabrication equipment 222 (e.g., the milage) and help detect problems in the fabrication equipment 222 indicating a need for maintenance. The equipment monitoring module 226 can then send any associated production data to the data analysis module 225. The data analysis module 225 can receive and process the production data to assess the tool health after cycles of production, predict when tool maintenance will be necessary, and/or update further production cycles based on the assessment of the tool health. Additional details on examples of the assessments and predictions performed that can be performed by the data analysis module 225 are discussed in more detail below with respect to FIG. 12. The data analysis module 225 can then send the production data, assessments, and/or any predictions related to the tool health to the manufacturing database 204.

As discussed in more detail below, the manufacturing process can track the production data to each biosensor individually using a unique identifier (e.g., a unique alphanumeric identification number, QR code, and/or identifier stored in a memory device in the component of the biosensor 242). That is, as the production data is sent to the manufacturing database 204, it is linked and/or tracked to relevant unique identifiers. In the illustrated embodiment, at the end of the manufacturing process, each component of the biosensor 242 is shipped by a shipping module 230 with a physical corresponding unique identifier 240. Before and/or during use, a biosensor 242 can communicate the unique identifier 240 to an electronic device 250 (e.g., a user's smartphone, tablet, personal computer, and the like) to begin a calibration process. The electronic device 250 can then communicate with the network accessible component 206, which uses the unique identifier 240 to retrieve the production data and/or calibration adjustments (e.g., a calibration routine, adjustments to operating parameters for the biosensor 242, adjustments to signal filters, and the like) specific to the component of the biosensor 242 from the manufacturing database 204. The network accessible component 206 can relay the calibration adjustments to the electronic device 250, which can then relay the calibration adjustments to the biosensor 242 to increase the accuracy of measurements made by the biosensor 242 and/or interpretations of the measurements made by the biosensor 242.

In some embodiments, the manufacturing database 204 includes a component that performs one or more of the evaluations discussed above with respect to the data analysis module 225. In some embodiments, the manufacturing database 204 communicates raw production data to another component to perform the evaluations discussed. In the illustrated embodiment, for example, the manufacturing database 204 can communicate raw production data to the network accessible component (e.g., the network accessible component 206) that includes a sensor calibration module 208 that can determine appropriate calibration adjustments for each component in the biosensor 242 and/or instructions for a calibration process. In some embodiments, the manufacturing database 204 communicates the production data to the network accessible component 206 when the components of the biosensor 242 are shipped. Alternatively, or additionally, the manufacturing database 204 can communicate the production data to the network accessible component 206 when queried by the network accessible component 206 providing the unique identifier 240 (e.g., after a component is installed in the biosensor 242).

In a specific example of the system 200, the component can be a disposable microsensor patch installed into the biosensor 242. After installation, the electronic device 250 can send a prompt to the network accessible component 206 to execute a calibration process to determine the calibration adjustments. The prompt includes the unique identifier 240, and the network accessible component 206 uses the unique identifier 240 to query the manufacturing database 204 for the production data specific to the microsensor patch installed in the biosensor 242. The manufacturing database receives the query, retrieves the production data specific to the microsensor patch, and sends the retrieved production data back to the network accessible component 206. The network accessible component 206, via the sensor calibration module 208, determines appropriate calibration adjustments specific to the microsensor patch and communicates the calibration adjustments back to the electronic device 250. The electronic device 250 can then communicate the calibration adjustments to the biosensor 242 to adjust one or more operational parameters. Additionally, or alternatively, the electronic device 250 can use the calibration adjustments to interpret signals from the biosensor 242. For example, the electronic device 250 can have an application 244 running that includes a health parameter module 246 (e.g., a blood-glucose estimation module) that can use the calibration adjustments to refine an interpretation of the signals from the biosensor 242 (e.g., refine an estimate of the user's blood-glucose levels). The application 244 can also include a display module 248 that can display information about the calibration adjustments to the user and/or display outputs from the health parameter module 246.

In some embodiments, the network accessible component 206 can store a set of predetermined calibration adjustments for each component of the biosensor 242 after the component is shipped. When the network accessible component 206 receives a suitable request from the electronic device 250 (e.g., the first time the microsensor patch is used in the biosensor 242), the network accessible component 206 can look up the appropriate set of calibration adjustments for that component, based on the unique identifier 240, and send the calibration adjustments to the electronic device 250 and/or directly to the biosensor 242. Additionally, or alternatively, if a manufacturer (or other party) determines that updates to the calibration adjustments are needed (e.g., updates to the operational parameters, recalls, warnings about potential malfunctions, and the like), the network accessible component 206 can push updates to the electronic device 250 and/or the biosensor 242. The biosensor 242 can be, or be incorporated into, the biosensor 104*a* (FIG. 1), biosensor device 300 (FIGS. 3A-3C), biosensor 1300 (FIGS. 13A-13D), or other devices disclosed herein.

III. Exemplary Biosensor Technology

Biosensors can include disposable sensors (e.g., sensors for monitoring specific condition(s)) and reusable electronics and can include electronics for detecting sensors and then detecting different analytes and/or using additional information (e.g., exercise, food, etc.) in algorithms. Detection can be performed using different algorithms used with different groups of users and algorithms selected based on user health data. Local processing can be performed based on AI/ML trained algorithms (e.g., when network connectivity is lost). Disposable sensors can be configured to detect electrolytes, glucose, bicarbonate, creatinine, body urea nitrogen (BUN), sodium, iodide, iodine and potassium of a user's blood chemistry, biomarkers, cell count, hormone levels, alcohol content, gases (e.g., carbon dioxide, oxygen, etc.), blood saturation levels (e.g., blood oxygen saturation), drug concentrations/metabolism, environmental conditions, and/or pH and analytes within a user's body fluid. In some embodiments, the biosensors can be configured to compensate for biofouling associated with interstitial fluid-based monitoring, deliver medication, reduce or limit signal noise, compensate for time delays with glucose changes for signal detection associated with interstitial fluid-based detection, and/or manage over the air updates (e.g., algorithm updates, detection updates, software module updates). The number, configuration, and/or functionality of the biosensor device(s) can be selected based on desired sensing capabilities, such as sensing glucose, oxygen (e.g., blood oxygen saturation), carbon dioxide, bicarbonate, potassium, sodium, magnesium, chloride, lactic acid, urea, creatinine, alcohols, ethanol, neurotransmitters, amino acids, temperature (e.g., body temperature, skin temperature, etc.), vitals, heart rate, body function, activity, user location, user elevation data, environmental conditions (e.g., air pressure, humidity, temperature, air quality, etc.), or combinations thereof.

Figure 3A:
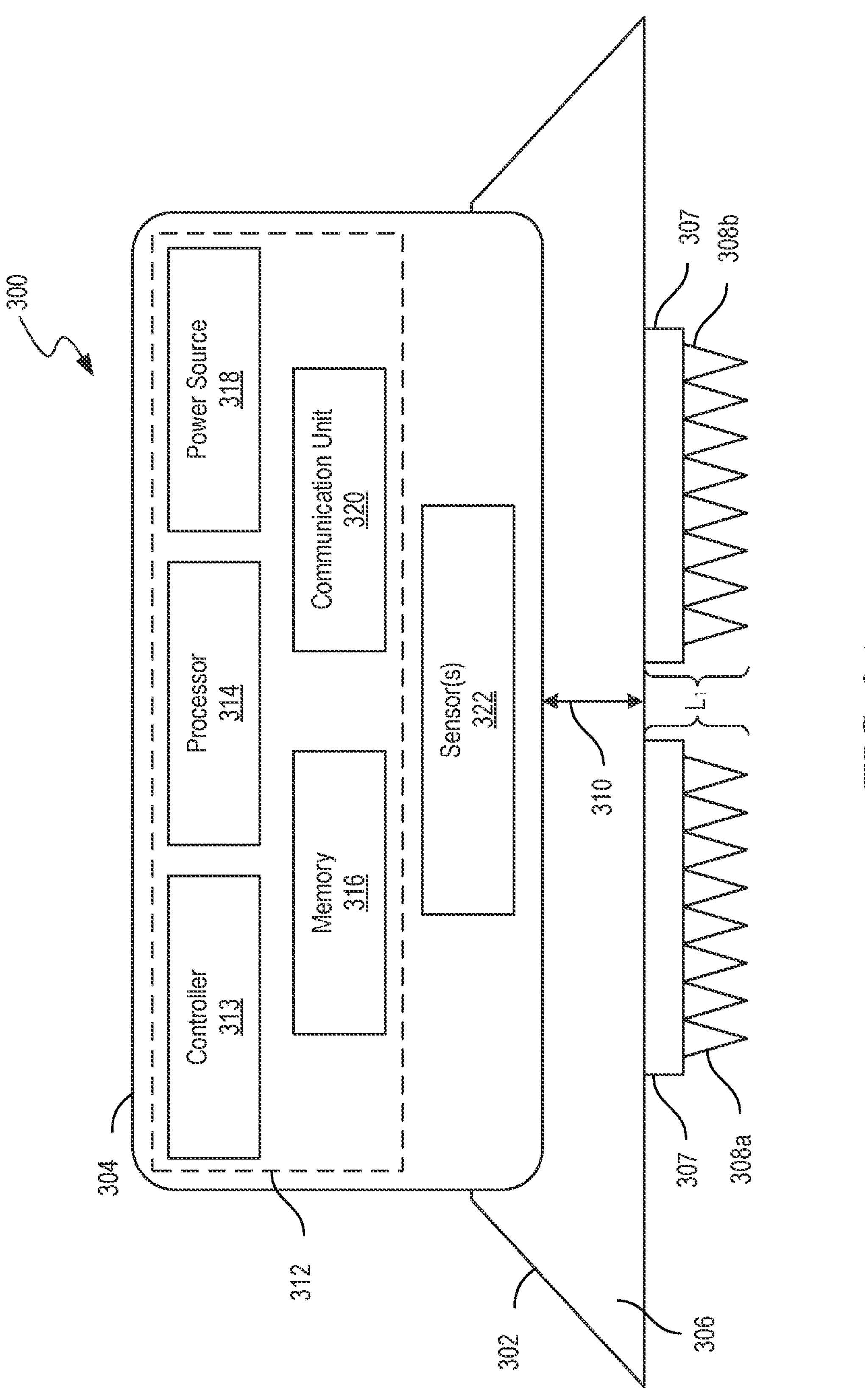
FIGS. 3A-3C are schematic illustrations of biosensor devices configured in accordance with some embodiments of the present technology.
Figure 3B:
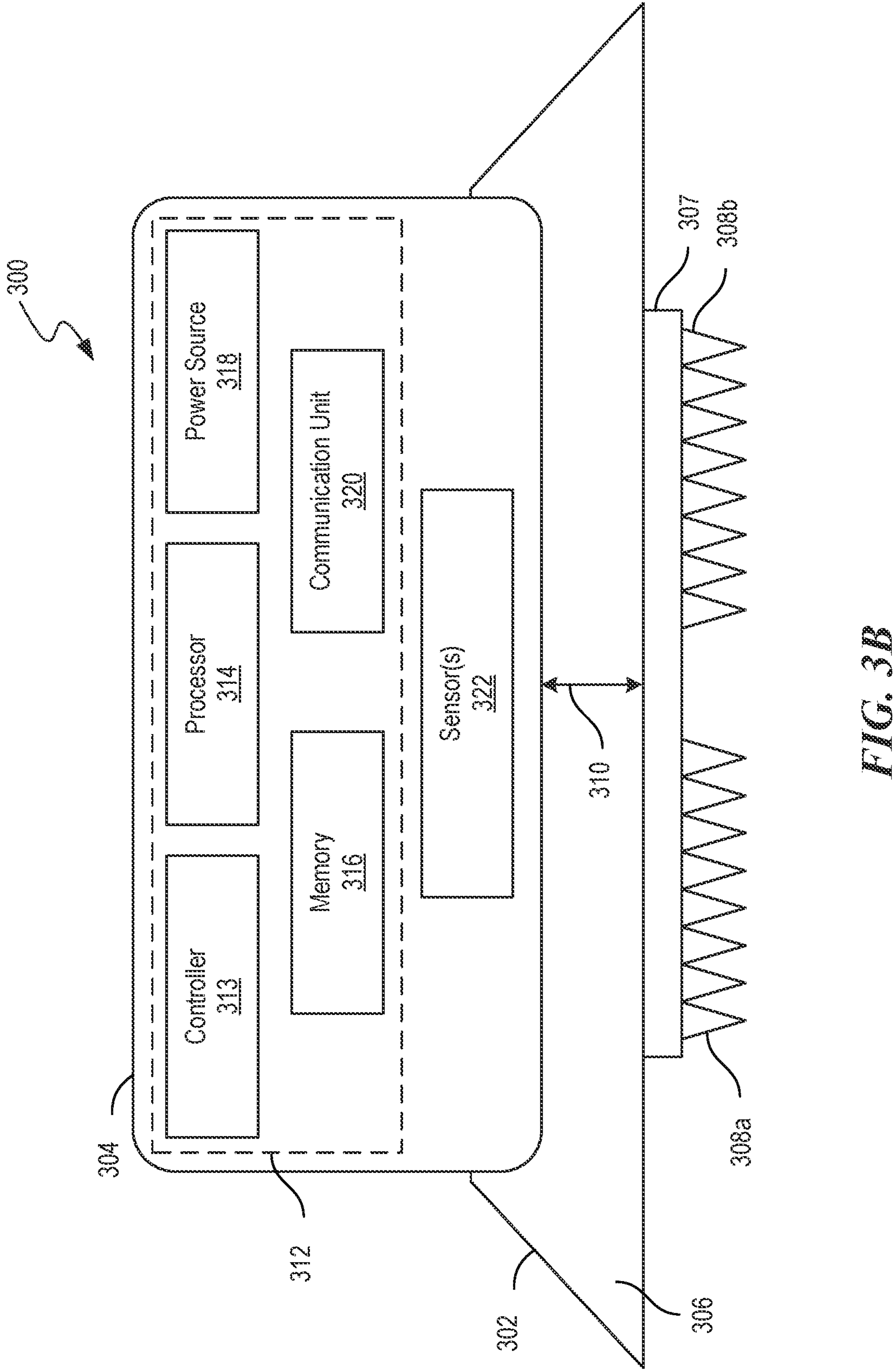

FIGS. 3A and 3B and the accompanying description provide various examples of biosensors that are suitable for use with the biomonitoring and healthcare guidance system 102 of FIG. 1. Specifically, FIGS. 3A and 3B are schematic illustrations of a biosensor device 300 ("device 300") configured in accordance with some embodiments of the present technology. The device 300 can be a wearable patch sensor configured to be applied to a user's body in order to obtain user health data in a non-invasive or minimally-invasive manner. The device 300 can be used in any of the systems and methods described herein (e.g., as the biosensor 104*a* of FIG. 1). The device 300 includes a patch 302 (also referred to as a "disposable patch," "microsensor patch," "microsensor," "patch portion," "base portion," or "sensing component") and a pod 304 (also referred to as a "reusable pod," "pod portion," "capsule portion," or "electronics component"). The patch 302 can be coupled to the pod 304 (e.g., releasably coupled or permanently affixed) to form the device 300.

The patch 302 can include a substrate 306 configured to couple to the user's body (e.g., to the surface of the skin) via adhesives or other suitable temporary attachment techniques. The base portion also includes at least one array of microneedles 308 (two shown, referred to individually as a first array of microneedles 308*a* and a second array of microneedles 308*b*) coupled to and/or supported by the substrate 306. The microneedles 308 can generally have a length $L_1$ (FIG. 3A) and can be configured to penetrate into the user's skin to access interstitial fluid therein. In some embodiments, when the device 300 is applied to the skin, the length $L_1$ is selected such that the microneedles 308 extend only into the stratum corneum and epidermis, and do not penetrate into the dermis or hypodermis (subcutaneous tissue). This approach can reduce or avoid pain and/or discomfort, while still providing accurate detection of analytes in the epidermal interstitial fluid. The microneedles 308 can be configured to detect one or more analytes in the interstitial fluid, such as glucose, gases, electrolytes, BUN, creatinine, ketones, alcohols, amino acids, neurotransmitters, hormones, biomarkers, drugs, pH, cell count, and/or any of the other analytes described herein. Each of the microneedles 308 can be configured to detect a single analyte, or some or all of the microneedles 308 can be configured to detect multiple analytes (e.g., two, three, four, five, or more different analytes). Optionally, some or all of the microneedles 308 can be configured to detect physiological parameters, such as electrical properties (e.g., biopotential, bioimpedance), body temperature, etc. In some embodiments the first array of microneedles 308*a* is configured to detect a first set of one or more analytes while the second array of microneedles **308*b*** is configured to detect a second set of one or more analytes.

The array can include any suitable number of microneedles 308 (e.g., 25 microneedles), and the microneedles 308 can be arranged in any suitable geometry (e.g., a 5×5 grid) and/or the device 300 can include two, three, four, five, or more arrays of microneedles 308. In embodiments where the device 300 includes multiple arrays, each array can be configured to perform a different function, or some of the arrays can perform the same function. For example, as discussed above the first array of microneedles **308*a* can be configured to detect a first set of analytes, while the second array of microneedles 308*b* can be configured to detect a second set of analytes. Further, the device 300 can include a third array of microneedles is included and configured to detect a third set of analytes, and so on. Alternatively, or additionally, the first array of microneedles 308*a* can be configured as a working electrode, the second array of microneedles 308*b*** can be configured as a reference electrode, and a third array of microneedles (not shown) can be configured as a counter electrode.

Referring to FIG. 3A, the first and second arrays of microneedles **308*a*, 308*b* are coupled to the substrate 306 through a base substrate 307 separated into two sections. For example, the separate configuration can be used when the first and second arrays of microneedles 308*a*, 308*b* are configured as separate electrodes (e.g., a working electrode and a reference electrode). In some embodiments, the first and second arrays of microneedles 308*a*, 308*b* are coupled to the substrate 306 through a single base substrate 307, as illustrated in FIG. 3B. For example, the single configuration can be used when the first and second arrays of microneedles 308*a*, 308*b* are configured to detect and/or respond to separate sets of analytes of interest and/or to simplify the construction of the device. The substrate 307 can include, without limitation, one or more layers, circuitry, pads, mounting features, etc. In some embodiments, the first and second arrays of microneedles 308*a*, 308*b* are integrally formed (e.g., via etching, cutting, build-up, etc.) with the base substrate 307**.

Referring to FIGS. 3A and 3B together, the first and second arrays of microneedles **308*a*, 308*b* can each generate signals (e.g., electrical signals) indicative of health parameter values (e.g., analyte concentration and/or physiological values). For example, the first array of microneedles 308 can generate a first electrical signal indicative of a first analyte, a second electrical signal indicative of a second analyte, and so on. Optionally, either (or each) of the first and second arrays of microneedles 308*a*, 308*b* can generate at least a first electrical signal indicative of an analyte and at least a second electrical signal indicative of a physiological parameter. The first and second arrays of microneedles 308*a*, 308*b* can each be electrically coupled to the patch 302, which in turn can be electrically coupled to the pod 304 (schematically represented by arrow 310). The electrical connections between the first and second arrays of microneedles 308*a*, 308*b*, patch 302, and pod 304 can include any suitable combination of pins, contacts, wires, traces, etc. Accordingly, the signals generated by the microneedles 308 can be transmitted to the pod 304** for storage and/or processing.

The pod 304 can be a capsule, module, or other durable structure that couples to the patch 302 in order to assemble the device 300. The pod 304 can be mechanically coupled to the patch 302 using any suitable temporary or permanent attachment method, such as interference fit, snap fit, threading, fasteners, bonding, adhesives, and/or suitable combinations thereof. The pod 304 can include a casing or housing that encloses an electronics assembly 312 (also referred to herein as an "electronics subsystem") of the device 300. The electronics assembly 312 can include one or more electronic components configured to perform the various operations described herein, such as a controller 313, processor 314, memory 316, power source 318, and communication unit 320. The controller 313 can be include any number of processors 314, memory 316, and other electronic components disclosed herein. Optionally, the pod 304 can also include one or more sensors 322 for measuring physiological parameters. The pod 304 can also include other electronic components not shown in FIG. 3, such as additional signal processing circuitry (e.g., multiplexer, analog front end (AFE), amplifier, filter, analog-to-digital converters (ADCs)), clock circuitry, power management circuitry, user input/output devices, and the like.

The processor 314 can be any component suitable for controlling the operations of the device 300, such as a microprocessor, microcontroller, field-programmable gate array (FPGA), application-specific integrated circuit (ASIC), and the like. For example, the processor 314 can receive and process signals generated by either (or both) of the first and second arrays of microneedles **308*a*, 308*b* and/or the sensor(s) 322 in order to generate one or more measurements of health parameters (e.g., analyte levels, biopotential values, bioimpedance values, body temperature values, heart rate values, oxygen levels, etc.). In some embodiments, the processor 314 receives and processes at least a first electrical signal from any of the microneedles 308 to generate a first health measurement (e.g., an analyte level), and at least a second electrical signal from the sensor(s) 322 to generate a second health measurement (e.g., a physiological parameter). The processor 314 can be configured to receive and process any number of electrical signals (e.g., two, three, four, five, or more electrical signals) obtained by different sensing components of the device 300 to generate measurements of multiple health parameters (e.g., two, three, four, five or more different health parameters). Optionally, the processor 314 can use the health measurements to generate predictions, recommendations, notifications, etc. As another example, the processor 314 can control transmission of raw sensor data, processed data, health measurements, predictions, etc., to a remote device (e.g., a smartphone, smartwatch, or other user device or remote server). In a further example, the processor 314 can receive instructions from a remote device for controlling the operation of the device 300 (e.g., powering on, powering off, updating calibration and/or other signal processing parameters, device pairing, etc.). The processor 314 can also control the operations of the other components of the device 300 (e.g., operations of the memory 316, power source 318, communication unit 320, other sensor(s) 322**, etc.).

The memory 316 can store instructions to be executed by the processor 314 and/or data generated during operation of the device 300. For example, the memory 316 can store raw and/or processed sensor data, as well as generated health measurements, predictions, recommendations, notifications, etc. The memory 316 can also store operating parameters for the device 300, such as calibration parameters, signal processing parameters, algorithms or programs (e.g., for generating health measurements, predictions, etc.), and so on. The memory 316 can also store one or more unique identifiers associated with any of the components of the device 300. The memory 316 can include any suitable combination of volatile and non-volatile memory, such as flash memory, EEPROM, etc. The memory can store instructions that are executable by the processor 314 to, for example, analyze collected data, control operation of the microneedles 308 or the like to generate health measurements, predictions, recommendations, notifications. In some embodiments, the memory 316 stores disabling routines for disabling usage of the pod 304 and/or microneedles 308 in response to identifying a disabling event. The disabling event can include, but is not limited to, expired microneedles, needles, and the like; reused microneedles, needles, and the like; detected malfunctioning; improper placement of the device 300 on the user; operation errors; incorrect microneedles, needles, and the like (e.g., microneedles not configured to detect correct analytes); etc. For example, the pod 304 can receive a manufacture date, expiration date, and/or other suitable data to determine whether the microneedles 308 are past an expected shelf life. A reused patch 302 can be detected when installed and a notification can be sent to the user to help prevent the device 300 from being placed on the user. Malfunctioning can be detected before, during, or after placement on the user. Improper device placement can be detected upon installation or continued use. Placement and needle positions can be continuously or intermittently determined for short-term use, long-term use (e.g., over 4 weeks), etc. Routines can be configured based on the expected period of use and include, without limitation, calibration routines that compensate for one or more of production data, physiological changes, chemistry changes, power source levels, user settings, combinations thereof, or the like. The biosensor device 300 can include computer-readable media having computer-readable storage media (e.g., "non-transitory" media) and computer-readable transmission media.

The power source 318 can be any component suitable for powering the operations of the device 300, such as a rechargeable battery, non-rechargeable battery, or suitable combinations thereof. The power source 318 can output power to the first and second arrays of microneedles 308*a*, 308*b*, processor 314, memory 316, communication unit 320, sensor(s) 322, and/or any other electronic components on the patch 302 or pod 304. The power source 318 can include or be operably coupled to power management circuitry (not shown). The power management circuitry can detect the charge status of the power source 318 (e.g., fully charged, partially charged, low charge), can allow the device 300 to operate in various modes (e.g., low power, full power), and/or any other suitable power-related function.

The communication unit 320 can allow the device 300 to transmit data to and/or receive data from a remote device (e.g., a mobile device, smartwatch, remote server, etc.). The communication unit 320 can be configured to communicate via any suitable combination of wired and/or wireless communication modes. In some embodiments, for example, the communication unit 320 uses Bluetooth Low Energy (BLE) to transmit and receive data.

The sensor(s) 322 can include any suitable combination of sensors for monitoring various health parameters, such as an optical sensor (e.g., photoplethysmography (PPG) sensor, pulse oximeter), heart rate sensor, blood pressure sensor, electrocardiogram (ECG) sensor, activity or motion sensor (e.g., accelerometer, gyroscope), temperature sensor (e.g., thermistor), location sensor, humidity sensor, etc. Each sensor can generate a respective set of signals, which can be received and processed by the processor 314 to generate health measurements and/or other user data. In some embodiments, the device 300 includes at least one, two, three, four, five, or more different sensors 322 for measuring physiological and/or other user parameters. Each sensor 322 can be located at any suitable region of the pod 304, such as at or near an upper surface, lower surface, lateral surface, or within an interior cavity of the pod 304. In other embodiments, however, some or all of the sensor(s) 322 can instead be located in the patch 302, rather than in the pod 304. For example, a temperature sensor can be located in the patch 302 in order to generate measurements of the user's skin temperature.

In some embodiments, the patch 302 is a disposable component that is configured for short-term use (e.g., no more than 4 weeks, 3 weeks, 2 weeks, 1 week, 6 days, 5 days, 4 days, 3 days, 2 days, 1 day, 12 hours, etc.), while the pod 304 is a reusable component that is configured for longer-term use (e.g., at least 1 week, 2 weeks, 3 weeks, 4 weeks, 1 month, 2 months, 3 months, 6 months, 1 year, etc.). This approach can be advantageous for reducing overall cost of the device 300, particularly in embodiments where the pod 304 includes more expensive components (e.g., the electronics assembly 312 and/or other sensor(s) 322). In such embodiments, the reusable pod 304 can be coupled to the disposable patch 302 to assemble the device 300 for use, and can be decoupled from the disposable patch 302 when the disposable patch 302 is to be replaced. As such, a single reusable pod 304 can be used with multiple different disposable patches 302, which can reduce the overall cost of the device 300, and enhance device longevity and adaptability. Optionally, a single reusable pod 304 can be used with multiple disposable patches 302 that detect different types of analytes. For example, the reusable pod 304 can be configured to interface with a first disposable patch 302 configured to detect a first set of analytes, a second disposable patch 302 configured to detect a second set of analytes, a third disposable patch 302 configured to detect a third set of analytes, and so on. In other embodiments, however, the patch 302 and pod 304 can both be disposable components, or can both be reusable components.

The device 300 can be configured to obtain and process the signals generated by the first and second arrays of microneedles 308*a*, 308*b* and/or the sensor(s) 322 in order to determine measurements for one or more health parameters, such as measurements of glucose, gases, electrolytes, BUN, creatinine, ketones, cholesterol, alcohols, amino acids, neurotransmitters, hormones, disease biomarkers, drugs, pH, cell count, heart rate, body temperature, blood pressure, respiratory rate, cardiovascular data, body function data, meal or nutrition data, physical activity or exercise data, sleep data, stress level data, a1c data, and so on. In some embodiments, the electronics assembly 312 is configured to implement one or more algorithms, such as algorithms for sensor calibration, signal conditioning, determining presence of and/or values for health parameters based on the sensor signals, predicting current and/or future values for health parameters based on the sensor signals, etc. The algorithms can be stored locally at the electronics assembly 312 (e.g., in the memory 316) such that the device 300 can operate without being in communication with a separate computing device or system (e.g., a cloud computing network, remote server, user device, etc.). In such embodiments, the locally-stored algorithms can be periodically updated, e.g., via firmware updates and/or other modifications received from the separate computing device by the communication unit 320. Alternatively or in combination, some or all of the algorithms can be stored at the separate computing device or system. In some embodiments, local processing can be performed onboard the device 300 for certain situations (e.g., when network connectivity is lost), while processing can be performed at a separate computing device or system in other situations (e.g., when network connectivity is available).

The operation of the device 300 can be customized based on the particular health parameters to be detected. For example, the patch 302 can include a respective memory (not shown) configured to store identifier information for the patch 302, such as the type and/or configuration of the microneedles 308, the type and/or configuration of the microneedle arrays, the types of analytes and/or physiological parameters detected by the microneedles 308, the types of other sensors included in the patch 302, a unique patch ID (e.g., a serial number), a lot ID, manufacturing date, expiration date and/or expected lifetime, and/or any other suitable information. In some embodiments, the processor 314 is configured to detect when the pod 304 is coupled to the patch 302. Once the pod 304 is connected to the patch 302, the processor 314 can interrogate or otherwise communicate with the patch 302 to detect the identifier information for the patch 302. The processor 314 can access and read the identifier information, and can then adjust the parameters and/or algorithms used to process the electrical signals generated by the patch 302 (e.g., by the microneedles 308), based on the identifier information. For example, the processor 314 can use the identifier information to determine detection capabilities of the patch 302 (e.g., which analytes and/or physiological values the patch 302 is configured to detect). The processor 314 can select an appropriate locally-stored algorithm for processing the signals generated by the patch 302 and/or determining health parameters from the signals. The algorithm can vary depending on the microneedle type and/or configuration, type of detected analyte or parameter, the manufacturing information for the patch 302 (e.g., batch or lot ID), the expected lifetime of the patch 302, other available sensor data, or any other suitable factor. Additionally, parameter detection can be performed using different algorithms used with different groups of users and algorithms selected based on user health data. The locally-stored algorithms can be updated based on the health parameters (e.g., via updates received from a separate user device, cloud computing system, etc.).

In embodiments where the pod 304 is configured for use with multiple patches 302 having different functionalities (e.g., different detection capabilities), when the pod 304 is coupled to a new patch 302, the processor 314 can use the identifier information received from the patch 302 to assess the functionality of the patch 302. If the processor 314 determines that the patch 302 has newly available functionality that the processor 314 is not currently programmed to accommodate, the processor 314 can retrieve the appropriate algorithms, calibration parameters, signal processing parameters, and/or other updates from a remote device (e.g., a user device, cloud computing system, etc.). Accordingly, the software implemented by the pod 304 can be rapidly and dynamically updated to accommodate different and/or new patch functionalities.

The health measurements produced by the device 300 can be used to generate personalized healthcare guidance, such as one or more predictions, recommendations, suggestions, feedback, and/or diagnosis for a number of diseases, conditions, or health states. For example, blood pressure can be monitored and/or predicted based on optical data (e.g., PPG data), electrical data (e.g., ECG data), heart rate data, user data, and/or activity data. As another example, sleep (e.g., sleep patterns, sleep quality) can be tracked and/or predicted based on heart rate data, skin temperature data, and/or activity data. In a further example, respiratory illness (e.g., COVID-19, allergies, infections etc.) can be monitored and/or predicted based on skin temperature data, blood pressure data, and/or respiration rate. The health measurements can be used to detect a condition, distinguish between different conditions (e.g., infection versus allergies), and/or monitor the progression of the condition. In yet another example, fertility can be tracked and/or predicted based on skin temperature data. The personalized guidance can be generated based solely on the health measurements from the device 300, or can be generated through a combination of health measurements and other information (e.g., information from any number of sensor data streams, user data sets, etc.). The healthcare guidance can be generated locally onboard the device 300, by a user device that receives health measurement data from the device 300 (e.g., via a mobile application on a user's smartphone or smartwatch), by a cloud computing system or remote server that receives health measurement data from the device 300, or any suitable combination thereof.

The configuration of the device 300 shown in FIGS. 3A and 3B can be modified in many different ways. For example, in other embodiments, the array of microneedles 308 can be omitted such that the device 300 does not include or otherwise use microneedle-based analyte detection. In such embodiments, the patch 302 may include other sensor types (e.g., a temperature sensor, a metal electrode for ECG sensing), or may not include any sensors at all, such that all sensing operations are performed by the sensor(s) 322 (e.g., motion sensor, optical sensor, etc.) located in the pod 304.

Figure 3C:
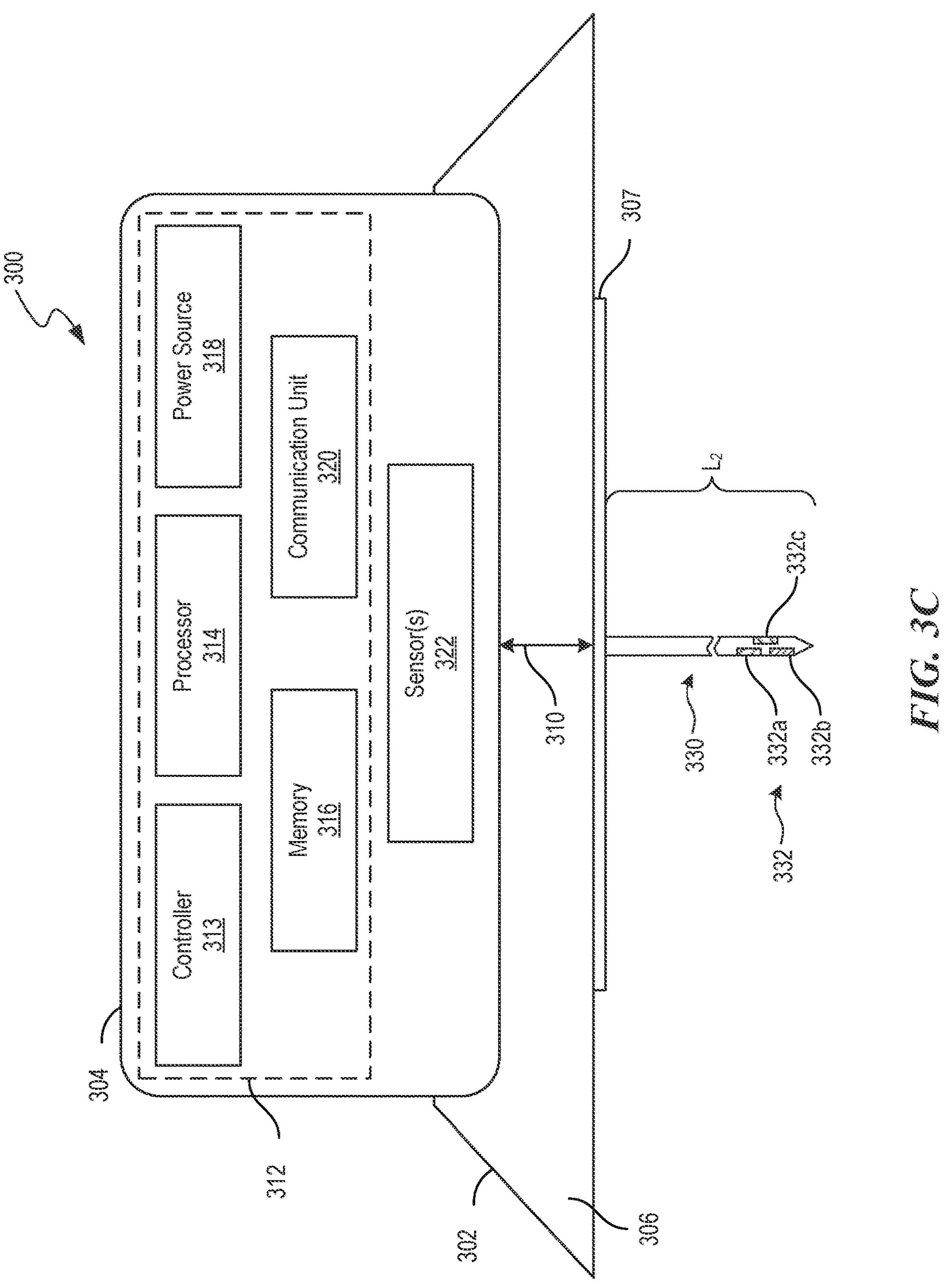

FIG. 3C illustrates the device 300 of FIGS. 3A and 3B with another alternative arrangement in accordance with further embodiments of the present technology. In the illustrated embodiment, the patch 302 includes a skin-penetrating needle 330 ("needle 330") having a length $L_2$ that is significantly longer than the length $L_1$ of the microneedles 308 discussed above with reference to FIGS. 3A and 3B. Accordingly, the needle 330 is configured to penetrate into and/or through the dermis or hypodermis (subcutaneous tissue) of the user to access a blood sample and/or interstitial fluid (e.g., subcutaneous interstitial fluid) within the user's body. While this configuration can be associated with increased installation pain for the user and some discomfort while deployed, this configuration can access fluids with higher concentrations of analytes of interest and can include a plurality of single-analyte or multi-analyte needles 330. As a result, the device 300 may be able to provide accurate measurements through the needle 330 more easily than through the microneedles 308 illustrated in FIGS. 3A and 3B.

As further illustrated in FIG. 3C, the needle 330 can be a multianalytes detecting needle that includes a plurality of detecting regions or electrodes 332 (three shown, referred to individually as first-third electrodes 332*a-c*) that can each be electrically and/or chemically isolated from each other. As a result, similar to the discussion above, each of the first-third electrodes 332*a-c* can be configured differently. Purely by way of example, the first electrode 332*a* can be configured as a first working electrode for detecting a first set of analytes (e.g., glucose, gases, electrolytes, BUN, creatinine, ketones, alcohols, amino acids, neurotransmitters, hormones, biomarkers, drugs, pH, cell count, and/or any combination therein), the second electrode 332*b* can be configured as a reference electrode, and the third electrode 332*c* can be configured as a counter electrode. In some embodiments, the needle 330 can be multianalyte needle and include features (e.g., multiple electrodes, active regions, layers, etc.) discussed in connection with FIGS. 15A-15D.

As another example of an alternative arrangement, any of the components of the device 300 discussed above with reference to FIGS. 3A and 3B can be separated into discrete subcomponents (e.g., multiple processors 314, multiple memories 316, etc.), combined into a single component (e.g., the processor 314 and communication unit 320 can be integrated into a single chip), or omitted altogether. In a still further example, any of the components of the device 300 can be positioned at different locations (e.g., some or all of the sensor(s) 322 can be located on the patch 302 instead of the pod 304). In some embodiments, the device 300 can include a combination of one or more arrays of the microneedles 308 and the needles 330. For example, the first and second arrays of microneedles 308*a*, 308*b* can detect analyte(s) in shallow tissue (e.g., dermis, epidermis, etc.) and the needle(s) 330 can detect one or more analytes in deeper tissue. The number, detection capabilities, dimensions, and features of the needles can be selected based on target detection capabilities. Additionally, the microneedles 308 and/or the needle 330 can be in the form of electrodes or sensing elements delivered into tissue using, for example, delivery needles, puncturing elements, etc.

Additional details on exemplary biosensors, methods of biomonitoring, and related technologies are disclosed in U.S. Pat. Nos. 9,008,745; 9,182,368; 10,173,042; U.S. application Ser. No. 15/601,204 (US Pub. No. 3017/0251958); U.S. application Ser. No. 15/876,678 (U.S. Pub. No. 3018/0140235); U.S. application Ser. No. 14/812,288 (US Pub. No. 3016/0029931); U.S. application Ser. No. 14/812,288 (US Pub. No. 3016/0029966); US Pub. No. 3017/0128009; U.S. App. No. 62/855,194; U.S. App. No. 62/854,088; and U.S. App. No. 62/970,282, which are all hereby incorporated by reference in their entireties. These technologies can be used with, incorporated into, and/or combined with systems, methods, features, and components disclosed herein. Biosensors can be configured to monitor invasively, minimally invasively, or non-invasively. The user devices discussed in connection with FIG. 1 and FIG. 2, as well as the methods discussed in connection with FIGS. 4-12 and 14A-14C can be used with or include biosensors, hardware, patches, and/or wearables disclosed in U.S. Pat. Nos. 9,008,745; 9,182,368; 10,173,042; U.S. application Ser. No. 15/601,204 (US Pub. No. 3017/0251958); U.S. application Ser. No. 15/876,678 (U.S. Pub. No. 3018/0140235); U.S. application Ser. No. 14/812,288 (US Pub. No. 3016/0029931); U.S. application Ser. No. 14/812,288 (US Pub. No. 3016/0029966); US Pub. No. 3017/0128009; U.S. App. No. 62/855,194; U.S. App. No. 62/854,088; and U.S. App. No. 62/970,282. The configuration of the devices 300 can be selected based on the planned usage period and can be manufactured, tracked, and suitable for the technology discussed in connection with FIGS. 4-12 and 14A-14C. For example, low-profile multiday biosensors with a flexible adhesive pad are discussed in connection with FIGS. 13A-13D.

IV. Methods for Manufacturing and Calibrating Biosensors

In some embodiments, a manufacturing process for the biosensors described herein includes batch production processes. For example, a wafer-scale process can allow multiple biosensors and/or their components (e.g., disposable sensors, microsensors, electrodes, disposable electronics, reusable electronics, memory, chips, and/or various other components) to be produced from a single wafer, then singulated. In some embodiments, the manufacturing process identifies and tracks biosensors and/or their components (sometimes referred to collectively as "products") throughout the production process, for example, using manufacturing variance (e.g., wafer wafer-to-wafer variance, lot-to-lot variance, etc.), the location of products on the wafer, visual or other identifiers on the products and/or the wafer, and/or any other suitable process. In some embodiments, the products are tracked in groups (e.g., all products near the edge of the wafer, near the center of the wafer, in a line on the wafer, or any other suitable grouping). In some embodiments, the products are tracked individually (e.g., by assigning an x-y wafer-coordinate to each product, using an optical or other identifier (e.g., a scannable code, serial number, or mark on the wafer, or other suitable identifier), or through any other suitable process). Additionally or alternatively, the manufacturing process can identify and track substrates or wafers for substrate data or wafer data, respectively.

During production, the manufacturing process can also generate and store various production data related to the biosensors and/or their components. In some embodiments, the production data is collected at the wafer-level (e.g., for multiple wafers and/or a single wafer) and/or for biosensors on the wafers (e.g., for any two or more biosensors on the wafer and/or for individual biosensors), or any combination thereof. Examples of production data collected include deposition metrics, such as the rate and/or amount of materials deposited during a production step; deviations during production; characteristics and/or metrics of the manufacturing equipment used in production; temperature during production; and/or other suitable data. In some embodiments, the production data also includes information from one or more tests and/or analyses performed during production. The tests and/or analyses can be performed after each step of production, after stages of production are complete, after the wafer is complete, or at any other suitable interval. Examples of the tests and analyses include an imaging analysis of the wafer, a spectrophotometric analysis, electrode performance tests, sensor sampling, various other electro-chemical measurements, and/or any other suitable tests. Additional details on various examples of the production data are provided below.

The production data can be tracked to groups of wafers, individual wafers, groups of biosensors, individual biosensors, individual components of the biosensors, and/or groups of components, using one or more of the identifiers described above. For example, the test results for an individual microsensor for use in a biosensor can be tracked to the microsensor using the wafer location data for the microsensor. In some embodiments, the production data is tracked and stored in a central database. In some embodiments, measuring equipment is linked to the central database (e.g., through a network connection) to provide updates to the production data throughout the process. The updates can allow a calibration process to predict how the microsensor will perform once deployed, and generate one or more calibration adjustments that account for the predicted performance.

The calibration process can use the production data to predict various performance metrics about each microsensor and set corresponding operational parameters of the biosensor accordingly (e.g., to account for sensor sensitivity, drift, background current, gain, etc.). In some embodiments, the calibration process draws a direct correlation between production data and the performance metrics. For example, the calibration process can directly correlate sensitivity measured during production of biosensor components with a predicted sensitivity when the biosensor is applied to the user's skin. In some embodiments, the calibration process includes one or more artificial intelligence and/or machine learning models (e.g., regression analysis, principal component analysis, or any other suitable techniques) to predict the performance metrics based on a collection of the production data. In some embodiments, the calibration process then includes storing the predicted performance metrics and/or the calibration adjustments for use in a biomonitoring system to calibrate a biosensor before use. In some embodiments, the predicted performance and/or the calibration adjustments metrics are stored on a memory device (e.g., an electrically erasable programmable read-only memory (EEPROM), or other suitable memory device) and included in the biosensor and/or biosensor component. In some embodiments, the biosensor and/or individual biosensor components are assigned a unique identifier and the predicted performance metrics can be stored in a network accessible storage device (e.g., a network accessible server and/or a cloud storage device) using the unique identifier. The unique identifier can then be included with the biosensor and/or biosensor component, for example through a physical identifier on the biosensor (e.g., unique identification number, QR code, or other suitable visual identifier) and/or through a memory device in the biosensor. The biomonitoring system can then access the stored predicted performance metrics and/or the calibration adjustments using the unique identifier to use in calibrating the biosensor.

In some embodiments, the manufacturing process uses the production data to monitor the flow and development of wafers throughout production. Using the production data, the manufacturing process can improve yield from production and/or improve the quality of the biosensors produced. In some embodiments, for example, the manufacturing process uses the production data to adjust processing parameters in subsequent production steps to compensate for detected deviations. In a specific example, if the manufacturing process detects that too much material was deposited during a previous step, the manufacturing process can adjust parameters (e.g., shorten deposition time) to deposit less material during one or more subsequent production steps.

In some embodiments, the manufacturing process uses the production data to sort wafers and their components for different production stages. The sorting can shift wafers into different workflows to produce microsensor components with different functions for the final microsensor patch. For example, wafers can be sorted into different manufacturing tracks to produce microneedle arrays to be used as working electrodes, reference electrodes, or counter electrodes. In some embodiments, all three types of electrodes share the same or similar microneedle structure, so the wafers used to fabricate the electrodes may be the same or similar before the start of the wet chemical processing module (e.g., catalytic base deposition, Ag/AgCl deposition, enzyme matrix deposition, and/or protective layer deposition). Of the three types of electrodes, the working electrode may have the tightest manufacturing tolerances, since it is the electrode that is actively sensing the analyte of interest (e.g., glucose, lactic acid, potassium, etc.). For each step in the manufacturing process, in-line metrics and/or other production metrics can be used to monitor a number of characteristics of the wafer, and, if one or more of the metrics do not meet the requirements for the working electrode, the wafer can be routed into the reference electrode or counter electrode manufacturing processes, which may have more relaxed tolerances, rather than discarding the wafer. This approach allows for increased manufacturing efficiency and improved effective yield, since wafers would be used for alternate processes instead of being scrapped.

The types of measurements that can be used for these sorting decisions after any step in the process can include, but are not limited to, the following: physical dimensions (e.g., microneedle height, width, shape, tip sharpness, electrode area, surface roughness); spectroscopic characteristics (e.g., characteristics measured by UV/VIS measurements, fluorescence measurements, Fourier-transform infrared (FTIR) spectroscopy, circular dichroism, Raman spectroscopy, ellipsometry, polarization spectroscopy, optical correlation spectroscopy, fluorescence lifetime, and the like); electrical characteristics, such as resistance, capacitance, or impedance of any single layer or combination of layers; and/or electrochemical characteristics such as electrochemical impedance spectroscopy or electrochemical activity.

In some embodiments, the manufacturing process uses the production data to generate a report on "tool health" for one or more machines used during production. The tool health metrics can predict when maintenance is needed on any of the machines used in production to help reduce down time in production. For example, by predicting when maintenance will be needed, the manufacturing process can schedule machines for maintenance ahead of any problems developing rather than in response to problems. Additionally, or alternatively, the tool health metrics can prevent production steps on machines when they require maintenance (or just before), thereby reducing production steps on malfunctioning and/or damaged machines. By avoiding using machines needing maintenance, the manufacturing process can reduce deviations in the production of the biosensors, thereby increasing the yield of production.

Additional details on the production data collected in the manufacturing process and/or how the production data relates to the prediction of performance metrics are set out in the examples below. However, it will be understood that these are merely examples of the sources of production data and how they relate to the calibration process. In some embodiments, the manufacturing process includes gathering other suitable production data, e.g., from other tests and/or analyses. Further, in some embodiments, the calibration process can include additional (or alternative) analyses of the production data and/or subprocesses to predict the performance metrics for individual biosensors.

A. Imaging and/or Spectrophotometric Analyses

In some embodiments, the manufacturing process includes an automated image and/or spectrophotometric analysis of the wafer during production. The automated image analysis can use optical techniques (e.g., edge detection techniques, Fourier-transform infrared (FTIR) spectroscopy, ultraviolet-visible (UV/VIS) spectroscopy, fluorescence, ellipsometry, polarization spectroscopy, various types of optical correlation spectroscopy, fluorescence lifetime spectroscopy, and/or various other suitable measurement techniques) to generate an input in the production data. For example, in some embodiments, the automated image analysis can record the structure and/or dimensions of the microelectrodes being formed on the microsensor portion of the biosensor. As a result, the automated image analysis can calculate the surface area of the electrodes. In a specific, non-limiting example, the automated image analysis can include an automated counting technique (e.g., based on edge detection) to determine a number of microneedles formed on an electrode and record the number of microneedles.

The sensitivity of a biosensor may be partially dependent on the active surface area of the electrodes in the biosensor. Accordingly, the calibration process can use the calculated surface area from the automated image analysis to adjust a projected sensitivity for the biosensor. Returning to the specific example above, the active surface area of the electrodes can be dependent on the number of microneedles that are formed. Accordingly, the calibration process can use the number of detected microneedles to adjust a projected sensitivity for the biosensor.

In some embodiments, the manufacturing process performs the automated image analysis multiple times during the production of the biosensors. For example, the manufacturing process can perform the automated image analysis after each stage of etching and/or material deposition to track and model the development of the microelectrodes in the biosensor. In some embodiments, the factory calibration process uses the modeled development in conjunction with various other tests on the biosensor (e.g., chemical and/or electronic sensitivity tests) to further refine the relationship between the development of a biosensor and the sensitivity of the biosensor.

B. In-Line Metrics

In some embodiments, the manufacturing process includes measuring one or more in-line metrics (e.g., the rate and/or amount of material deposited and/or removed, the performance of the electrode, characteristics of the manufacturing equipment, metrics on the manufacturing equipment's performance, and/or various other suitable in-line metrics). The manufacturing process can measure one or more in-line metrics after any interval (e.g., after each step of production, after two or more steps of production, after major components are completed, or any other suitable interval) to help track the development of the biosensors and their performance.

The calibration process can then use the measured in-line metrics to predict the biosensor's performance and/or identify potential drivers of variation in biosensor performance. For example, the calibration process can use deposition metrics (e.g., how much of an enzyme and/or receptor has been applied to the biosensor) to project the biosensor's response on a user's body. Because the in-line metrics can include measuring biosensor performance at various stages in production, the calibration process can additionally (or alternatively) determine which steps in the production caused variations in performance and/or why the steps caused variations in performance.

In some embodiments, the calibration process identifies when variations are specific to a location on the wafer during manufacturing. For example, biosensors near the outside of a wafer may develop slower than biosensors near the center and be less sensitive during operation as a result. In some embodiments, that sensitivity is measured and tracked to individual biosensors and/or biosensors in various radial and/or spatial groups on the wafer. In some embodiments, as the total measurements of the in-line metrics increase, the calibration process learns to predict the radial and/or spatial variation in biosensor performance based on a biosensor's location on the wafer during production. Once the calibration process has learned a relationship, the calibration process can accurately predict a biosensor's sensitivity without needing to measure the sensitivity of every biosensor in production.

C. Sensor Sampling

In some embodiments, the manufacturing process includes sampling one or more electrodes from each wafer to measure the performance of a fully-built microsensor sensor using the sampled electrodes. In some embodiments, the sampling is done with a single point measurement spread across a wafer. In some embodiments, sampling includes a measurement of each electrode on the wafer. In some embodiments, sampling includes a measurement of one or more electrodes in one or more clusters (e.g., based on the location of the electrodes on the wafer).

The calibration process can use the measured performance to modify a projected biosensor performance during packaging of each biosensor. For example, the calibration process can predict an expected signal strength in response to a presence of one or more analytes in the interstitial fluid of the user's skin. The calibration process can then record the projected performance for each biosensor and make the same available to a biomonitoring system using the biosensor. For example, as discussed above, each biosensor can include a memory device and/or a unique identifier. The biomonitoring system can use the projected performance to adjust operation parameters and/or an interpretation of signals received from the biosensor during operation.

D. Electro-Chemical Measurements

In some embodiments, the manufacturing process includes measuring one or more electrical and/or chemical properties of the wafer substrate and/or any of the components being manufactured thereon. In some embodiments, the electrical measurements can include resistive, capacitive, and/or impedance measurements for any one layer or combination of layers. In some embodiments, the chemical measurements include measuring a reactive response to of one or more layers (e.g., measuring a response of the reactive layer 1512*c* discussed above with respect to FIG. 15A to one or more analytes of interest). The electrical and/or chemical measurements can be used to determine the properties and/or quality of any layer or the interface between layers. In some embodiments, the electrical and/or chemical measurements are taken after each stage of manufacturing to track the development of components on the wafer and/or the changes as they develop. In some embodiments, the calibration process then uses the electrical and/or chemical measurements to adjust sensor parameters to account for the electrical measurements. For example, the electrical and/or chemical measurements can be used to adjust one or more of the sensor poise potential, sensor gain, and/or electrical model that describes the sensor for analyzing transient sensor responses to dynamic signals, such as ramped voltages, cyclic voltammetry, electrochemical impedance spectroscopy, stepped voltages, and/or impulses.

E. Manufacturing History

In some embodiments, as discussed above, each biosensor (and/or any number or components thereof) has a memory device and/or unique identifier that identifies the biosensor to a biomonitoring system. The identification allows the biomonitoring system to identify metrics recorded during manufacturing and/or the predicted performance metrics for any number of the components of the biosensor. The identification also allows the biomonitoring system to access a manufacturing history for any number of the components of the biosensor. In some embodiments, the manufacturing history includes information on one or more of a component's location on the wafer during manufacturing, manufacturing date, materials used in manufacturing, and/or any other relevant manufacturing information. The biomonitoring system can use the historical information to help calibrate the specific biosensor in use.

In embodiments using information on the location of the components on the wafer during manufacturing, the calibration process can generate and/or access a model correlating the location of the component to performance metrics for the component. For example, the model can predict that a component will have a lower sensitivity if it is within a predetermined distance of the edge of the wafer. In some embodiments, the predetermined distance is about 1 mm, about 2 mm, about 5 mm, about 10 mm, or any other suitable distance from the edge. The calibration process can use the model to update predicted performance parameters and/or calibration adjustments for the component.

Further, the manufacturing process can use the model to reduce yield loss during production due to spatially dependent variation across the wafer. For example, conventional manufacturing processes may discard components manufactured near the edge of the wafer because of their different performance compared to components produced near the center of the wafer. Because the use of the model allows the calibration process to adjust predicted performance parameters based on the location of the biosensors during production, the manufacturing process described herein can avoid discarding such biosensors without introducing a source of error into the biomonitoring system.

In embodiments using information on the manufacturing date, for another example, the calibration process can account for a shelf life and/or storage related decline in biosensor performance using the manufacturing date. For example, the calibration process can generate and/or access a model correlating the time between production and use to a decline in biosensor performance. The calibration process can then use the model to update predicted performance parameters for each biosensor. The biomonitoring system can then modify one or more operation parameters to account for the decline in sensing performance (e.g., increase a drive voltage, lower a threshold for sensing an event, or other suitable adjustments).

Figure 4:
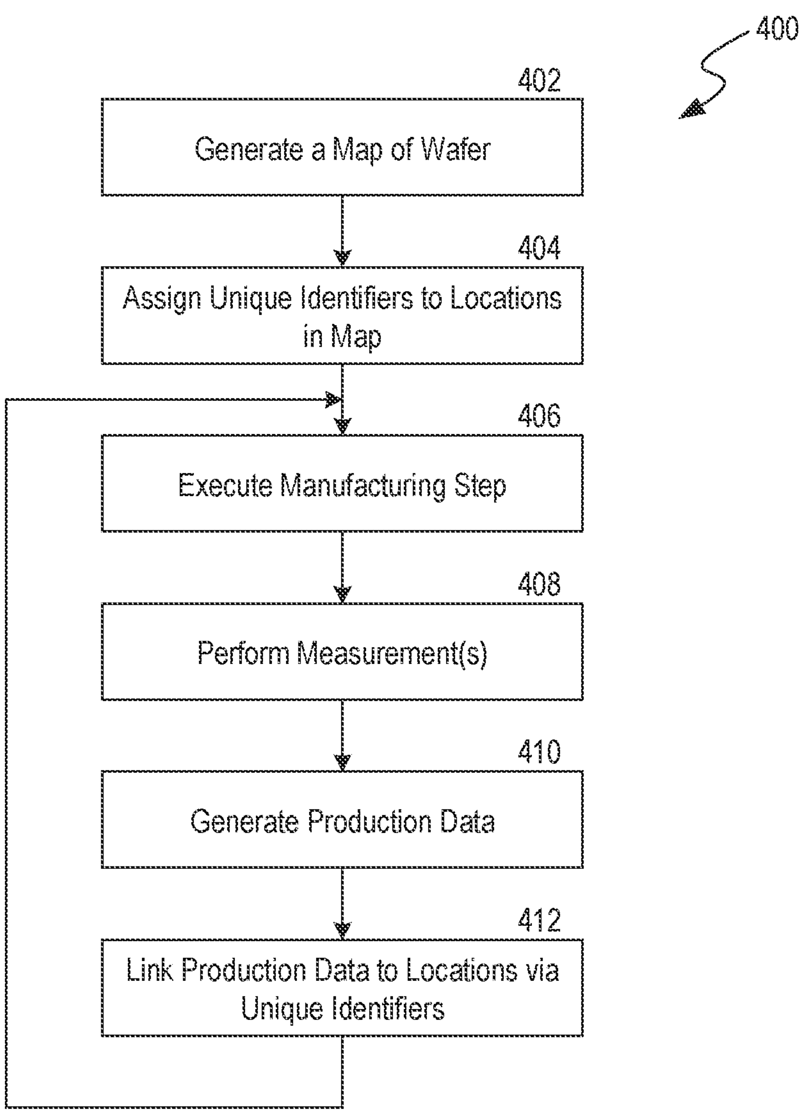
FIG. 4 is a flow diagram of a process for generating production data for a biosensor-related component during manufacturing in accordance with some embodiments of the present technology.

FIG. 4 is a flow diagram of a process 400 for generating production data for a biosensor-related component during manufacturing, as well as linking the production data to the component for later use, in accordance with some embodiments of the present technology. It will be understood that the component can be any suitable portion of a biosensor and/or an entire biosensor itself. For example, the component can be one of the first and second arrays of microneedles 308*a*, 308*b* of the device 300 discussed above with respect to FIG. 3, the entirety of the microneedles 308, the sensor 322, the entire patch 302, the pod 304, the entire device 300, and/or any other suitable component. Further, it will be understood that the process 400 can be executed by the system 102 discussed above with reference to FIG. 1 and/or in conjunction with any of the modules discussed above with reference to FIG. 2.

The process 400 begins at block 402 by generating a map of a wafer. The map can include a plurality of locations that each correspond to a planned location of one or more components. That is, each location on the map is empty at the beginning of wafer-level manufacturing, and each location contains at least one partially completed (or completed) component at the end of the wafer-level manufacturing. The wafer can then be singulated to separate individual components. The map can help allow the components to be tracked during, and after, manufacturing based on their location on the wafer.

In various embodiments, the locations on the map can be generated based on a cartesian coordinates, polar coordinates, and/or any other suitable coordinate system that allows the locations to be tracked to individual, identifiable points on the wafer. In some embodiments, the map can include one or more regions that correspond to a plurality of locations that are expected to develop relatively similar throughout manufacturing. For example, the map can include a central region and a peripheral region, and the production data for the components can include an indication of which region in the map the components are manufactured in. In some embodiments, the map includes a hierarchy of regions and locations. Purely by way of example, the map can include a plurality of regions, with multiple locations associated with precise cartesian coordinates in each region.

Figure 5:
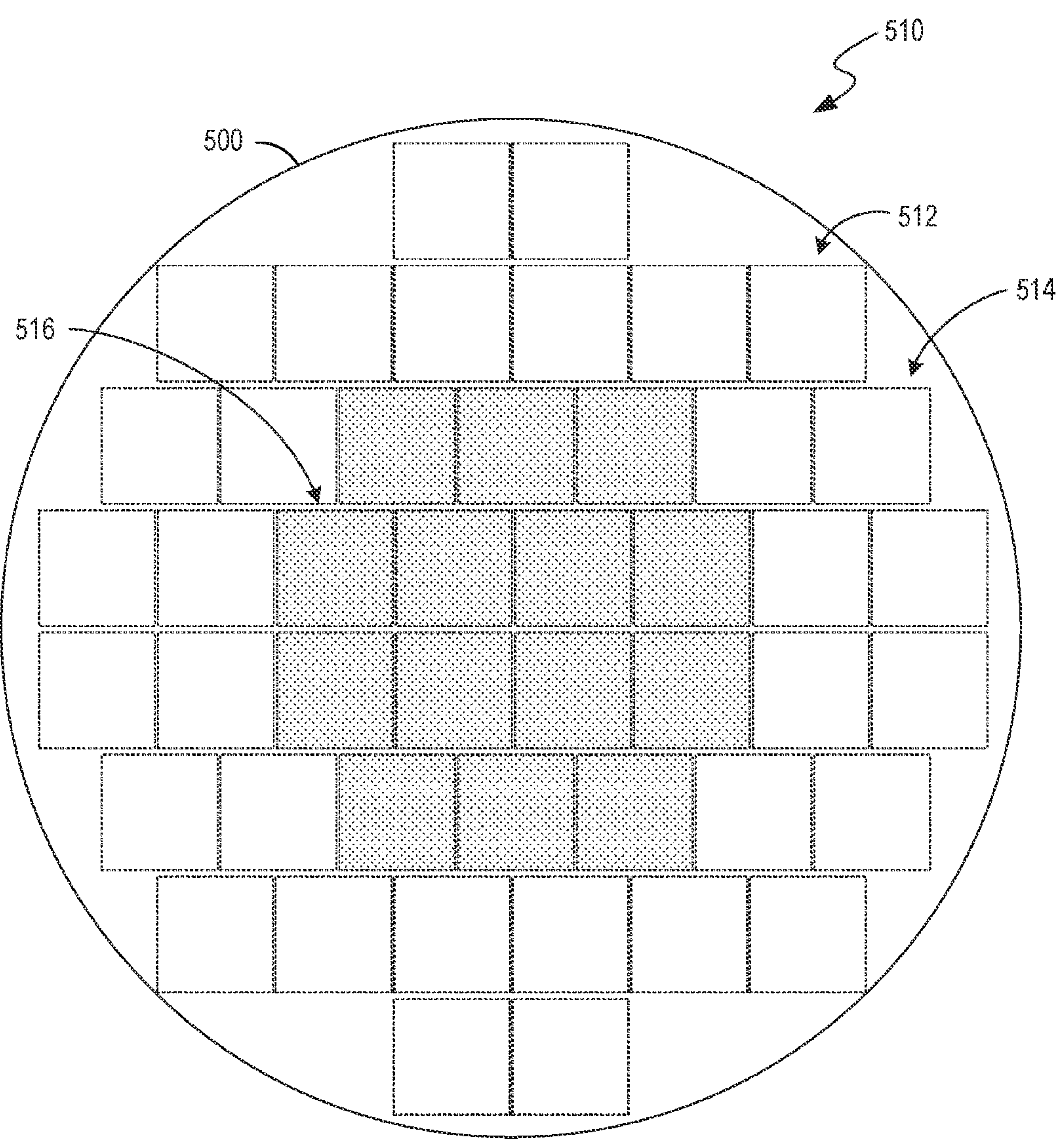
FIG. 5 is a partially schematic illustration of a map of a wafer generated during the process of FIG. 4 in accordance with some embodiments of the present technology.

FIG. 5 is a partially schematic illustration of a map 510 of a wafer 500 generated at block 402 of the process 400 of FIG. 4 in accordance with some embodiments of the present technology. As illustrated in FIG. 5, the map can include a plurality of locations 512. In the illustrated embodiment, each of the locations 512 is generally equal in size and generally equally spaced from other locations. The illustrated configuration is useful, for example, when the wafer 500 is used to manufacture a plurality of similar (or identical) components. In a specific, non-limiting example, each of the locations 512 in the map 510 can correspond to an individual electrode with an array of one or more microneedles being formed thereon. The formation of the microneedles can involve one or more wafer processes such as various etching processes, cutting processes, deposition processes, patterning processes, and/or any other suitable process. After each of the arrays of microneedles is complete, the wafer 500 can be diced to singulate each of the electrodes in each of the locations 512. In various other embodiments, the locations can have non-uniform sizes, can be spaced apart in a non-uniform manner, and/or can each correspond to a plurality of components (e.g., multiple electrodes per location).

In some embodiments, each of the locations 512 is associated with an address (e.g., an x-y coordinate) on the wafer 500 corresponding to the location's relative position. The relative position of each of the locations 512 can be tracked because the relative position can impact the development of the components in each of the locations 512. Purely by way of example, peripheral locations 514 (indicated by a lighter fill color) generally accumulate thinner layers during a deposition process than central locations 516 (indicated by a darker fill color). Accordingly, the relative position of each of the locations 512 can be used when extrapolating measurements between the locations 512, as discussed in more detail below.

Relatedly, each of the locations 512 can be associated with a general region on the wafer 500. In a specific, non-limiting example, the map 510 can include a first region corresponding to the peripheral locations 514 and a second region corresponding to the central locations 516. Similar to the exact relative positions discussed above, the categorization of each of the locations 512 into a region can be used when extrapolating measurements between the locations 512. For example, components manufactured in one of the peripheral locations 514 are more likely to have similar development to the components in the other peripheral locations 514 than the components manufactured in the central locations 516.

Returning to FIG. 4, the process 400 next includes assigning at least one unique identifier to each of the plurality of locations in the map at block 404. The unique identifier can be any alphanumeric code that allows the process 400, and any related manufacturing and/or calibration processes, to record, view, and/or update data specific to the component(s) manufactured in the location corresponding to the unique identifier. Purely by way of example, the unique identifier can be a serial number associated with a location of a single electrode on the wafer. During manufacturing, the process 400 can associate production data with the serial number to associate the production data with the resulting electrode.

At block 406, the process 400 includes executing one or more steps of manufacturing on the wafer. Purely by way of example, at block 406, the process 400 can include one or more rounds of layer deposition, patterning, etching, stripping, and the like that help form each of the plurality of microneedles 308 (FIG. 3).

At block 408, the process 400 includes performing one or more measurements at a selected location on the wafer. The measurements can include any of the measurements discussed above, including but not limited to: optical measurements of physical dimensions such as microneedle height, width, shape, tip sharpness, electrode area, surface roughness, number of edges; electrical characteristics such as resistance, capacitance, or impedance of any single layer or combination of layers; chemical characteristics such as a reactive response to one or more analytes, or electrochemical activity; and/or any other suitable measurement.

In some embodiments, the measurements are performed without removing the wafer from the manufacturing line (e.g., through optical and/or electrical components in a manufacturing apparatus). In some embodiments, the wafer is temporarily removed from production to be measured. In some embodiments, the measurements include destructive tests, such as chemical reaction tests that partially (or fully) destroy the structures in the measured location. Purely by way of example, a chemical test can cause a chemical reaction in a layer deposited on an array of microneedles to measure the reaction sensitivity of the microneedles. In so doing, the chemical reaction can partially (or fully) destroy the deposited layer, such that the array of microneedles in the tested location are no longer usable.

In some embodiments, one or more of the measurements can be specific to a subgroup of components at the location. By way of example, where each location is associated with an array of microneedles for a microsensor, one or more of the measurements can be specific to a subarray of microneedles based on their intended function. In on, non-limiting example, a first sub-array can be in manufacturing to detect a first group of analytes while a second sub-array can be in manufacturing to detect a second group of analytes. In this example, one or more of the measurements can be specific to the first sub-array and/or one or more of the measurements can be specific to the second sub-array. In another non-limiting example, a first sub-array can be in manufacturing to be included in a working electrode while a second sub-array can be in manufacturing to be included in a counter electrode. Accordingly, similar to above, one or more of the measurements can be specific to the first sub-array and/or one or more of the measurements can be specific to the second sub-array.

In some embodiments, discussed in more detail below with reference to FIGS. 14A-14C, the manufacturing process includes a wafer-wafer mounting stage, where the carrier wafer includes one or more sets of electronics (e.g., testing electronics, dummy circuits, operational circuits, ASICs, and the like). In such embodiments, one or more of the measurements can be performed by the electronics in the carrier wafer. In a specific, non-limiting example, each of the electronics in the carrier wafer can provide an input voltage to an array of microneedles and measure a response current to directly measure a performance of the array of microneedles after one or more stages of manufacturing.

At block 410, the process 400 includes generating production data for the one or more components at the selected location using the one or more measurements. As discussed above, the production data tracks a development of the one or more components at the selected location, and/or information related to the selected location (e.g., an identification of which wafer the location is on, which region of the wafer the location is positioned in, which machines were used in manufacturing, manufacturing date, and the like).

In some embodiments, the production data includes each of the measurements taken at block 408. In some embodiments, block 410 includes creating one or more aggregates scores from the measurements, and generating the production data based on the aggregate scores. In a specific, non-limiting example, the aggregate score can represent an expected response of the array of microneedles when deployed in a biosensor based on optical measurements of the number of microneedles formed in an array of microneedles, a measurement of the conductivity of the array of microneedles, and a measurement of the chemical response to an analyte of interest of the array of microneedles. Purely by way of example, when an array is missing a microneedle (e.g., that broke off during manufacturing), the aggregate score can be reduced because there is one less sensing structure available. In another example, when the array of microneedles is more conductive than expected (e.g., a thicker conductive layer was deposited than expected), the aggregate score can be increased because a response signal will be communicated more easily.

At optional block 412, the process 400 includes linking the production data to the component(s) at the selected location via their unique identifier. For example, the production data can be stored in the manufacturing database 204 of FIG. 2 and referenced by the unique identifier. Accordingly, another process and/or a user accessing the manufacturing database can later retrieve the production data for any component using that component's unique identifier. For example, the process 800 discussed below with reference to FIG. 8 can retrieve the production data for a component using the component's unique identifier in order to generate calibration adjustments specific to the component. In some embodiments, the process 400 can omit block 412 when the production data is immediately used by another process and/or the user. Purely by way of example, the production data for the measured components may be unnecessary to record when the measurements are destructive to the component(s) at the selected location. In some such embodiments, the process 400 outputs the production data to the process 600 discussed below with respect to FIG. 6 then quits.

In some embodiments, the process 400 is repeated for each component on the wafer to individually generate production data for each of the components. While the repetition of the process can increase the accuracy of the production data linked to each of the components, the repetition can also increase the cost of, and time required for, manufacturing. In some embodiments, the process 400 is not repeated for each component on the wafer. Instead, in some such embodiments, the manufacturing process can include one or more alternative processes for generating production data for additional components on the wafer.

Figure 6:
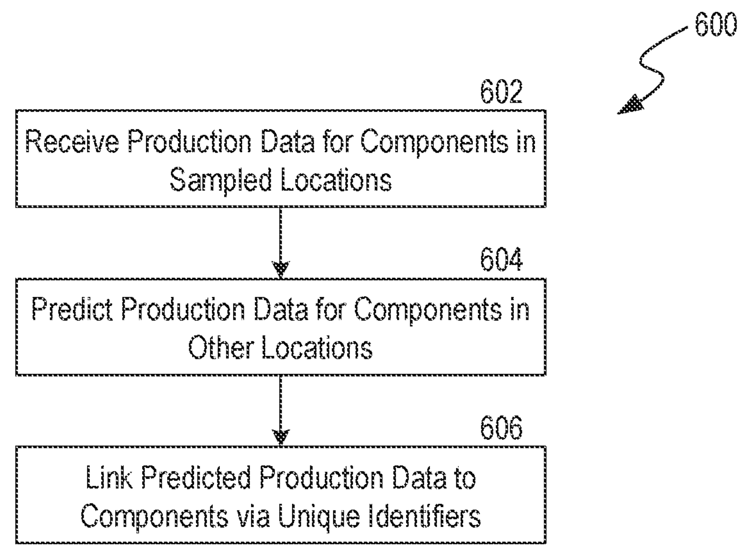
FIG. 6 is a flow diagram of a process for generating production data for additional components on the wafer in accordance with some embodiments of the present technology.

FIG. 6 is a flow diagram of a process 600 for generating the production data for the additional components in accordance with some embodiments of the present technology. Similar to the process 400 discussed above with reference to FIG. 4, it will be understood that the process 600 can be executed by the system 102 discussed above with reference to FIG. 1 and/or in conjunction with any of the modules discussed above with reference to FIG. 2.

The process 600 begins at block 602 by receiving (or retrieving) production data for the component(s) in one or more locations that were selected for measurements during the process 400. In some embodiments, the process 600 receives the production data after the process 400 completes. In some embodiments, the process 600 retrieves the production data after one or more (including all) stages of manufacturing are complete, using the unique identifiers for each of the component(s) in the selected locations.

At block 604, the process 600 includes predicting the production data for the component(s) in other locations in the map of the wafer. Said another way, at block 604, the process 600 includes extrapolating from the production data in the selected locations to generate production data for a portion of (or all) of the other locations on the wafer. In some embodiments, the prediction is based on the relative positions of the selected locations and the remaining locations. Purely by way of example, the selected locations can include a first location in a peripheral region of the wafer and a second location in a central region of the wafer. The process 600 can then predict the production data of a third location in the central region of the wafer. In this example, the prediction can weight the production data for the second location above the production data for the first location since the third location is expected to have development more similar to the second location. Additionally, or alternatively, the process 600 can predict the production data of a fourth location in the peripheral region of the wafer. In this example, the prediction can weight the production data for the first location above the production data for the second location since the fourth location is expected to have development more similar to the first location.

In some embodiments, the prediction includes extrapolations using a weighted average of the production data for the component(s) in the selected locations. In some embodiments, the prediction includes applying an artificial intelligence and/or machine learning model to the production data for the component(s) in the selected locations. In some embodiments, the prediction includes granular predictions of the values that would be obtained if similar measurements were performed for the component(s) in the other locations. In some embodiments, the prediction includes predicting aggregate scores for the component(s) in the other locations.

At optional block 606, the process 600 includes linking the production data to the component(s) at the selected location via their unique identifier. For example, as discussed above, the production data can be stored in the manufacturing database 204 of FIG. 2 and referenced by the unique identifier. Accordingly, another process and/or a user accessing the manufacturing database 204 can later retrieve the production data for any component using that component's unique identifier. In some embodiments, the process 600 can omit block 606 when the production data is immediately used by another process and/or the user. Purely by way of example, the production data may be unnecessary to record when the production data is immediately used to generate calibration adjustments in the process 800 discussed below with respect to FIG. 8. In some such embodiments, the process 400 outputs the production data to the process 800 then quits.

Figure 7:
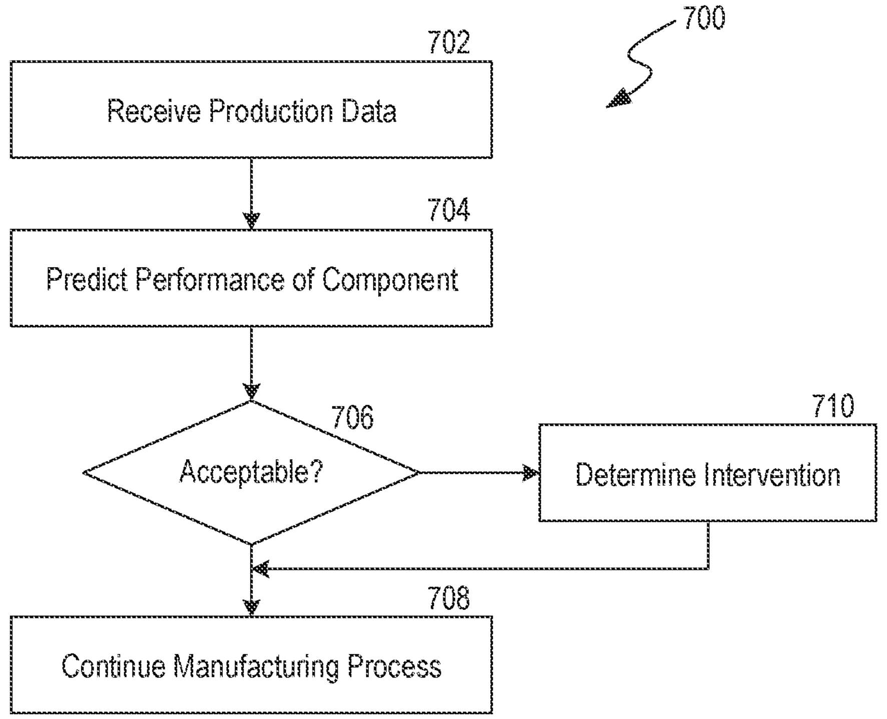
FIG. 7 is a flow diagram of a process for dynamically adjusting manufacturing in accordance with some embodiments of the present technology.

FIG. 7 is a flow diagram of a process 700 for dynamically adjusting manufacturing using the tracked production data in accordance with some embodiments of the present technology. Similar to the processes 400, 600 discussed above, it will be understood that the process 700 can be executed by the system 102 discussed above with reference to FIG. 1 and/or in conjunction with any of the modules discussed above with reference to FIG. 2.

The process 700 begins at block 702 by receiving (or retrieving) production data the component(s) in one or more locations on the wafer that were selected for measurements. In some embodiments, the process 700 receives the production data after the either of the processes 400, 600 complete. In some embodiments, the process 700 retrieves the production data after one or more stages of manufacturing are complete using the unique identifiers for each of the component(s) in a referenced location.

At block 704, the process 700 includes predicting an expected development of the component in later manufacturing stages and/or an expected performance of the component. For example, where the production data includes a measurement of the conductivity of a deposited layer, the process 700 can predict how active the layer will be in further deposition processes to help predict how much material will be deposited. In another specific example, where the production data includes measurements tracking the development of reactive and/or conductive layers on a microsensor component, the process 700 can predict how the microsensor will perform within a biosensor (e.g., a required input voltage to generate detectable signals in response to analytes of interest, a magnitude of signals generated by the microsensor, a sensitivity of the microsensor to analytes of interest, and the like).

In some embodiments, the predictions can be extrapolations from the development of the components so far. In a simple example, where a series of deposition processes has consistently deposited a layer at a certain thickness, the process 700 can extrapolate to predict the growth of the layer in additional deposition processes. In some embodiments, the process 700 includes applying an artificial intelligence and/or machine learning model to the production data for the component(s) in the selected locations to make the predictions at block 704.

At decision block 706, the process 700 checks whether the predicted performance and/or development of the component(s) is acceptable. For example, the process 700 can require that various structures meet or exceed physical specifications. In a specific, non-limiting example, the process 700 can require that various layers of a microsensor have at least a predetermined thickness during manufacturing (e.g., a predetermined thickness of a conductive layer can be set to provide a set resistance and/or help avoid shorts, breakage, and/or other malfunctions). In another example, the process 700 can require that various structures meet or exceed various performance specifications. In a specific, non-limiting example, the process 700 can require that a microsensor is predicted to have a predetermined sensitivity (e.g., a predetermined electro-chemical response) to analytes of interest. The predetermined sensitivity can be based on a desired accuracy and/or granularity of measurements. Additionally, or alternatively, the predetermined sensitivity can be based on limitations from the available sample fluid (e.g., low concentration levels of interstitial fluid in the user's skin, concentration levels of analytes of interest in the interstitial fluid, and the like). If the predicted performance and/or development of the component(s) is acceptable, the process 700 proceeds to block 708, else the process 700 proceeds to block 710.

At block 708, the process 700 includes performing a next stage of manufacturing without any modifications to a manufacturing plan. Purely by way of example, an etching process is satisfactory at decision block 706, the process 700 can include executing a deposition stage to deposit a conductive layer over a plurality of etched microneedles.

Alternatively, at block 710, the process 700 includes determining an intervention to help address a shortcoming in the predicted performance and/or development of the component(s). In some embodiments, the intervention includes one or more additional stages of manufacturing (e.g., an additional deposition stage to increase the thickness of a deposited layer, an additional etching process to remove an unwanted structure, discarding the wafer or portion thereof before completing additional manufacturing stages, and the like).

In some embodiments, the intervention includes one or more alterations to remaining stages of manufacturing (e.g., longer and/or shorter run times on remaining deposition and/or etching stages). For example, when a thickness of a conductive layer is determined to be inadequate (e.g., when a deposition current is lower than expected if the targeted thickness was deposited), the process 700 can determine that an additional deposition stage is necessary to increase the thickness. In some such embodiments, the process 700 includes determining one or more adjustments to the additional stage, or stages, of manufacturing. Returning to the example of an insufficient conductive layer deposition, the process 700 can determine adjustments to the secondary deposition stage tailored to the needed correction (e.g., repeating the deposition stage with an adjusted input voltage, time, of deposition chemistry, etc. to deposit the required amount of material to reach the target thickness). Alternatively, or additionally, the process 700 can identify alterations in future deposition processes such that other layers (e.g., a sensing layer) compensate for the thin conductive layer (e.g., are less reactive to compensate for reduced resistance in the conductive layer). In a non-limiting example, the process 700 can use one or more measurements (or characterizations) of the plating on the electrode tips of an array of microneedles to adjust the time, potential, and/or temperature values for subsequent processing steps, such as deposition steps, etching steps, etc. In this example, if a layer of the plating is less electrochemically active, subsequent electrochemical deposition steps may require a higher temperature, an increased potential, and/or a longer deposition time to achieve a target thickness for a membrane layer, a target morphology, and/or target film characteristics. Each of the adjustments discussed above can help increase the consistency of the manufacturing process, thereby generating more predictable components for biosensors and improving overall consistency.

In some embodiments, the alterations are identified by an artificial intelligence and/or machine learning algorithm trained on past production data. Because the computer algorithms can be trained on large amounts of data, they can identify non-obvious remedies to the identified shortcomings.

In some embodiments, the intervention includes a change in the end product being produced by the manufacturing process. Purely by way of example, working electrodes may need to meet higher standards for predicted performance than counter electrodes and/or reference electrodes. Accordingly, when a batch of electrodes on the wafer do not meet the expectations for a working electrode, the process 700 can shift to producing counter electrodes and/or reference electrodes on the wafer. This change in the end product can require one or more different manufacturing stages (e.g., a chemical-sensing layer can be left off counter electrodes, thereby omitting one or more remaining deposition stages).

In some embodiments, the intervention includes discarding the wafer in the next manufacturing stage, rather than continuing manufacturing, for example when a shortcoming that cannot be corrected is detected. By detecting the incorrectable shortcoming before manufacturing is complete, the process 700 can save costs by skipping other manufacturing stages and/or increase throughput by moving more quickly to the next wafer (e.g., instead of detecting the incorrectable error only after manufacturing is complete). Once the process 700 has determined the intervention(s), the process continues to block 708 to performing the next stage of manufacturing.

The process 700 can be executed after any suitable number of stages of manufacturing. In some embodiments, for example, the process 700 is executed after each stage of manufacturing to ensure that the components are developing according to plan and to reduce the number of wafers that are thrown out due to an unaddressed error during manufacturing. In some embodiments, the process 700 is executed after expected milestones (e.g., after microneedles are structurally formed, after one or more conductive layers are deposited, and the like).

V. Methods for Post-Production Monitoring of Biosensors

In some embodiments, the tracking methods described herein are used for post-production monitoring, updates, and/or recalls of products. As discussed above, each product can be associated with a unique identifier assigned during the manufacturing process. The unique identifier is be linked to production data for the particular product (e.g., data regarding the batch, wafer, wafer location, manufacturing conditions, sensor-level measurements, etc.). Accordingly, even after the product have been deployed, the manufacturer can still monitor product-specific performance, push product-specific updates, and/or issue product-specific recalls, using the identifier. For example, the manufacturer can maintain a computing system (e.g., a cloud-based server) that can communicate with each product (e.g., directly, or indirectly via a corresponding user device). Communications to and/or from a particular product can be tagged, addressed, or otherwise associated with that product's unique identifier so the manufacturer's computing system can track each product individually.

In some embodiments, for example, biosensors and/or users periodically send performance data (e.g., metrics, notifications, errors, etc.) to the computing system so the manufacturer can monitor the post-deployment performance of each product individually. Based on the performance data, the system can determine whether each product is performing properly, identify products that may be malfunctioning, etc. Data from multiple products can be aggregated and analyzed to identify trends, e.g., whether certain batches of biosensors are performing poorly compared to other batches. Optionally, the manufacturer's computing system can identify whether there are any links between product performance and the product's production data, e.g., whether certain performance issues are linked to a particular batch, wafer or wafer location, set of chemicals used, etc. Accordingly, the post-deployment performance data can be used as feedback to modify the manufacturing and/or calibration processes described herein.

Optionally, the manufacturer can use the tracking methods described herein to selectively push post-production updates (e.g., updates to calibration adjustments) to a certain batch of product. For example, if the manufacturer determines that the calibration parameters and/or other operating parameters for a particular group of microsensors should be updated after those microsensors have already been shipped (e.g., based on production data, performance data, shelf life cycles, etc.), the manufacturer's computing system can send the update instructions only to biosensors with microsensors installed that have unique identifiers associated with the targeted group. As another example, the system can send update instructions to all users, but the update instructions can include a set of target unique identifiers such that only product associated with the target unique identifiers implement the update. Accordingly, the present technology allows the manufacturer to selectively update a targeted batch of products (e.g., based on production batch, wafer, wafer location, etc.) without affecting other biosensors and/or components, thus providing highly flexible and customizable post-production adjustments.

The tracking methods described herein can also be used to selectively recall certain products, if appropriate. For example, if the manufacturer determines that a particular batch of microsensors is defective or likely to be defective (e.g., based on production data, performance data, etc.), the manufacturer's computing system can send recall instructions only to biosensors with microsensors having unique identifiers belonging to the defective group. As another example, the system can send recall instructions to all users' biosensors, but the recall instructions can include a specific set of identifiers such that only biosensors with microsensors having those unique identifiers implement the recall instructions. The recall instructions can cause an effected biosensor to enter a locked or otherwise nonfunctional state, such that the biosensor does not operate even if the user attempts to use the biosensor. Alternatively, or in combination, the recall instructions can include an alert transmitted to a user device (e.g., a smartphone) to instruct the user to discard or return the recalled product. Accordingly, the present technology allows the manufacturer to issue recalls in a highly-targeted manner, without affecting biosensors that are operating normally.

In some embodiments, at least some of the biosensors are configured to detect multiple different analytes (e.g., two, three, four, five, or more different analytes), and the manufacturer can use the methods described herein to monitor and/or control product performance with respect to each analyte independently. For example, the performance data transmitted to the manufacturer's computing system can include metrics, notifications, and/or other information for each monitored analyte. Based on the performance data, the system can evaluate whether each product is operating properly for monitoring each analyte and, if appropriate, take corrective action. For example, if the system determines that the product is operating properly when monitoring a first analyte, but is not operating properly when monitoring a second analyte, the system can send an update to the biosensor for the second analyte, such as updated calibration adjustments with updated operating parameters for the second analyte. Alternatively, or in combination, the system can send "recall" instructions for the product with respect to the second analyte, e.g., a biosensor no longer operates to monitor the second analyte, but continues to monitor the first analyte. As previously discussed, the system can analyze aggregated data compiled across multiple biosensors and/or monitored analytes to determine whether there are any correlations between product performance for a particular analyte and the product's production data, e.g., whether issues with monitoring a certain analyte are linked to a particular batch, wafer or wafer location, set of chemicals used, etc. Such analysis can be performed using machine learning techniques and/or other suitable data processing algorithms.

In some embodiments, machine learning techniques and/or other suitable data processing algorithms can be used to correlate collected production and performance data to further improve a resulting accuracy of the biosensors. For example, the techniques disclosed herein can be used to predict performances for the products based on production data (e.g., to predict a magnitude of a response current from a microsensor in the presence of a typical analyte concentration in the interstitial fluid of a user's skin). The machine learning techniques and/or other suitable data processing algorithms can then use the predicted performance to generate adjustments to the operational parameters of a biosensor and/or signal filters (e.g., calibration adjustments) to account for variations in the predicted performance. For example, calibration adjustments can normalize a magnitude of a response current for a given concentration of one or more analytes of interest. As a result, variations in the response current due to variations in the products (e.g., variations in the active area of a microsensor) are reduced (or eliminated). Accordingly, measurements made by the biosensor can be closer to measurements of an actual analyte concentration in the user's skin. In addition, the biosensor can be more sensitive to fluctuations (e.g., because a built-in tolerance for variations from manufacturing can be reduced (or eliminated)).

Additionally, or alternatively, actual performance data can be compared against the predicted performances and the comparison can be studied to identify correlations between production data and the performance data to refine the predictive algorithms and identify particularly useful production data. Purely by way of example, the performance of a biosensor may be correlated to active region characteristics (e.g., active surface area, composition, thickness, number of layers, etc.), manufacturing data (e.g., processing temperatures, gas chemistries, etc.), and/or needle dimensions (e.g., length, shape, etc.). Accordingly, the generation of production data can be adjusted to expand or focus on generating metrics for the identified useful production data. Additionally, or alternatively, the correlations can be used to generate one or more modifications to algorithms for generating calibration adjustments from available production data to increase the efficacy of the calibration adjustments.

Figure 8:
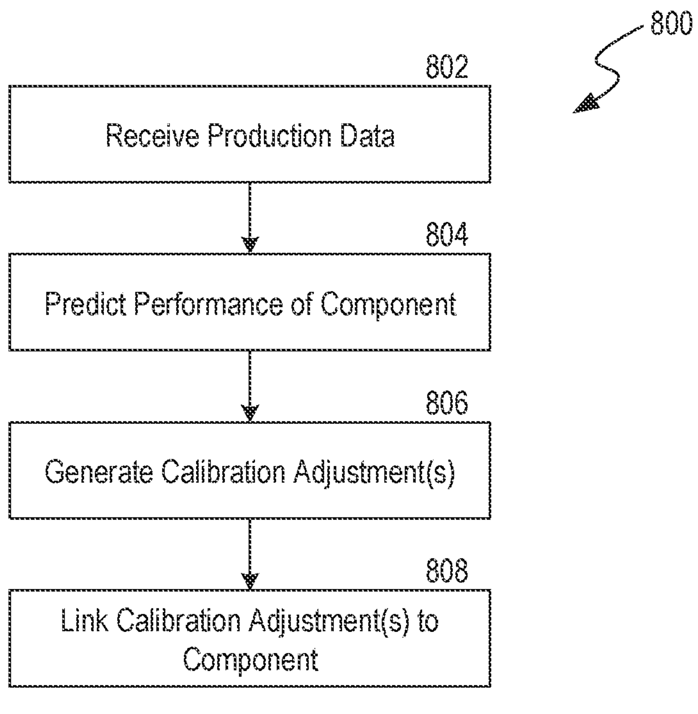
FIG. 8 is a flow diagram of a process for improving the calibration of components manufactured on the wafer in accordance with some embodiments of the present technology.

FIG. 8 is a flow diagram of a process 800 for improving the calibration of components manufactured on the wafer in accordance with some embodiments of the present technology. The process 800 can be executed at least partially by any of the user devices 104 discussed above with reference to FIG. 1.

The process 800 begins at block 802 with receiving production data related to a component on the wafer. In some embodiments, the production data is received in raw form after it is linked to the unique identifier at block 412 of FIG. 4 or block 606 of FIG. 6. In some embodiments, the production data is received from a storage component in response to a prompt using the unique identifier. In some embodiments, the process 800 is specific to a single component on the wafer, such that the production data is received for the single component. In other embodiments, the process 800 is general between multiple components (e.g., when the unique identifier is associated with a region and/or location on the wafer with more than one component, when the unique identifier is associated with the wafer in general, and the like).

At block 804, the process 800 includes predicting one or more performance metric(s) of the component using the production data. Purely by way of example, the production data can include metrics related to an electrochemical response of an electrode. In this example, the prediction can include a prediction of various parameters of signals that the electrode will generate when exposed to one or more analytes of interest with a predetermined bias, such as a magnitude, frequency, waveform, and the like. In another example, the production data can include metrics related to the growth and development of microneedles on the component. In this example, the prediction can include a prediction of a depth that the microneedles will access when applied to a user's skin with a predetermined force.

Each of the performance metrics predicted at block 804 can be at least partially dependent on an adjustable input variable. For example, the predicted parameters of signals are partially dependent on parameters of the input bias (e.g., the magnitude, frequency, and/or waveform of an input voltage), and the depth that the microneedles will access is at least partially dependent on the application force.

Thus, the predicted performance metrics can be adjusted via changes to the input variable(s). Accordingly, at block 806, the process 800 includes generating one or more calibration adjustments. The calibration adjustments are changes to the input variable(s) that bring the predicted performance metrics within a predetermined acceptable range. Purely by way of example, the calibration adjustments can include raising (or lowering) the magnitude of an input voltage to increase (or decrease) the electrode's predicted response to analytes of interest. Said another way, the calibration adjustment(s) help normalize the predicted performance metrics, thereby reducing variability in the performance of the components once deployed in a biosensor and increasing the accuracy and/or consistency of the measurements from the biosensor.

Purely by way of example, the production data can measure characteristics related to a signal strength expected from a microsensor when deployed and reacting to one or more analytes of interest (e.g., an active area of the microsensor, an electrical resistance in conductive layers, a chemical reactivity of a sensing layer, and the like). This production data can be used to generate a prediction of the expected signal strength when the microsensor is deployed (e.g., a magnitude of a response current in the presence of a range of expected analyte concentrations). The predicted performance can then be used to adjust operational parameters that effect the predicted performance (e.g., a magnitude, waveform, and/or frequency of an input bias such as an input voltage) and/or adjust signal filters. The calibration adjustments can help normalize the actual signal received from the microsensor, thereby helping the biosensor provide a more accurate measurement of the analytes of interest. In a specific, non-limiting example, the production data can measure the active area of an array of microneedles (e.g., using optical measurements) and/or electrochemical responses of the array of microneedles. The measurements can be used to predict a magnitude of a response current that will be received from the array of microneedles in the presence of one or more analytes of interest. Where the predicted magnitude is relatively low compared to a predetermined normal (e.g., because of a relatively small active area, for example resulting from one or more microneedles broken off), the calibration adjustments can increase a magnitude of an input voltage and/or apply a boosting filter to account for the relatively low response.

In some embodiments, calibration adjustments can be generally proportional to divergence from an expected value in the performance data. For example, increases or decreases in surface area of the electrode (e.g., microneedle tips), due to variation in the electrode formation (e.g., tip geometry and/or missing microneedle tip(s)) can be used to update the calibration adjustments. Returning to the specific example above, the production data can indicate that the active area of the sensor is 80 percent of an expected value (e.g., of a mean after production). In this example, the calibration adjustments can include a signal filter that boosts the signal by 25 percent, thereby returning to about 100 percent of the expected signal strength. In another example, variation in electrode resistance and/or other electrical characteristics can be used to update the calibration adjustments (e.g., to update and/or adjust a poise potential applied to a microsensor during operation of the biosensor to account for the different electrical characteristics). In yet another example, variation in membranes used for selectivity and formed during manufacturing (e.g., in the sensing layers of microneedles) can be used to update confidence intervals of the determinations made based on signals from the microsensor (e.g., confidence intervals in blood-glucose level estimates can be adjusted based on the probability of an interfering species that is affected by variation in the membranes). Similarly, variation in the thickness of membranes can be used to alter and/or adjust models that predict diffusion behavior of different species within an enzyme matrix, between layers, and/or to the electrode surface. This can be used to update calibration adjustments such as gain settings, baseline offsets, and/or smoothing parameters to account for different levels of noise and/or frequency characteristics of the noise.

In some embodiments, the calibration adjustments are generated by an artificial intelligence and/or machine learning model trained to handle a variety of variations in the performance data. For example, the computer models can help account for variations in different directions (e.g., an increase in active surface area for a microsensor, a reduction in resistance in a conductive layer, and an increase in reactivity in a sensing layer).

At block 808, the process 800 includes linking the calibration adjustments to the components using the unique identifier. In doing so, the process 800 allows the precise measurements and tracking performed during manufacturing to generate calibration adjustments that can be easily retrieved when the components are deployed into a biosensor, as explained in more detail below with respect to FIG. 8.

Figure 9:
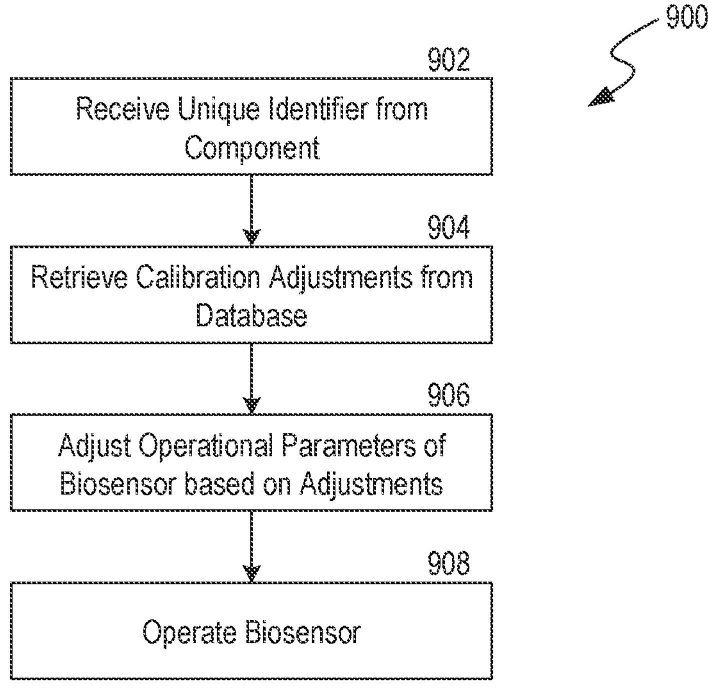
FIG. 9 is a flow diagram of a process for calibrating a biosensor to using the calibration adjustment(s) generated by the process of FIG. 8 in accordance with some embodiments of the present technology.

FIG. 9 is a flow diagram of a process 900 for calibrating a biosensor to using the calibration adjustment(s) generated by the process 800 of FIG. 8 in accordance with some embodiments of the present technology. The process 900 can be at least partially executed by a biosensor and/or a user device (e.g., a smartphone) in communication with the biosensor each time a new component (e.g., a new patch) is loaded onto the biosensor.

The process 900 begins at block 902 by receiving at least one unique identifier from a component of a biosensor and/or from a unique biosensor itself. In various embodiments, the unique identifier can be received via wireless communication (e.g., shortwave radio communication such as Bluetooth®) with the biosensor as the component is installed and/or the biosensor is activated; via user input (e.g., after reading the unique identifier off packaging associated with the component and/or the biosensor); via a radio-frequency identification (RFID) chip associated with the component and/or the biosensor; via a scannable code (e.g., a bar code, a QR code, and the like) on the component, biosensor, and/or related packaging; and/or via any other suitable means.

In some embodiments, at block 902, the process 900 includes receiving multiple unique identifiers. For example, the process 900 can include receiving a first unique identifier associated with a working electrode in a patch being installed in the biosensor and a second unique identifier associated with a reference electrode in the patch. In another example, the process 900 can include receiving a first unique identifier associated with a specific working electrode and a second unique identifier associated with the wafer on which the patch was manufactured.

At block 904, the process 900 includes retrieving one or more calibration adjustments from a database (e.g., the manufacturing database 204 discussed above with reference to FIG. 2) using the one or more unique identifiers. That is, as discussed above, the unique identifiers allow the process 900 to retrieve calibration adjustments specific to one or more components of the biosensor based on production data specific to each of the one or more components. Said another way, the unique identifiers provide the process 900 with a specific address or reference to retrieve calibration adjustment(s) specific to the operating components of the biosensor.

At block 906, the process 900 includes adjusting one or more operational parameters of the biosensor based on the retrieved calibration adjustment(s). In various embodiments, the adjustments to the operational parameters can include adjustments to an input bias, such as changes to a magnitude, frequency, and/or waveform of an biasing voltage and/or current; adjustments to the operation of a counting electrode; adjustments to an application force necessary to apply to the biosensor to the user's skin; adjustments to a dynamic biasing input bias to account for predicted sensor drift; adjustments to a sampling frequency for one or more electrodes in the biosensor; adjustments to filters applied to signals generated by the biosensor; variances in a calibration routine performed after the biosensor is applied to the user's skin (e.g., variances in a calibrating fluid released, input pulsing routine, and the like); and/or various other suitable adjustments that impact measurements obtained from the biosensor.

At block 908, the process 900 includes operating the biosensor using the adjusted operational parameters. Because each of the adjustments to the operational parameters is specific to the operating components of the biosensor, they can improve the accuracy of the measurements obtained from signals generated by the biosensor. As a result, the process 900 can also help increase the accuracy of determinations about various health attributes made using the measurements performed by the biosensor.

Figure 10:
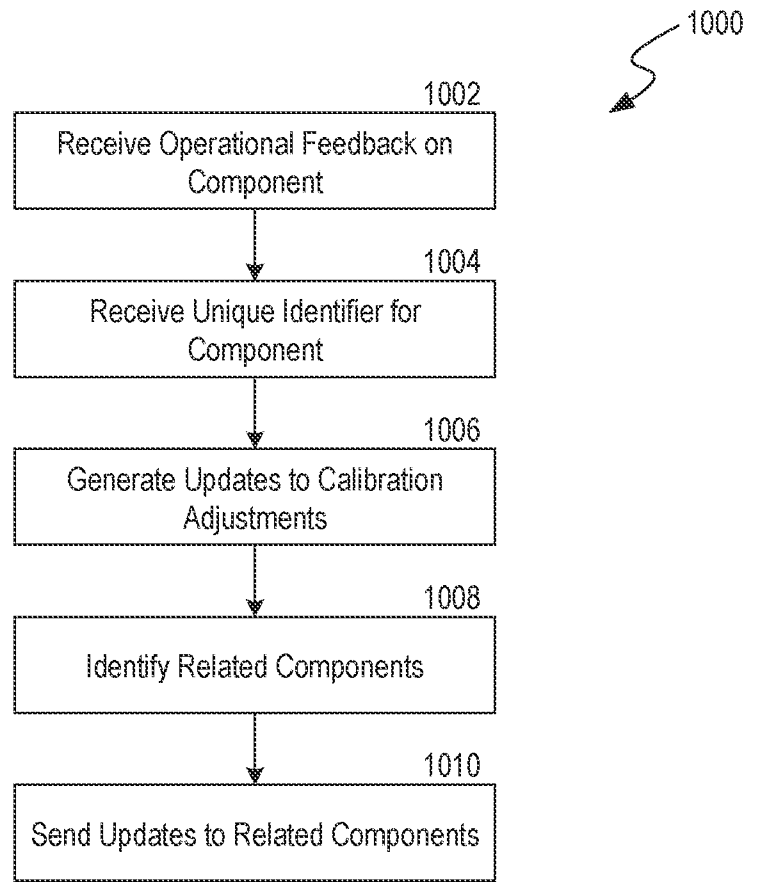
FIG. 10 is a flow diagram of a process for using feedback related to one component to update calibration adjustments in accordance with some embodiments of the present technology.

FIG. 10 is a flow diagram of a process 1000 for using feedback related to one component to update calibration adjustments for related components. For example, the process 1000 can be used to update the calibration adjustments for working electrodes manufactured on the same wafer, or in the same region of a wafer, based on observations related one of the electrodes deployed in an active biosensor.

The process 1000 begins at block 1002 with receiving operational feedback (e.g., actual performance data) related to a first component and/or biosensor. In some embodiments, the feedback can be received from a user of the biosensor based on their experience with the biosensor and/or additional data they have on a health parameter the biosensor is used to monitor. Purely by way of example, the biosensor can be a continuous glucose monitor deployed to monitor the user's blood glucose levels using analytes detected in the presence of the user's interstitial fluid. In this example, the user may periodically perform a secondary blood glucose measurement (e.g., using a traditional blood sample method) to confirm the accuracy of the measurements from the biosensor. At block 1002, the process 1000 can include receiving feedback related to a difference between the additional blood glucose measurements and the measurements performed by the biosensor (e.g., an indication that the measurements are accurate and/or inaccurate).

When the measurements are inaccurate, the feedback can indicate that the calibration adjustments need one or more updates to improve the accuracy of the measurements from the biosensor. Further, the required updates can be common between components manufactured on the same region of a wafer, manufactured on the same wafer, and/or manufactured under similar conditions.

At block 1004, the process 1000 includes receiving one or more unique identifiers associated with the biosensor and/or the operating components of the biosensor. In various embodiments, the unique identifier(s) can be received through any of the mechanisms discussed above with reference to block 902 of FIG. 9. For example, the unique identifier(s) can be received via wireless communication with the biosensor.

At block 1006, the process 1000 includes generating updates to the calibration adjustments based on the received operational feedback. For example, where the operational feedback indicates that the signals generated by the biosensor are indicating lower blood glucose levels than are measured by the secondary means, the process 1000 can include generating updates to the input bias applied to a working electrode in the biosensor and/or processing filters applied to the generated signals. As a result, the updates to the calibration adjustments can improve the accuracy of the measurements obtained from the biosensor in question.

In some embodiments, the updates to the calibration adjustments include updates to a confidence score for the accuracy of the biosensor based on the performance data and/or a comparison of measurement data from the biosensors and measurement data from the alternative sources (e.g., traditional blood sampling methods). In some embodiments, the confidence score indicates a range of values associated with an analyte of interest. For example, the confidence score can provide a range of blood-glucose levels surrounding the biosensor's measurement, where the user's actual blood-glucose level is likely to be within the range. In some embodiments, the confidence score can indicate that the user should only use the measurements from the biosensor to track trends and/or to receive a measurement data from the alternative sources before relying on the measurements to take a clinical action (e.g., dosing insulin).

In some embodiments, the process 1000 can also refine a calibration algorithm and/or a performance prediction algorithm used to generate the calibration adjustments based on the performance data. For example, where performance data consistently indicates that components of a biosensor are more sensitive than predicted by the calibration adjustments associated with the components, the process 1000 can refine the process 800 discussed above with reference to FIG. 8 to predict higher sensitivity at block 804 and/or to refine the calibration adjustments generated at block 806.

At block 1008, the process 1000 includes identifying one or more additional components related to the component(s) associated with the received unique identifier. In some embodiments, the additional components are also associated with the received unique identifier (e.g., because they were manufactured on the same wafer and/or in the same location and/or region of the wafer), allowing the process 1000 to identify the additional components directly. In some embodiments, the process 1000 identifies the additional components by (1) identifying a wafer and/or one or more locations on the wafer associated with the received unique identifier, then (2) identifying other components associated with the wafer and/or locations on the wafer (e.g., based on a map of the wafer, related unique identifiers, and the like). In some such embodiments, the process 1000 includes retrieving one or more unique identifiers associated with each of the identified additional components.

At block 1010, the process 1000 includes sending the updates to the calibration adjustments to update the calibration adjustments for each of the additional components identified as related. In some embodiments, the updates are sent to a central database (e.g., the manufacturing database 204 discussed above with reference to FIG. 2). In some embodiments, the updates are sent directly to a user device and/or biosensor that has accessed the calibration adjustments for the additional components (e.g., a user device associated with a second component deployed in a second biosensor).

Further, in some embodiments, the updates to the calibration adjustments are sent to a manufacturing database (e.g., the manufacturing database 204 discussed above with reference to FIG. 2) to help update a process of generating the calibration adjustments. For example, consistent updates can reflect a need to adjust the predictions of performance metrics made at block 904 of FIG. 9, thereby also adjusting the generation of the calibration adjustments at block 906.

It will be understood that, in various embodiments, the process 1000 executes the steps in blocks 1002-1010 in a different order. Purely by way of example, the process can execute block 1006 to identify updates to the calibration adjustments (e.g., using locally saved calibration adjustments) before executing block 1004 to receive a unique identifier associated with one or more components in the biosensor and/or before executing block 1008 to identify related components. In another example, the process 1000 can execute block 1008 to identify related components before executing block 1006 to identify updates to the calibration adjustments.

Figure 11:
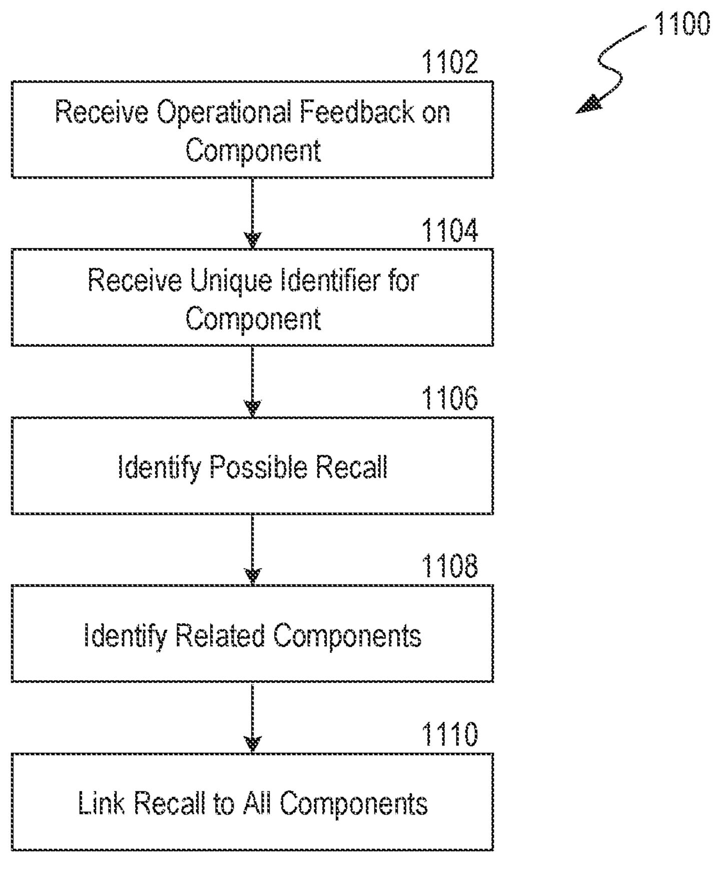
FIG. 11 is a flow diagram of a process for identifying a necessary recall of one or more components of a biosensor in accordance with some embodiments of the present technology.

FIG. 11 is a flow diagram of process 1100 for communicating a recall of one or more components of a biosensor in accordance with some embodiments of the present technology. For example, the process 1100 can be used to identify potentially malfunctioning and/or inadequate electrodes based on the failure of another electrode manufactured on the same wafer and/or in the same region of a wafer.

Similar to the process 1000 discussed above with reference to FIG. 10, the process 1100 begins at block 1102 with receiving operational feedback (e.g., actual performance data) related to a first component and/or biosensor. In some embodiments, the feedback can be received from a user of the biosensor based on their experience with the biosensor and/or additional data they have on a health parameter the biosensor is used to monitor. Purely by way of example, the biosensor can be a continuous glucose monitor deployed to monitor the user's blood glucose levels using analytes detected in the presence of the user's interstitial fluid. In this example, the user may periodically perform a secondary blood glucose measurement (e.g., using a traditional blood sample method) to confirm the accuracy of the measurements from the biosensor. At block 1102, the process 1100 can include receiving feedback related to a difference between the additional blood glucose measurements and the measurements performed by the biosensor, such as an indication that the measurements are inaccurate. When the measurements are inaccurate, the feedback can indicate that the biosensor and/or operational components of the biosensor are operating at an unacceptable level of inaccuracy.

The unacceptable level of inaccuracy can be set by a user (e.g., as an "accuracy setting"), a biomonitoring system (e.g., biomonitoring system 102 of FIG. 1), or systems or components disclosed herein. For example, the user can periodically perform alternative analyte-measuring tests (e.g., lab tests; blood-based tests such as tradition blood-glucose meters, tests from other biosensors; predictive algorithm results; and the like) to compare results from the calibration tests to data generated by the sensor. In some embodiments, the accuracy setting can be a percentage (e.g., 20%, 10%, 5%, 2%, 1%, etc.) within reference data from the alternative analyte-measuring test. An accuracy setting can be inputted and/or adjusted based on the health conditions and parameters to be managed, such as Type I diabetes, Type II diabetes, etc., and can include maximum/maximum values of absolute deviation of data, mean absolute relative deviation of data, etc. Statistical analysis can be used to determine indications of accuracy and can include linear regression models of biosensor data to reference data (e.g., comparator analyte values, lab data, etc.). One or more accuracy settings can be associated with each analyte, health state, or other user profile.

In some embodiments, the operational feedback is received directly from the biosensor (e.g., when one or more components do not respond to an input). Purely by way of example, the operational feedback can include an indication that an electrode in a patch is not responding to an input voltage at all, indicating an electrical problem in the electrode and/or in the patch.

At block 1104, the process 1100 includes receiving one or more unique identifiers associated with the biosensor and/or the operating components of the biosensor. In various embodiments, the unique identifier(s) can be received through any of the mechanisms discussed above with reference to block 902 of FIG. 9. For example, the unique identifier(s) can be received via wireless communication with the biosensor.

At block 1106, the process 1100 includes identifying a possible recall based on the received operational feedback. For example, where the operational feedback indicates that the operating components are malfunctioning (e.g., not responding to input biases and/or resulting unusable signals), the process 1100 can determine that the components are not suitable for use in the biosensor. As a result, the process 1100 can identify the malfunctioning of the components to the user and/or prevent the biosensor from operating with the malfunctioning components. Additionally, or alternatively, the process can evaluate the malfunction to determine whether the malfunction is likely due to an isolated error in the components (e.g., from damage after manufacturing, improper installation, and the like) or a possible error in manufacturing. When the problem cannot be attributed to an isolated error, the process 1100 identifies a possible recall. The possible recall can then be reviewed and/or confirmed by another process or party (e.g., reviewed by the manufacturer).

At block 1108, the process 1100 includes identifying other components related to the malfunctioning components. For example, the related components can be identified using the unique identifier for the malfunctioning component to identify the wafer, region of the wafer, position on the wafer, date of manufacturing, equipment used in manufacturing, and the like, and identifying other components with related data. As a result, the related components can include other components manufactured in the same location on the wafer, in the same region on the wafer, from the same wafer, otherwise manufactured in a bulk process, manufactured on the same day, and/or manufactured using the same equipment. Each of these components can be likely to have a similar malfunction, thereby making them unsuitable for use.

At block 1110, the process 1100 includes liking recall information to each of the related components identified at block 1108 using their respective unique identifiers. Accordingly, the recall information is stored in an accessible database (e.g., the manufacturing database 204 of FIG. 2), such that the components can be identified before a sale and/or before use within a biosensor. For example, when a user installs a related component into their device to begin the process 900 discussed above with respect to FIG. 9, they will be prompted with the recall information.

In some embodiments, the recall information includes a warning regarding the identified malfunction to alert the user of a potential flaw in the components. In some embodiments, the recall information instructs the user not to rely on or deploy the components in the biosensor. In some embodiments, the recall information is automatically transmitted to the biosensor to prevent the biosensor from operating with the recalled components. As a result, the recall information can help prevent a user from accidentally (or intentionally) deploying and/or relying on the recalled components.

Figure 12:
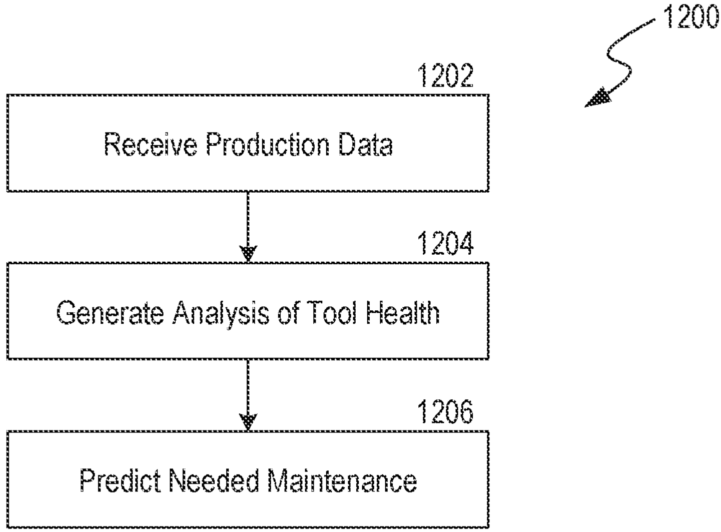
FIG. 12 is a flow diagram of a process for tracking the health of manufacturing tools used in the production of the components of the biosensor in accordance with some embodiments of the present technology.

FIG. 12 is a flow diagram of a process 1200 for tracking the health of manufacturing tools used in the production of the components of the biosensor in accordance with some embodiments of the present technology. The process 1200 can be executed by any module with access to the manufacturing database 204 discussed above with respect to FIG. 2 and/or that receives data from any of the equipment monitoring modules 226*a*-N.

The process 1200 begins at block 1202 with receiving (or retrieving) production data associated with a manufacturing tool. For example, the production data can include various in-line metrics that help track a milage for the tool (e.g., the amount of work the tool has performed, the number of manufacturing cycles the tool has undergone, the operational time for the tool, and the like). Additionally, or alternatively, the production data can include measurements of component(s) after being processed by the tool and/or direct measurements of the tool itself (e.g., optical measurements).

At block 1204, the process 1200 includes generating an analysis of the tool health. In a simple example, when the measurements of a component conform to expectations after a manufacturing stage in a specific manufacturing tool, the measurements can indicate that the tool is generally healthy and/or does not need maintenance. In contrast, when the measurements do not conform to expectations, the measurements can indicate that the tool will need maintenance soon (or needs maintenance). In a more complicated example, the process 1200 can include inputting the relevant production data into an artificial intelligence and/or machine learning model that relates the production data to analyze tool health in advance of any needed maintenance.

At block 1204, the process 1200 includes predicting needed maintenance for the tool. The prediction can include a prediction of when the maintenance will be needed (e.g., how many cycles of manufacturing before the tool will need maintenance) and/or what maintenance will be needed (e.g., a prediction of parts that will need servicing and/or replacement). A frequent and/or early assessment of the tool health can help plan around necessary tool maintenance to reduce (or avoid) down time in production; reduce (or eliminate) the variation in components manufactured on the tool; and/or reduce (or eliminate) the number of components thrown out (or needing further processing) due to tool malfunctions. Accordingly, the analysis of the tool health and predictions for needed maintenance can help increase throughput of related manufacturing processes, reduce variance in resulting components, and/or reduce the cost per component.

VI. Example Biosensor Patch and Needles

Figures 13A, 13B:
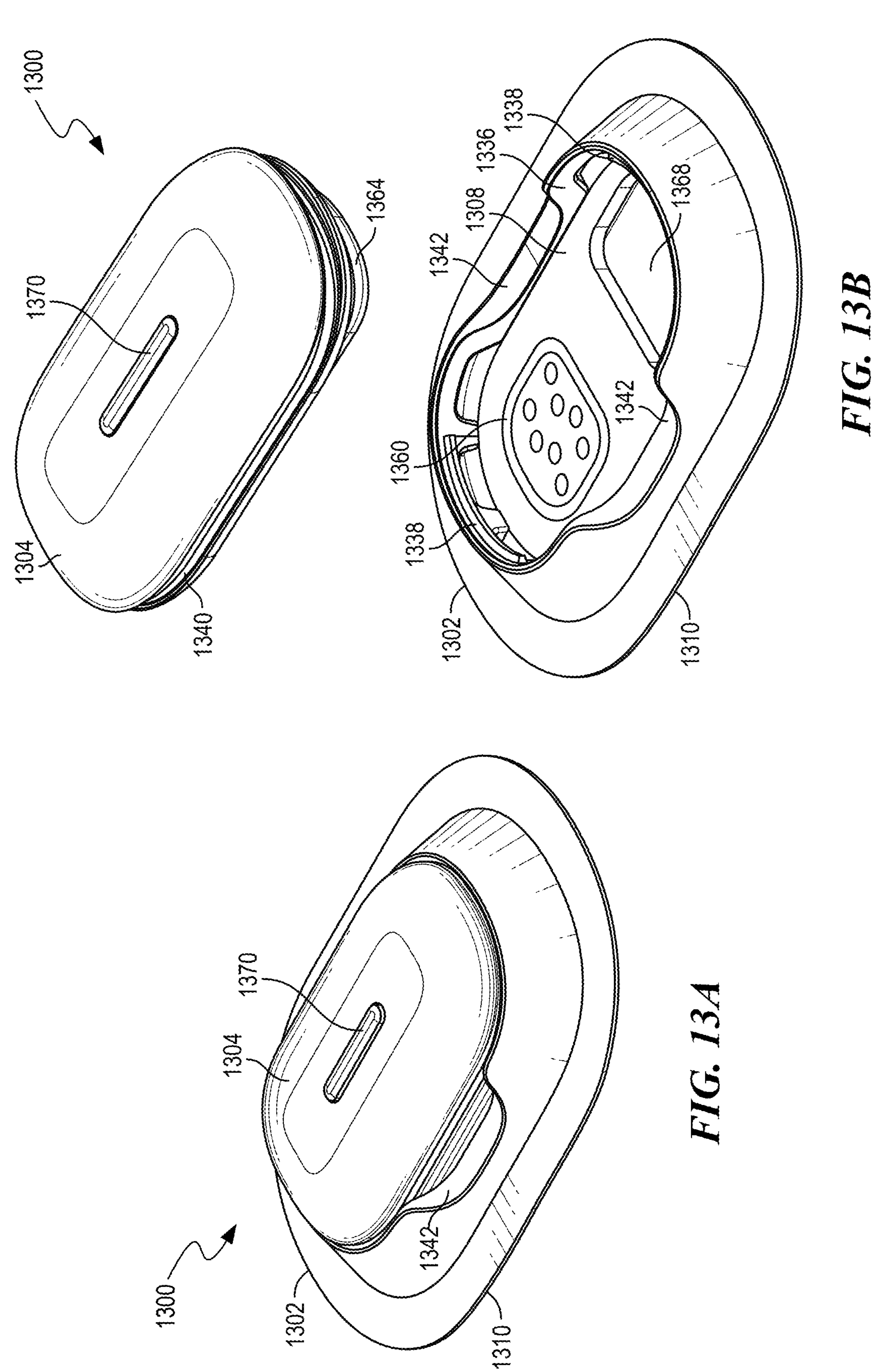
FIGS. 13A-13E are illustrations of a representative example of a biosensor patch device configured in accordance with some embodiments of the present technology.
Figures 13C, 13D:
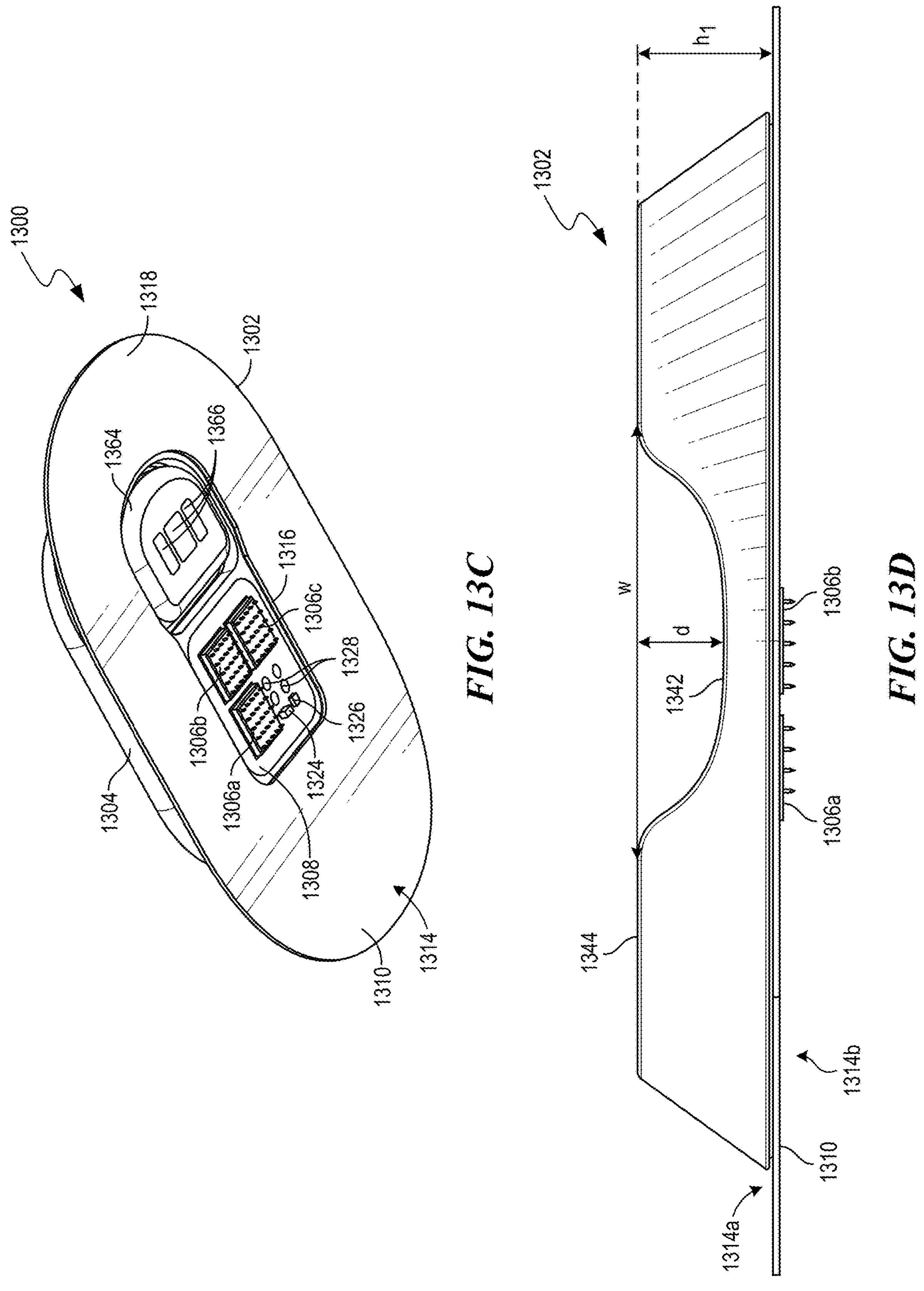
Figure 13E:
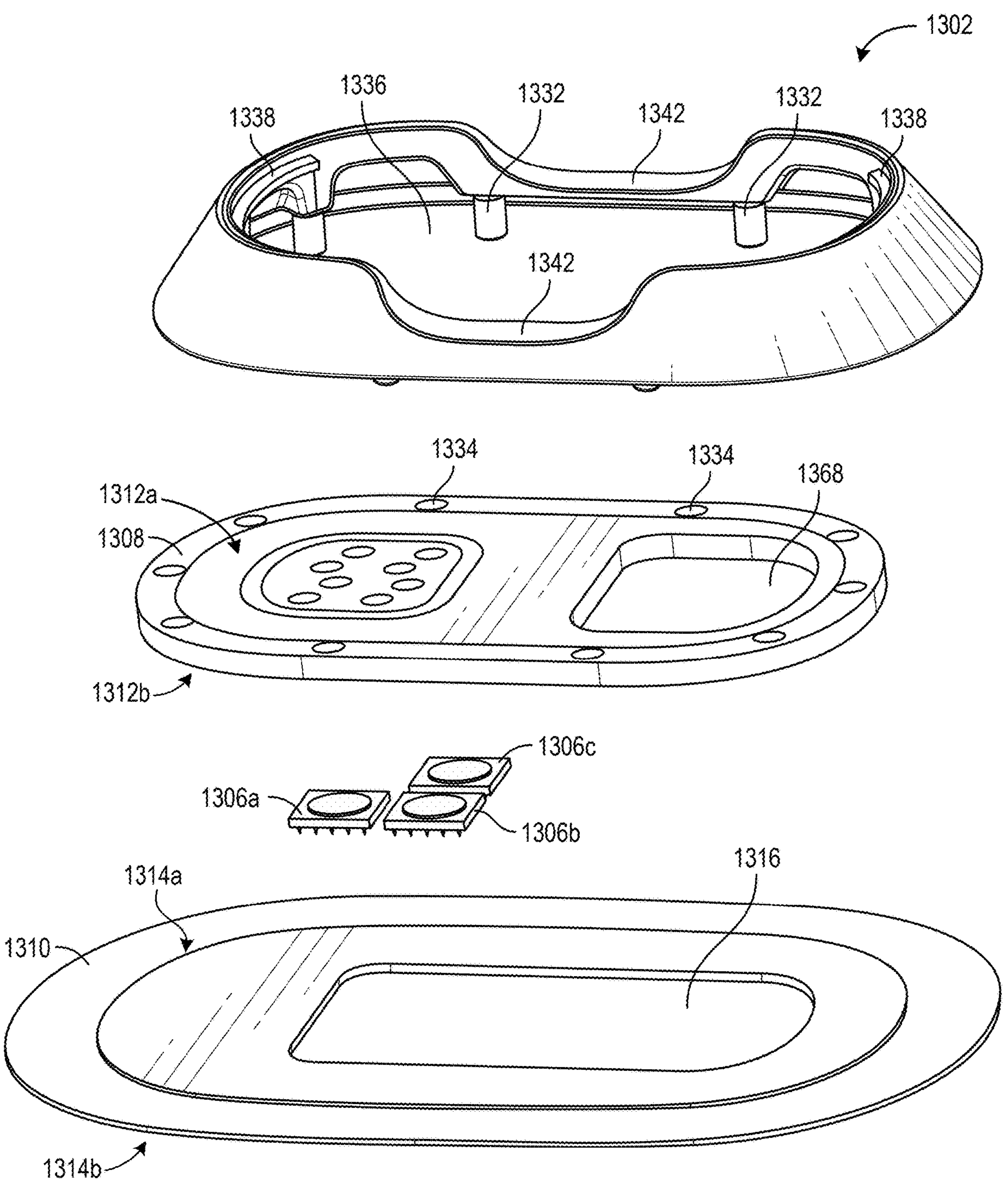

FIGS. 13A-13D illustrate a representative example of a biosensor device 1300 ("device 1300") configured in accordance with some embodiments of the present technology. Specifically, FIGS. 13A-13C illustrate the overall device 1300, FIGS. 13D and 13E illustrate a patch portion 1302 ("patch 1302," sometimes also referred to herein as a "microsensor patch" and/or a "disposable patch") of the device 1300. The description of the biosensor device 104*a* (FIG. 1), the biosensor 242 (FIG. 2), and devices 300 of FIGS. 3A-3C applies equally to the biosensor device 1300, and the biosensor device 1300 can include one or more products from the methods discussed with respect to FIGS. 4-12.

Referring first to FIG. 13A (top perspective view), 13B (exploded view), and 13C (bottom perspective view) together, the device 1300 is configured as a wearable sensor for application to the user's body. The device 1300 includes a patch 1302 for mounting to the skin, and a pod 304 that interfaces with the patch 1302. The patch 1302 and pod 1304 can be discrete components that are releasably connected to each other to form the device 1300 (FIGS. 13A and 13C show the device 1300 when assembled, and FIG. 13B shows the device 1300 when the patch 1302 and the pod 1304 are separated). As previously discussed, the patch 1302 can be a disposable component intended for short-term use, while the pod 1304 can be a reusable component intended for longer-term use with multiple different patches 1302.

The device 1300 can be configured to be worn by the user over an extended period of time in order to generate measurements of any of the health parameters described herein, such as analyte levels (e.g., concentrations of glucose, gases, electrolytes, BUN, creatinine, ketones, cholesterol, triglycerides, alcohols, amino acids, neurotransmitters, hormones, disease biomarkers, drugs, etc.), physiological information (e.g., heart rate, body temperature, blood oxygenation, blood pressure, respiratory rate, bioimpedance, activity levels, sleep data), etc. In some embodiments, the device 1300 includes a plurality of different sensor types for measuring multiple health parameters. For example, the device 1300 can include at least two, three, four, five, or more different sensor types. The sensors can be located in the patch 1302, pod 1304, or any suitable combination thereof.

FIG. 13D is a side view of the patch 1302, and FIG. 13E is an exploded view of the patch 1302. Referring next to FIGS. 13B-3E together, the patch 1302 is configured to temporarily attach to the user's body, such as on the skin of the user's hand, arm, shoulder, leg, foot, chest, back, neck, etc. The patch 1302 can include one or more sensors that generate signals indicative of analyte levels, physiological parameters, and/or other health parameters associated with the user's skin. As best seen in FIG. 13C, the patch 1302 can include a set of microneedle arrays 1306*a*-*c* configured to penetrate into the user's skin (e.g., into the epidermis). The microneedle arrays 1306*a*-*c* can incorporate any of the features described above with respect to the microneedles 308 of FIG. 3.

In the illustrated embodiment, the patch 1302 includes three microneedle arrays 1306*a*-*c*, each including 25 microneedles arranged in a 5×5 grid. The microneedle arrays 1306*a*-*c* can be configured to detect one or more analytes in the interstitial fluid of the epidermis, e.g., using electrochemical techniques. For example, the microneedle array 1306*a* can be configured as a first working electrode for detecting a first set of analytes (e.g., glucose), the microneedle array 1306*b* can be configured as a reference electrode, and the microneedle array 1306*c* can be configured as a counter electrode. In other embodiments, however, the patch 1302 can include fewer or more microneedle arrays 1306*a-c*, and/or the configuration of each microneedle array 1306*a-c* (e.g., geometry, number of microneedles, detected analyte, etc.) can be varied as desired. For example, the patch 1302 can include four microneedle arrays, with two arrays configured as working electrodes, one array configured as a reference electrode, and one array configured as a counter electrode.

Optionally, some or all of the microneedle arrays 1306*a-c* can alternatively or additionally detect other parameters besides analyte concentration, such as bioimpedance, biopotential, etc. For example, bioimpedance can be used to assess various physiological parameters, such as respiration rate, body composition, and/or hydration. Additionally, bioimpedance measurements of individual microneedles and/or microneedle arrays 1306*a-c* can be used to measure or estimate microneedle penetration into the skin (e.g., whether the microneedle arrays 1306*a-c* are in proper contact with the skin, the percentage of microneedles in each array that are in proper contact with the skin, etc.). The amount of microneedle penetration can be used to adjust downstream signal processing performed by the device 1300, such as selecting correction factors for signal processing algorithms, selecting the algorithms to be used, selecting subsets of data to be used or excluded, etc.

As best seen in FIG. 13E, the patch 1302 can include an electronics substrate 1308 (e.g., a printed circuit board (PCB), a flex circuit, etc.) and a mounting substrate 1310 (e.g., an adhesive film, sticker, tape, etc.) that collectively support the microneedle arrays 1306*a-c* and couple to the user's body. The electronics substrate 1308 can be a flattened, oval-shaped structure having an upper surface 1312*a* and a lower surface 1312*b*, and the mounting substrate 1310 can also be a flattened, oval-shaped structure having an upper surface 1314*a* and a lower surface 1314*b*. In other embodiments, the electronics substrate 1308 and mounting substrate 1310 can each independently have a different shape (e.g., circular, square, rectangular, etc.). Additionally, although the mounting substrate 1310 is illustrated as being larger than the electronics substrate 1308 (e.g., with respect to length, width, perimeter, etc.), in other embodiments, the mounting substrate 1310 can be the same size as the electronics substrate 1308 or can be smaller than the electronics substrate 1308. Moreover, in other embodiments, the electronics substrate 1308 and mounting substrate 1310 can be combined into a single, unitary component, rather than being two discrete components that are connected to each other to assemble the patch 1302.

The microneedle arrays 1306*a-c* can be coupled to the lower surface 1312*b* of the electronics substrate 1308. The mounting substrate 1310 can include an aperture 1316 configured such that, when the lower surface 1312*b* of the electronics substrate 1308 is attached to the upper surface 1314*a* of the mounting substrate 1310, the microneedle arrays 1306*a-c* pass through the aperture 1316 and extend past the lower surface 1314*b* of the mounting substrate 1310 in order to access the user's skin (best seen in FIGS. 13C and 13D). Optionally, the aperture 1316 of the mounting substrate 1310 can be larger than the surface area of the microneedle arrays 1306*a-c* so that one or more additional sensors can extend through the mounting substrate 1310 to access the skin, as described further below.

Referring to FIG. 13C, the mounting substrate 1310 can be configured to temporarily secure the patch 1302 (as well as the rest of the device 1300) to the user's skin. For example, the lower surface 1314*b* of the mounting substrate 1310 can include an adhesive region 1318 configured to temporarily attach to the user's skin. The adhesive region 1318 can extend across the entirety of the lower surface 1314*b*, or at least portions thereof. In the illustrated embodiment, the microneedle arrays 1306*a-c* are located at the central portion of the mounting substrate 1310, such that the adhesive region 1318 completely surrounds the microneedle arrays 1306*a-c* to maintain the microneedle arrays 1306*a-c* in close contact with the skin. In other embodiments, however, the microneedle arrays 1306*a-c* and/or adhesive region 1318 can be arranged differently, e.g., the microneedle arrays 1306*a-c* can be offset to one side of the mounting substrate 1310, the adhesive region 1318 can surround only a portion of the microneedle arrays 1306*a-c*, etc. The adhesive region 1318 can be made of any suitable material suitable for coupling to the skin for an extended time period (e.g., at least 12 hours, 24 hours, 2 days, 3 days, 4 days, 5 days, 6 days, 1 week, etc.). The material of the adhesive region 1318 can also be biocompatible, breathable, and/or water-resistant, e.g., to reduce discomfort and/or avoid premature detachment. Additionally, the mounting substrate 1310 itself can be a flexible component configured to conform the user's body to further improve adhesion and user comfort.

VII. Example Wafer-Wafer Processing

Figure 14A:
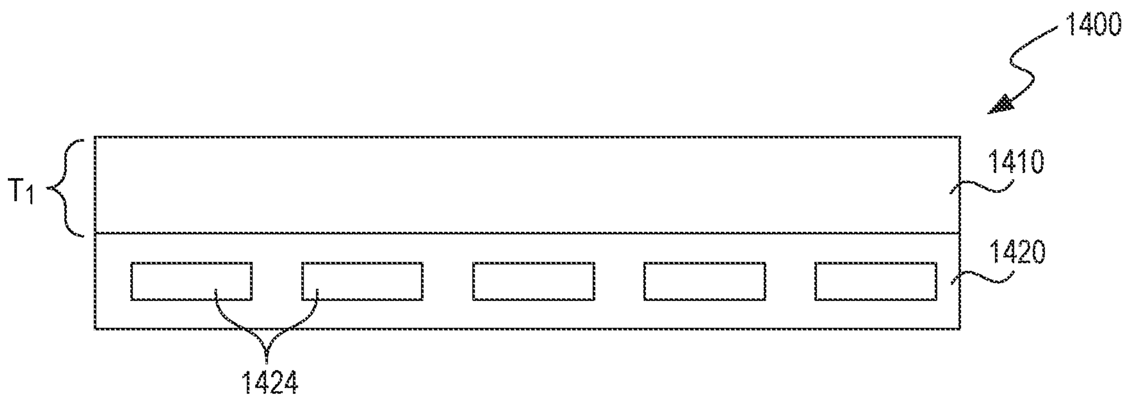
FIGS. 14A-14C are schematic cross-sectional views of a wafer-wafer level process for manufacturing biosensor-related components in accordance with some embodiments of the present technology.
Figure 14B:
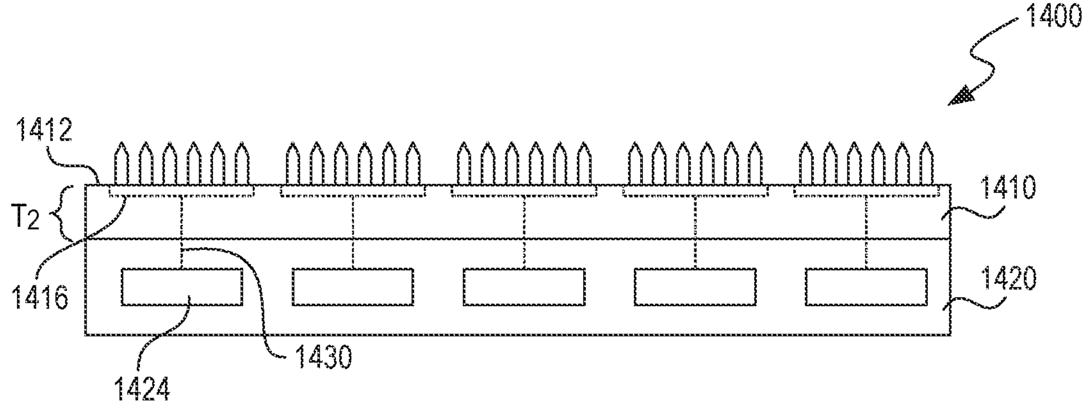
Figure 14C:
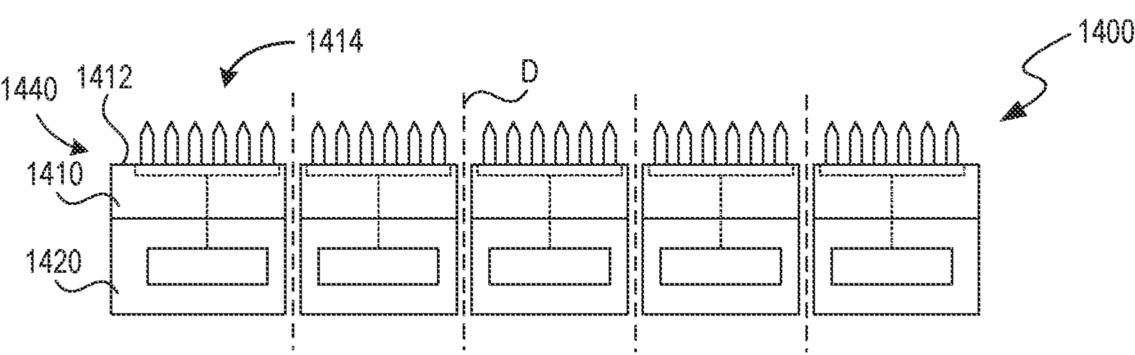

FIGS. 14A-14C are schematic cross-sectional views of a wafer-wafer process 1400 for manufacturing biosensor-related components in accordance with some embodiments of the present technology. In the illustrated embodiments, the wafer-wafer process 1400 is used to manufacture a plurality of arrays of microneedles on a semiconductor substrate. However, it will be understood that the wafer-wafer process 1400 and the benefits therein are limited to the illustrated embodiments. Purely by way of example, the wafer-wafer process 1400 can be used to manufacture and monitor any other component of the device 300 discussed above with reference to FIGS. 3A-3C and device 1300 discussed above with reference to FIGS. 13A-13E.

FIGS. 14A-14B illustrate stages of wafer-wafer processing for manufacturing components for biosensors disclosed herein. FIG. 14A is a schematic cross-sectional view of the wafer-wafer process 1400 after a first wafer 1410 is attached to a second wafer 1420. FIG. 14B is a schematic cross-sectional view of the wafer-wafer process 1400 after an upper surface 1412 of the first wafer 1410 has been etched. FIG. 14C is a schematic cross-sectional view of the wafer-wafer process 1400 after singulation. Referring to FIG. 14A, each of the first and second wafers 1410, 1420 can comprise a semiconductor substrate (e.g., silicon, a printed circuit board (PCB), epoxy, prepreg substrate, and the like). Further, in the illustrated embodiment, the second wafer 1420 includes a plurality of electronic components 1424. The electronic components 1424 can be operable to test any components manufactured on the first wafer 1410, store related information (e.g., a unique identifier for the components, production data, calibration adjustments, and the like), help operate the components once deployed in a biosensor, and/or perform any other suitable action.

FIG. 14B is a schematic cross-sectional view of the wafer-wafer process 1400 after an upper surface 1412 of the first wafer 1410 has been etched to produce a plurality of arrays of microneedles 1414. As a result, a thickness of the first wafer 1410 has been reduced from a first thickness $T_1$ in FIG. 14A to a second thickness $T_2$ in FIG. 14B. In some embodiments, a height of the arrays of microneedles 1414 is generally equal to the reduction (e.g., equal to $T_1-T_2$). Each of the arrays of microneedles 1414 is electrically coupled to a corresponding one of the electronic components 1424 in the second wafer 1420. For example, in the illustrated embodiment, each of the arrays of microneedles 1414 is electrically coupled to an electronic component 1424 via redistribution structure 1416 at the upper surface 1412 of the first wafer 1410 and an interconnect 1430 extending from the redistribution structure 1416 to the electronic component 1424.

Once connected, the electronic components 1424 can send and receive signals back from the arrays of microneedles 1414. For example, the electronic components 1424 can provide an input bias (e.g., an input voltage) and measure a response from the arrays of microneedles 1414 to measure an electro-chemical performance of the arrays of microneedles 1414. In some embodiments, the second wafer 1420 can include an individual electronic component 1424 for each of the arrays of microneedles 1414 on the first wafer 1410, thereby allowing the wafer-wafer process 1400 to directly measure an electro-chemical performance of each of the arrays of microneedles 1414. As a result, the wafer-wafer process 1400 can generate individualized production data for each of the arrays of microneedles 1414 without extrapolating from measurements on one of the arrays of microneedles 1414 to measurements on another.

FIG. 14C is a schematic cross-sectional view of the wafer-wafer process 1400 after the first and second wafers 1410, 1420 are singulated to isolate individual sets 1440 of an array of microneedles 1414 and an electronic component 1424. Each set 1440 schematically represents a completed component from the wafer-wafer process 1400 and can be deployed into a biosensor. For example, each set 1440 can correspond to a completed disposable microsensor patch that can be installed into a biosensor to measure one or more analytes of interest. Once deployed, as discussed above, the electronic component 1424 can communicate the unique identifier, production data, and/or calibration adjustments for the set 1440 to the biosensor and/or a user's electronic device (e.g., a smartphone). Additionally, or alternatively, the electronic component 1424 can be controlled to operate the array of microneedles 1414 to generate signals in response to the analyte(s) of interest.

In some embodiments, the second wafer 1420 is not singulated with the first wafer 1410. For example the wafer-wafer process 1400 can include a lift off process (not shown) before the sets 1440 are singulated. In some such embodiments, the second wafer 1420 (and the electronic components 1424 therein) is reused and attached to a new wafer to directly measure components during manufacturing.

VIII Example Needles for Biosensors

Figure 15A:
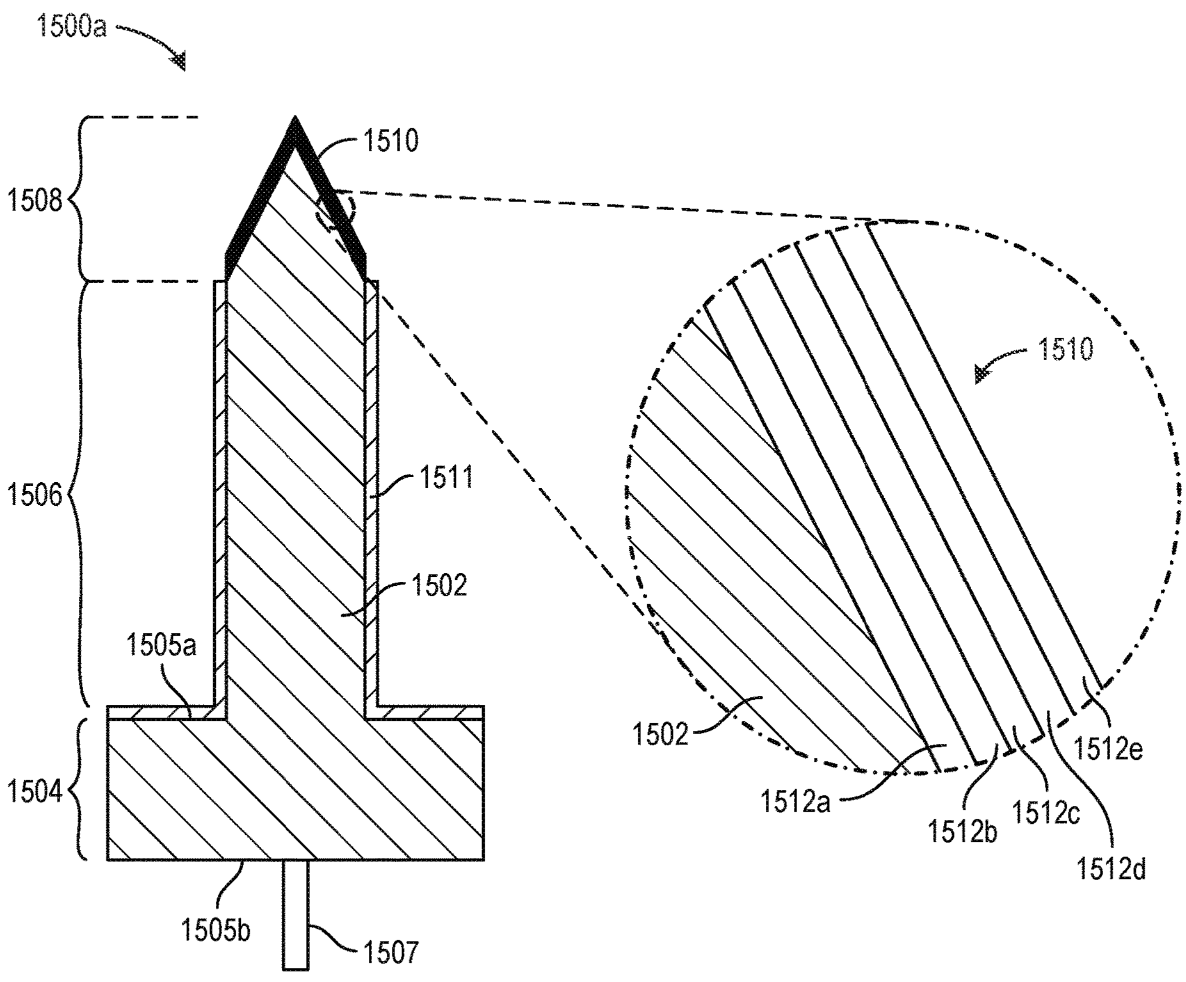
FIGS. 15A-15D are partially schematic illustrations of needles configured in accordance with some embodiments of the present technology.

FIGS. 15A-15D are partially schematic illustrations of microneedles 1500*a-d* configured in accordance with some embodiments of the present technology. Any of the features of the microneedles 1500*a-d* can be incorporated in any embodiment of the biosensors described herein (e.g., the device 300 of FIG. 3, the device 1300 of FIGS. 13A-13E). Referring first to FIG. 15A, the microneedle 1500*a* includes a substrate 1502 having a base 1504, and a needle body 1506 extending from the base 1504. The substrate 1502 can be composed of a semiconducting material (e.g., silicon, quartz, gallium arsenide), a conducting material (e.g., gold, steel, platinum, nickel, silver, polymer, etc.), and/or an insulating or non-conductive material (e.g., glass, ceramic, polymer, prepreg, etc.). In some embodiments, the substrate 1502 can include a combination of materials (e.g., a composite, alloy, etc.). In some embodiments, the substrate 1502 can be an epitaxial wafer, monocrystalline silicon, polysilicon wafer, a doped wafer, an undoped wafer, or the like and include one or more etching features, layers, etc. For example, the substrate 1502 can be a wafer with a diameter (e.g., 200 mm, 300 mm, 400 mm, 450 mm, etc.) selected based on the fabrication process, number of needles arrays per wafer, or the like.

The needle body 1506 can be an elongate protrusion or column connected to a front side 1505*a* of the base 1504. The needle body 1506 can have any suitable cross-sectional shape or profile, such as square, rectangular, triangular, circular, oval, polygonal, non-polygonal, etc. The needle body 1506 can terminate in a tip 1508 configured to penetrate into the skin. As shown in FIG. 15A, the tip 1508 can be a sharpened structure having a multi-faceted (e.g., pyramidal) or other suitable shape (e.g., conical). In some embodiments, the tip 1508 includes a hollow via providing a fluid channel into an interior portion of the needle body 1506. The needle body 1506 and tip 1508 can collectively have a length less than or equal to 500 μm, 475 μm, 450 μm, 425 μm, 400 μm, 350 μm, 300 μm, 250 μm, 200 μm, 150 μm, 100 μm or 50 μm (or any other suitable length).

In some embodiments, the microneedle 1500*a* is a solid, continuous structure that lacks any openings, channels, pores, etc., for transporting fluid into the interior of the substrate 1502. Accordingly, the microneedle 1500*a* can be configured to operate without microfluidics, reagent solutions, and/or other fluid-based analyte detection mechanisms. Instead, the microneedle 1500*a* can detect analytes using one or more material layers on the surface of the substrate 1502, which can reduce the number of components required and simplify sensor manufacturing and operation. The microneedle 1500*a* can include a sensing or active region 1510 configured for analyte detection. In some embodiments, the microneedle 1500*a* includes a central via that provides space for an interstitial fluid to flow into and/or out of the microneedle 1500*a*. In such embodiments, the sensing region 1510 can be within the via and protected from damage when the microneedle is inserted into the user's skin. The sensing region 1510 can generate electrical signals upon detection of one or more target analytes. The signals can be transmitted by the substrate 1502 through the needle body 1506 to the base 1504, and subsequently to a set of electrical contacts 1507 (e.g., a conductive interconnect, bond pad, or other circuitry) connected to a back side 1505*b* of the base 1504. In some embodiments, the body 1506 can include one or more conductive channels and/or structures that help establish conductive paths through the body 1506. Purely by way of example, a peripheral cross section of the body 1506 can be doped with a conductive material to help establish a conductive path therein.

The remaining surfaces of the microneedle 1500*a* can be passivated or otherwise covered by an insulating layer 1511. The insulating layer 1511 can be made of one or more non-conductive materials, such as an insulating polymer (e.g., polyimide, cyanate ester, polyurethane, silicone), an oxide, a carbide, a nitride (e.g., silicon nitride), or a combination thereof. The insulating layer 1511 can be formed using any suitable technique, such as thermal oxidation, chemical vapor deposition, plasma-enhanced chemical vapor deposition, low pressure chemical vapor deposition techniques, dip coating, spray coating, and/or evaporation.

In the illustrated embodiment, the sensing region 1510 is localized to the tip 1508 of the microneedle 1500*a*, and the remaining portions of the microneedle 1500*a* (e.g., the needle body 1506 and/or base 1504) are covered by the insulating layer 1511. Accordingly, analyte detection can occur only at the tip 1508, which can improve sensor performance. For example, this configuration can improve accuracy and/or reduce calibration requirements, since the sensing region 1510 is a well-defined surface area that is completely in contact with the interstitial fluid in the skin. This approach can also reduce the susceptibility of the sensor signal to leakage currents, electrical noise, non-specific electrochemical reactions, and/or noise or contamination from sweat and other surface contaminants. In other embodiments, however, the sensing region 1510 can be located at a different portion of the microneedle 1500*a*, the microneedle 1500*a* can include multiple discrete sensing regions 1510 at different locations, and/or the insulating layer 1511 can be omitted.

The sensing region 1510 can include a plurality of functional layers 1512*a-e* (collectively, "layers 1512"). The layers 1512 can include, for example, a conductive layer 1512*a*, a first barrier layer 1512*b*, a reactive layer 1512*c*, a second barrier layer 1512*d*, and/or a protective layer 1512*e*. The conductive layer 1512*a* can provide a base electrochemical surface or material for facilitating electron transfer to the substrate 1502, thus producing an electrical signal that can be transported by the needle body 1506 to the base 1504, and subsequently to coupled detection circuitry (not shown). For example, the conductive layer 1512*a* can transfer electrons from one or more intermediate electroactive species generated by the other layers 1512 to the underlying substrate 1502. Alternatively, the conductive layer 1512*a* may not transfer electronics, and may instead act as a conductive surface for non-faradaic processes. The conductive layer 1512*a* can include any suitable electrically conductive material, such as platinum, palladium, iridium, tungsten, titanium, gold, silver, nickel, glassy carbon, silicon, doped silicon, or combinations thereof (e.g., a combination of titanium and platinum). In embodiments where multiple conductive materials are used, the materials can be combined into a single layer, can be sequentially deposited as discrete sublayers, or any other suitable configuration. Optionally, the conductive layer 1512*a* (or a portion thereof, such as a titanium sublayer) can also serve as an adhesion layer to enhance mechanical coupling of the sensing region 1510 to the underlying substrate 1502.

The first barrier layer 1512*b* can be a selective transport membrane, diffusion barrier, or similar structure configured to restrict non-target chemical species from reaching the conductive layer 1512*a*. The non-target species can include, for example, species that may foul the conductive layer 1512*a*, generate a false signal from interacting with the conductive layer 1512*a*, or produce any other activity that may interfere with analyte detection. The first barrier layer 1512*b* can be configured to exclude non-target species based on size, charge, phase, hydrophobicity, atomic orbital structure, and/or any other suitable structure. Alternatively or in combination, the first barrier layer 1512*b* can control the rate of transport of species to the conductive layer 1512*a*. In some embodiments, the first barrier layer 1512*b* includes a polymer, such as polytetrafluoroethylene (PTFE), polyethylene glycol (PEG), urethane, polyurethane, cellulose acetate, polyvinyl alcohol (PVA), polyvinyl chloride (PVC), polydimethylsiloxane (PDMS), parylene, polyvinyl butyral (PVB), a sulfonated tetrafluoroethylene, a chlorinated polymer, a fluorinated polymer, or suitable materials known to those of skill in the art or combinations thereof. Optionally, the first barrier layer 1512*b* can include functional compounds such as lipids, charged chemical species, etc., that can provide a barrier against transport of non-target species.

The reactive layer 1512*c* (also referred to herein as a "sensing layer") can include one or more agents (e.g., enzymes, catalysts, conductive polymers, redox mediators, electron transporters, etc.) configured to facilitate a reaction with a target analyte to produce a chemical species that can be detected by the conductive layer 1512*a*, referred to herein as an "intermediate species" or "mediator species." For example, the agent can modify the target analyte to create the intermediate species, or can react with the analyte to produce a product that serves as the intermediate species. The reactive layer 1512*c* can include a single agent (e.g., a single enzyme or catalyst), or can include multiple agents (e.g., two, three, four, five, or more different enzymes or catalysts). The agent can be selected based on the particular analyte or analytes to be detected. For example, the agent can be configured to react and/or interact with any of the analytes described herein, such as glucose, gases (e.g. oxygen, carbon dioxide, etc.), electrolytes (e.g., bicarbonate, potassium, sodium, magnesium, chloride, lactic acid, ascorbic acid), BUN, creatinine, ketones, cholesterol, triglycerides, alcohols, amino acids (e.g., glutamate, choline, tyrosine), neurotransmitters, hormones, disease biomarkers (e.g., cancer biomarkers, cardiovascular disease biomarkers), drugs, or combinations thereof.

The agent can be or include any suitable enzyme or catalyst known to those of skill in the art, such as an oxidoreductase, transferase, hydrolase, lysase, etc. Examples of enzymes or catalysts suitable for use in the reactive layer 1512*c* can include, but are not limited to: glucose oxidase, creatine amidinohydrolase, alcohol oxidase, D- and L-amino acid oxidases, cholesterol oxidase, galactose oxidase, and urate oxidase. The agent can be configured to modify and/or react with a target analyte to produce any suitable intermediate species, such as hydrogen peroxide, ammonia, nicotinamide adenine dinucleotide (NAD), nicotinamide adenine dinucleotide phosphate (NADPH), flavin adenine dinucleotide (FAD), oxygen, or other small molecules. In some embodiments, the agent is embedded in, cross-linked to, and/or otherwise coupled to a matrix or membrane, such as a polymer matrix or membrane. The matrix or membrane can include any of the following: an aziridine-based polymer (e.g., polyethyleneimine), an amine-decorated polymer, polyethylene, PTFE, urethane, polyurethane, phenylenediamine, ortho-phenylenediamine, meta-phenylenediamine, tyramine, a protein matrix, an amino acid matrix, a crosslinker, other electropolymerized components, etc.

The second barrier layer 1512*d* can be a selective transport membrane, diffusion barrier, or similar structure configured to restrict non-target species from reaching the reactive layer 1512*c*. The non-target species can include, for example, species that may foul the reactive layer 1512*c*, generate a false signal from interacting with the reactive layer 1512*c*, or produce any other activity that may interfere with analyte detection. The second barrier layer 1512*d* can be configured to exclude non-target species based on size, charge, phase, hydrophobicity, atomic orbital structure, and/or any other suitable structure. Alternatively or in combination, the second barrier layer 1512*d* can control the rate of transport of species to the reactive layer 1512*c*. The second barrier layer 1512*d* can include any of the materials described above in connection with the first barrier layer 1512*b*.

The protective layer 1512*e* can be configured to protect the lower layers 1512 from damage, such as mechanical damage and/or damage from cells, protein aggregation, biofouling, and/or enzymatic degradation. Alternatively or in combination, the protective layer 1512*e* can improve biocompatibility, e.g., by providing anti-microbial and/or anti-inflammatory properties. The protective layer 1512*e* can be made of any suitable material, such as PTFE, PEG, urethane, polyurethane, cellulose acetate, PVA, PVC, PDMS, parylene, PVB, a sulfonated tetrafluoroethylene, a chlorinated polymer, a fluorinated polymer, or a combination thereof. In some embodiments, the protective layer 1512*e* is localized to the tip 1508 of the microneedle 1500*a*. In other embodiments, the protective layer 1512*e* can extend over other portions of the microneedle 1500*a*, such as over the needle body 1506 and/or the base 1504. In such embodiments, the protective layer 1512*e* can be the outermost layer on the microneedle 1500*a* (e.g., the protective layer 1512*e* is positioned over the insulating layer 1511 and/or any other layers over the insulating layer 1511).

The configuration of the sensing region 1510 can be modified in many different ways. For example, although the illustrated embodiment includes five layers 1512, in other embodiments, the sensing region 1510 can include a different number of layers 1512 (e.g., one, two, three, four, six, seven, eight, nine, ten, or more layers 1512). Any of the layers 1512 can be divided into individual sublayers, or can be combined with each other into a single layer. The ordering of the layers 1512 can also be varied. Additionally, the sensing region 1510 can include additional functional layers not shown in FIG. 15A. In some embodiments, one or more of the layers 1512 are optional and can be omitted. For example, in other embodiments, the second barrier layer 1512*d* can be omitted, such that the sensing region 1510 includes only the conductive layer 1512*a*, first barrier layer 1512*b*, reactive layer 1512*c*, and protective layer 1512*e*.

As another example, the reactive layer 1512*c* and the second barrier layer 1512*d* can be omitted, such that the sensing region 1510 includes only the conductive layer 1512*a*, first barrier layer 1512*b*, and protective layer 1512*e*. This configuration can be used, for example, for amperometric and/or potentiometric detection of analytes. In some embodiments, an amperometric detection scheme is used to detect oxygen, dissolved gases, and/or other small molecules. In such embodiments, the first barrier layer 1512*b* can include one or more polymers, protein aggregates, metals, dielectrics and/or other materials having selective transport properties for the analyte of interest. A potentiometric detection scheme can be used to detect charged species such as ions (e.g., potassium, sodium, magnesium, chloride, metals), pH, and/or larger charged molecules. The first barrier layer 1512*b* can include one or more polymers, protein aggregates, metals, dielectrics and/or other materials having selective transport properties for the charged species. Alternatively or in combination, the first barrier layer 1512*b* can include chelating complexes for creating specificity for a target ion or metal. The complexes can be incorporated into the first barrier layer 1512*b* via any suitable technique, such as entanglement, direct conjugation, hydrogen bonding, ionic interaction, and/or adsorption.

In a further example, the first barrier layer 1512*b* and the reactive layer 1512*c* can be omitted, such that the sensing region 1510 includes the conductive layer 1512*a*, second barrier layer 1512*d*, and protective layer 1512*e*; and a binding layer (not shown) can be added to the sensing region 1510 between the conductive layer 1512*a* and the second barrier layer 1512*d*. This configuration can be used to detect nucleic acids (e.g., DNA or RNA oligomers), proteins, peptides, or other small molecules. Such analytes can be detected based on charge, surface capacitance, blocking transport, a conformational change activating a redox probe, or any other suitable probe.

In such embodiments, the binding layer can include a membrane, matrix, etc., having selective binding, adhesion, adsorption, and/or other interaction properties with the target analyte. This can be achieved, for example, through molecular engineering of the surface properties and/or manipulation of properties such as charge, viscoelastic properties, surface energy, hydrophobicity, surface roughness, topological morphology, or other general properties. Specificity can also be achieved by adding additional molecules, proteins, oligomers, coordination complexes, or polymers that bind specific molecules using a binding site or series of binding sites. Any of these binding and/or adhesion mechanisms may be reversible or irreversible, depending on the use case for the biosensor. The molecular association may change the surface properties of the binding layer above the conductive layer 1512*a* resulting in a detectable change in the molecular microenvironment, including, but not limited to, changes in pH, charge, surface capacitance, hydration, or diffusion and transport properties. Alternatively or in combination, the association may induce specific conformation changes in the either the receptor or the analyte that result in a change of function or property of the either analyte or the complex. These changes can include conformation changes that produce any of the following results: bring a functional group or probe closer or further from the conductive layer 1512*a*, a change in charge, a shifting of the energy level of electrons, and/or molecular orbitals within specific functional groups of either the receptor or analyte. These changes can be detected using stationary or dynamic electrochemical techniques including, but not limited to, cyclic voltammetry, pulsed voltammetry, electrochemical impedance spectroscopy, chronoamperometry, or chronopotentiometry.

Figures 15B, 15C, 15D:
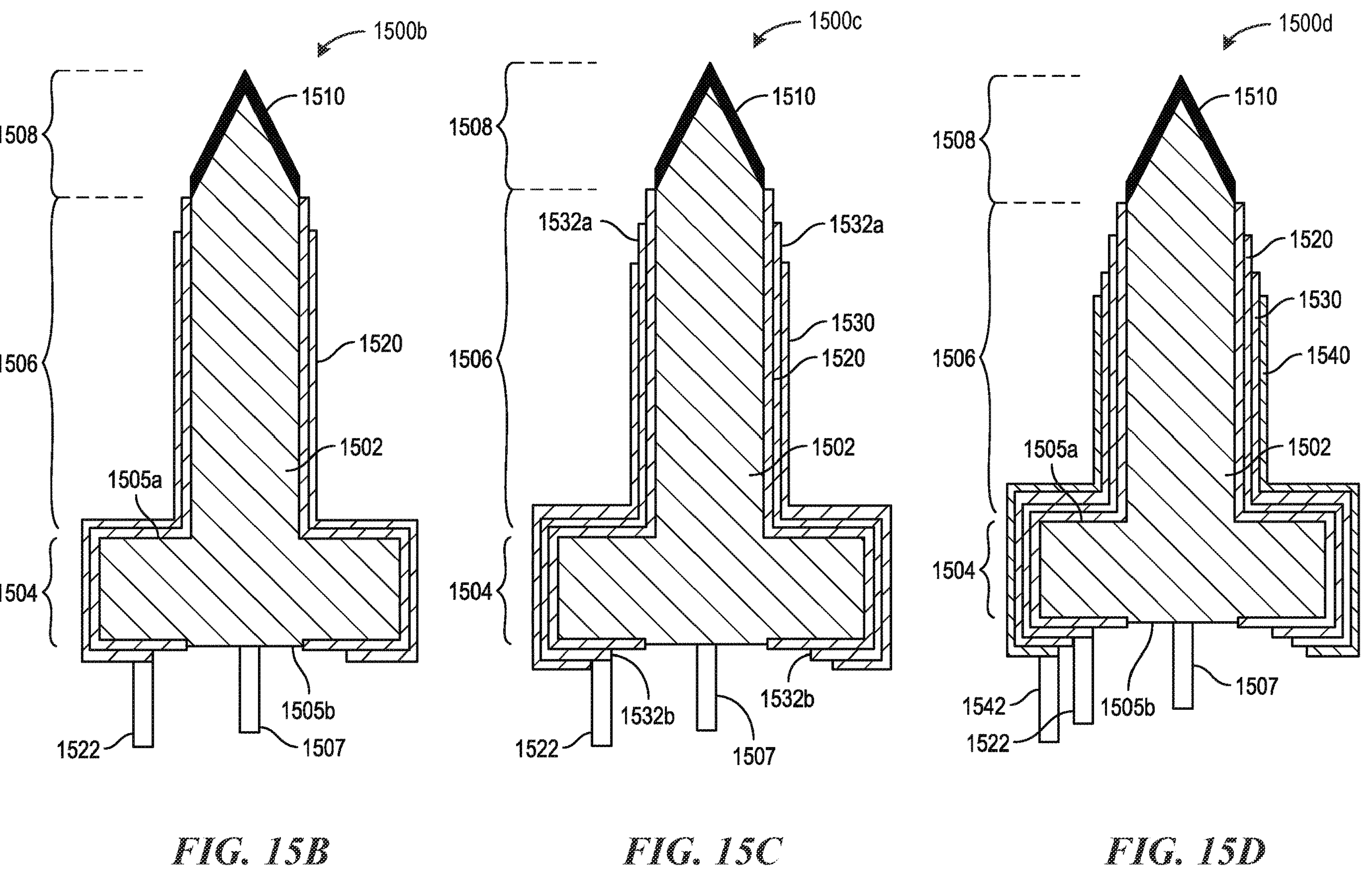

FIGS. 15B-15D illustrate additional examples of microneedles 1500*b-d*. The microneedles 1500*b-d* can be generally similar to the microneedle 1500*a* of FIG. 15A. Accordingly, like numbers indicate identical or similar components, and the discussion of the microneedles 1500*b-d* will be limited to those features that differ from the microneedle 1500*a* of FIG. 15A.

Referring first to FIG. 15B, the microneedle 1500*b* includes a sensing region 1510 localized to the tip 1508 of the microneedle 1500*b*, and an insulating layer 1511 covering the needle body 1506 and base 1504. The microneedle can further include a conductive film 1520, such as an evaporated metal film, or other conductive coating, layer, or material. As shown in FIG. 15B, the conductive film 1520 is located on the insulating layer 1511, and extends over at least a portion of the needle body 1506 and base 1504. The conductive film 1520 can extend around to the back side 1505*b* of the base 1504 for connecting to a set of electrical contacts 1522 located at or near the back side 1505. In such embodiments, the insulating layer 1511 can also extend to the back side 1505*b* to avoid shorting between the conductive film 1520 and the substrate 1502. Alternatively, the conductive film 1520 can terminate at the front side 1505*a* of the base 1504, and can be connected to the electrical contacts 1522 using vias or other connectors extending between the front and back sides 1505*a-b* of the base 1504.

The electrical contacts 1522 for the conductive film 1520 can be electrically isolated from the electrical contacts 1507 for the sensing region 1510 by an insulating material (not shown), thus providing two independent signal pathways. The configuration illustrated in FIG. 15B can be used to support a multi-analyte detection scheme in which the sensing region 1510 serves as a working electrode, while the conductive film 1520 serves as a reference electrode or counter electrode. This approach can eliminate the need for a separate reference electrode or counter electrode microneedle array.

Referring next to FIG. 15C, the microneedle 1500*c* is generally similar to the microneedle 1500*b* of FIG. 15B, except that microneedle 1500*c* includes a second insulating layer 1530 over the conductive film 1520. The second insulating layer 1530 can cover certain regions of the conductive film 1520, while leaving selected regions exposed (e.g., upper regions 1532*a* and/or lower regions 1532*b*). The second insulating layer 1530 can be or include any suitable passivating and/or insulating material, such as an insulating polymer (e.g., polyimide, cyanate ester, polyurethane, silicone), an oxide, a carbide, a nitride (e.g., silicon nitride), or a combination thereof. The configuration shown in FIG. 15C can protect the conductive film 1520, and/or can prevent electrical noise or other conductive paths from interacting with the conductive films 1520 except in the regions 1532*a-b* where the conductive film 1520 is exposed.

Referring next to FIG. 15D, the microneedle 1500*d* is generally similar to the microneedle 1500*c* of FIG. 15C, except that microneedle 1500*d* includes a second conductive film 1540 over the second insulating layer 1530. The second conductive film 1540 can be or include an evaporated metal film, or other conductive coating, layer, or material. The second conductive film 1540 can be located on the second insulating layer 1530, and can extend over at least a portion of the needle body 1506 and base 1504. The second conductive film 1540 can extend around to the back side 1505*b* of the base 1504 for electrical coupling to a set of electrical contacts 1542. Alternatively, the second conductive film 1540 can terminate at the front side 1505*a* of the base 1504, and can be connected to the electrical contacts 1542 using vias or other connectors extending between the front and back sides 1505*a-b* of the base 1504. The electrical contacts 1542 for the second conductive film 1540 can be electrically isolated from the electrical contacts 1507 for the sensing region 1510 and from the electrical contacts 1522 for the conductive film 1520 by an insulating material (not shown), thus providing three independent signal pathways. Optionally, the microneedle 1500*d* can further include a third insulating layer (not shown) over the second conductive film 1540, e.g., to protect the second conductive film 1540 and/or reduce noise, similar to the function of the second insulating layer 1530.

The configuration illustrated in FIG. 15D can be used to support a multi-analyte detection scheme in which sensing region 1510 serves as a working electrode, the conductive film 1520 serves as a reference electrode or counter electrode, and the second conductive film 1540 serves as a second reference electrode or counter electrode. For example, the conductive film 1520 can serve as the reference electrode, and the second conductive film 1540 can serve as the counter electrode. This approach can eliminate the need for separate reference electrode and counter electrode microneedle arrays. Alternatively, one or both of the conductive films 1520, 1540 can be as blank electrodes, such as for tracking drift and/or for generating electrochemical impedance measurements (e.g., to detect changes in the epidermal microenvironment, to detect proper application and/or insertion of the microneedle 1500*d*, etc.). Additionally, one or both of the conductive films 1520, 1540 can be used to detect another analyte (e.g., oxygen or any number of other molecules), e.g., in situations where simultaneous detection would be beneficial for calibration, sensor data fusion, multi-analyte measurements, etc.

Optionally, the configuration of FIG. 15D can be further modified to include additional conductive layers or films interspersed with insulating material (e.g., insulating layers), thus providing even more independent signal pathways in a single microneedle 1500*d*. For example, the microneedle 1500*d* can be modified to include a total of four, five, six, seven, eight, nine, ten, or more independent electrical pathways. Each electrical pathway can be connected to a respective set of electrical contacts. Accordingly, a single microneedle 1500*d* can simultaneously include multiple electrodes or active areas, some or all of which can perform different functions (e.g., serve as detection areas, working electrodes, reference electrodes, counter electrodes, blank electrodes, etc.).

Any of the microneedles described herein (e.g., the microneedles 1500*a-d* of FIGS. 15A-15D) can be incorporated into a microneedle array. An array of microneedles can include any suitable number of microneedles, such as one, two, three, four, five, six, seven, eight, nine, 10, 15, 20, 25, 30, 35, 40, 45, 50, 60, 70, 80, 90, or 100 microneedles. The microneedles can be arranged in any suitable geometry (e.g., square, rectangular, circular, elliptical, etc.). For example, the microneedles can be arranged in a grid, such as a 2×2, 3×3, 4×4, 5×5, 6×6, 7×7, 8×8, 9×9, or 10×10 square grid. The grid can have any suitable spacing or pitch between individual microneedles, such as a spacing of at least 100 μm, 200 μm, 300 μm, 400 μm, 500 μm, 600 μm, 700 μm, 800 μm, 900 μm, or 1000 μm. The dimensions (e.g., width, length, circumference, diameter, etc.) can be selected based on the target penetration depth. For example, the needles 1500*a-d* of FIGS. 15A-15D can be configured for accessing sites within the skin, subcutaneous sites, or other sites and can be part of the biosensor 242 (FIG. 2), devices 300 (FIG. 3A-3C), device 1300 (FIG. 13A-13E), and other devices disclosed herein.

IX. Examples

The present technology is illustrated, for example, according to various aspects described below. Various examples of aspects of the present technology are described as numbered examples (1, 2, 3, etc.) for convenience. These are provided as examples and do not limit the present technology. It is noted that any of the dependent examples can be combined in any suitable manner, and placed into a respective independent example. The other examples can be presented in a similar manner.

1. A method for manufacturing microneedle biosensors to improve an accuracy of measurements performed by the microneedle biosensors, the method comprising:

generating a map of at least a portion of a wafer, the map indicating a plurality of locations corresponding to one or more components of respective ones of the biosensor;

assigning a unique identifier to each of the plurality of locations in the map, wherein the unique identifier is specific to each of the plurality of locations in the map and the wafer;

performing one or more measurements on the one or more components at a selected location from the plurality of locations; and generating, using the one or more measurements, production data for the one or more components at the selected location, wherein the production data tracks a development and/or a performance of the one or more components at the selected location for detecting one or more analytes.

2. The method of example 1, further comprising:

analyzing the production data to determine a performance prediction for the one or more components, wherein the performance prediction is associated with detection of the one or more analytes;

generating one or more calibration adjustments to operating parameters for a resulting biosensor based on the performance prediction to improve analyte detection accuracy of the resultant biosensor; and linking, using the linking of the production data to the one or more components, the one or more calibration adjustments to the one or more components at the selected location via the unique identifier.

3. The method of any of examples 1 and 2 wherein each of the locations corresponds to a disposable microsensor having one or more arrays of microneedles, and wherein the one or more calibration adjustments includes at least one of a modification to an input bias for the disposable microsensor or a filter for signals resulting from the disposable microsensor.

4. The method of any of examples 1-3, further comprising linking the production data to the one or more components at the selected location via the unique identifier.

5. The method of any of examples 1-4, further comprising:

generating, using the production data for the one or more components at the selected location, production data for one or more components at a second location in the plurality of locations; and linking the production data to the one or more components at the second location via the unique identifier for the second location.

6. The method of example 5, wherein generating the production data for one or more components at a second location includes:

training a computer model using production data for complete wafers, the computer model relating production data for developing components at a first position to production data for developing components at a second relative position;

determining a first relative position of the selected location and a second relative position of the second location; and applying the computer model the production data for the one or more components at the selected location.

7. The method of any of examples 1-6, further comprising, after completing a first stage of manufacturing of the microneedle biosensors and before completing a second stage of manufacturing of the biosensors:

retrieving the production data linked to the one or more components at the selected location;

determining whether the production data meets an expected metric for the one or more components after the first stage of manufacturing; and in response to the production data not meeting the expected metric, determining an adjustment for the second stage of manufacturing, performing the second stage of manufacturing with the adjustment, and in response to the production data meeting the expected metric, performing the second stage of manufacturing.

8. The method of example 7 wherein the wafer has a first classification indicating a first function for each of the one or more components in each of the plurality of locations, and wherein the adjustment includes:

determining a second classification indicating a second function for each of the one or more components different from the first function, and wherein the second function has an alternative expected metric after the first stage of manufacturing.

9. The method of any of examples 7 and 8 wherein determining the adjustment to the further manufacturing processes includes:

identifying, based on the production data, a shortcoming in development from the first stage of manufacturing; and identifying an additional manufacturing stage to address the shortcoming.

10. The method of example 9 wherein the shortcoming includes at least one of an underdeveloped structure in the one or more components, an overdeveloped structure in the one or more components, an electrical short in at least one of the one or more components, or a thermal short in at least one of the one or more components.

11. The method of any of examples 1-10, further comprising:

receiving operational data indicating a performance of the one or more components in the selected location within an operating biosensor;

identifying one or more components at a second location of the plurality of locations related to the selected location via the unique identifier for each of the selected location and the second location;

generating one or more updates to the production data for one or more components at the second location using the operational data for the one or more components in the selected location; and linking the one or more updates to the production data for one or more components at the second location via the unique identifier for the second location.

12. The method of any of examples 1-11, further comprising:

receiving operational data indicating a performance of the one or more components in the selected location within an operating biosensor;

determining an unacceptable performance of the one or more components using the operational data, the unacceptable performance indicating a recall for the one or more components at a second location of the plurality of locations related to the selected location;

generating a recall notification for the one or more components at the second location; and linking the recall notification to the one or more components at the second location via the unique identifier for the second location.

13. The method of any of examples 1-12 wherein the one or more measurements are first measurements performed after a first stage of manufacturing, and wherein the method further comprises:

performing a second stage of manufacturing;

performing second measurements on the one or more components at the selected location;

generating, using the second measurements, updates to the production data for the one or more components at the selected location; and updating the production data linked to the one or more components at the selected location via the unique identifier.

14. The method of any of examples 1-13 wherein the manufacturing includes a layer-by-layer deposition process to construct a microsensor for a biosensor, and wherein the microsensor includes an electrode comprising a plurality of microneedles configured to access interstitial fluid in a user's skin and generate one or more signals in response to analytes in the interstitial fluid.

15. The method of example 14 wherein the production data tracks at least one of an overall height of the plurality of microneedles, an average height of the plurality of microneedles; a conductivity of the plurality of microneedles, a sensitivity conductivity of the plurality of microneedles, and an electrical performance of the microsensor.

16. The method of any of examples 14 and 15 wherein the one or more measurements are performed after deposition of each layer.

17. The method of any of examples 1-16 wherein the one or more measurements are first measurements performed after a first stage of manufacturing, and wherein the method further comprises:

generating an analysis of a health of a manufacturing tool using the production data; and predicting, using the analysis of the health of the manufacturing tool, a time before needed maintenance for the manufacturing tool.

18. The method of example 17 wherein the manufacturing tool is a first manufacturing tool, and wherein the method further comprises, if the predicted time before the needed maintenance is below a predetermined threshold, performing a second stage of manufacturing on a second manufacturing tool.

19. The method of example 17, further comprising using the predicted time before the needed maintenance to identify a time to perform maintenance on the manufacturing tool ahead of the predicted time.

20. A method for improving an accuracy of a measurement performed a biosensor, the method comprising:

receiving, from a microsensor of the biosensor, at least one unique identifier associated with manufacturing of the microsensor;

retrieving, using the unique identifier, one or more calibration adjustments associated with the microsensor, the one or more calibration adjustments accounting for differences in operation of the microsensor and other microsensors based on production data for the microsensor; and adjusting one or more operational parameters of the biosensor based on the one or more calibration adjustments.

21. The method of example 20, further comprising sending the one or more adjusted operational parameters for the biosensor, wherein the biosensor is configured to receive and use the one or more adjusted operational parameters to detect one or more analytes.

22. The method of any of examples 20 and 21, further comprising sending, from the biosensor, the at least one unique identifier in response to initialization of the microsensor.

23. The method of any of examples 20-22, wherein the operational parameters include at least one of a magnitude of an input voltage supplied to the microsensor patch, a waveform of the input voltage supplied to the microsensor patch, a frequency of the input voltage supplied to the microsensor patch, a biasing force applied to an upper surface of the microsensor patch to ensure the microsensor patch adequately accesses interstitial fluid in a user's skin, or a filter applied to a signal received from the microsensor patch in response to a sensed analyte.

24. The method of any of examples 20-23 wherein the one or more calibration adjustments are retrieved from a network database.

25. The method of any of examples 20-24 wherein the one or more calibration adjustments are retrieved from a memory device on the microsensor.

26. The method of any of examples 20-25 wherein the calibration adjustments include one or more notifications related to the microsensor.

27. The method of any of 20-26 wherein the one or more notifications include at least one of a recall notification for the microsensor patch, an indication of one or more analytes the microsensor patch is not configured to accurately sense, or a warning about possible malfunctions of the microsensor patch.

28. The method of any of examples 20-27 wherein the one or more calibration adjustments further account for observed performance of other microsensor patches manufactured in conjunction with the microsensor patch associated with the unique identifier.

29. The method of any of examples 20-28 wherein the one or more calibration adjustments are specific to each component of a microsensor patch manufactured on a wafer.

30. The method of any of examples 20-29 wherein the one or more calibration adjustments are related to measurements of one or more representative components a wafer on which the microsensor patch was manufactured on.

31. The method of any of examples 20-30 wherein the unique identifier is received through wireless communication with the biosensor when the microsensor patch is installed into the biosensor.

32. The method of any of examples 20-29 wherein the unique identifier is indicated by a physical identifier on the microsensor patch and/or a packaging of the microsensor patch.

33. The method of any of examples 20-31 wherein the unique identifier is stored in a memory device in the microsensor patch.

34. The method of any of examples 20-34, further comprising receiving operational feedback, from a user, related to a performance of the microsensor patch.

35. The method of example 34, further comprising sending the operational feedback to a central database to update calibration adjustments related to one or more other microsensor patches associated to the microsensor patch via the unique identifier.

36. A method for manufacturing microneedle array biosensors, the method comprising:

forming a plurality of microneedles in a semiconductor substrate;

generating production data of one or more of the microneedles;

determining analyte detection information for the one or more microneedles based on the production data, wherein the analyte detection information is indicative of performance of the one or more microneedles when the one or more microneedles are positioned in a user's skin to detect one or more analytes in interstitial fluid in the user's skin; and determining a biosensor calibration routine based on the analyte detection information to increase detection accuracy of the one or more analytes by a microneedle array biosensor with the one or more microneedles.

37. The method of example 36, further comprising:

analyzing the production data to identify one or more performance characteristics of the one or more microneedles;

correlating the identified one or more performance characteristics to at least one candidate calibration; and using the at least one candidate calibration to generate at least a portion of the biosensor calibration routine.

38. The method of any of examples 36 and 37, wherein the production data includes multianalyte-related fabrication data, and the biosensor calibration routine is configured to calibrate the biosensor to increase accuracy of detection of multiple analytes detectable by the plurality of microneedles.

39. The method of any of examples 36-38, further comprising:

retrieving substrate-to-substrate variance data for the substrate; and determining the analyte detection information based on the retrieved substrate-to-substrate variance data.

40. The method of example 39, further comprising:

retrieving a substrate-to-substrate calibration routine based on a substrate order of the substrate; and determining the biosensor calibration routine based on the substrate-to-substrate calibration routine.

41. The method of any of examples 36-40, further comprising:

obtaining wafer-level production data; and determining the biosensor calibration routine based on the wafer-level production data.

42. The method of any of examples 36-41, wherein the biosensor calibration routine includes:

a first calibration algorithm used with a first group of the microneedles that are configured to detect a first analyte; and a second calibration algorithm used with a second group of the microneedles that are configured to detect a second analyte different from the first analyte.

43. The method of any of examples 36-42, further comprising performing at least one electro-chemical test, electrical test, or optical measurement of the microneedles.

44. The method of example 43, further comprising assessing the plurality of microneedles to determine known good microneedles and any known bad microneedles, wherein the assessing includes at least one of testing performance of the microneedles or performing one or more measurements of the microneedles.

45. The method of example 44, wherein the biosensor calibration routine is configured to eliminate usage of the known bad microneedles.

46. The method of example 41, further comprising determining a needle compensation routine for processing detection signals from the array to compensate for the known bad microneedles.

46. The method of example 41, wherein the performance of the one or more microneedles includes one or more of detection accuracy, detection sensitivity, and/or detection life.

47. The method of example 41, further comprising:

determining a threshold detection accuracy value; and increasing detection accuracy of the one or more analytes by the microneedle array biosensor with the one or more microneedles to meet the threshold detection accuracy value.

48. A method comprising:

manufacturing biosensors with at least one tissue-penetrating element configured to detect one or more analytes in body fluids;

generating biosensor production data associated with the manufacturing of the biosensors;

receiving performance data, from users, related to analyte detection by the biosensors;

analyzing the received performance data to determine one or more correlations between an analyte detection by the biosensors and the production data, wherein the one or more correlations identify a set of the production data causally related to the performance data, and wherein the one or more correlations are based at least partially on measurable parameters associated with the biosensors;

generating a biosensor inspection routine based on the set of the production data.

49. The method of example 48, wherein the production data includes one or more physical measurements of biosensors, one or more electrical measurements of biosensors, one or more chemical measurements of biosensors, manufacturing parameters, and/or combinations thereof.

50. The method of any of examples 48 and 49, wherein the at least one tissue-penetrating element includes one or more microneedles, subcutaneous needles, and/or tissue-penetrating electrodes.

51. The method of any of examples 48-50, further comprising determining a prediction of a performance for the at least one tissue-penetrating element based on the biosensor production data when one of the biosensors is positioned on a user's skin to detect the one or more analytes in interstitial fluid in the user's skin, wherein the one or more correlations are based at least partially on a comparison between the performance data and the prediction of the performance.

52. The method of any of examples 48-51, further comprising determining a biosensor calibration routine based on the one or more correlations and the production data to increase a detection accuracy of the biosensors for the one or more analytes.

53. The method of any of examples 48-52, further comprising:

analyzing the production data to identify one or more performance characteristics of the at least one tissue-penetrating element;

correlating the identified one or more performance characteristics to at least one calibration factor; and using the at least one candidate factor to generate at least a portion of the biosensor calibration routine for the biosensors.

54. The method of any of examples 48-53, wherein the production data includes multianalyte-related fabrication data, and the biosensor inspection routine is configured to obtain metrics used to calibrate the biosensors to increase an accuracy of detection of a plurality of analytes detectable by the at least one tissue-penetrating element.

55. The method of any of examples 48-54, further comprising training one or more machine-learning models with reference performance data and the production data, wherein the one or more machine-learning models are configured to generate at least one of the biosensor inspection routine, a biosensor calibration routine, or one or more steps for manufacturing a biosensor.

X. Conclusion

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any material incorporated herein by reference conflicts with the present disclosure, the present disclosure controls. Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Furthermore, as used herein, the phrase "and/or" as in "A and/or B" refers to A alone, B alone, and both A and B. Additionally, the terms "comprising," "including," "having," and "with" are used throughout to mean including at least the recited feature(s) such that any greater number of the same features and/or additional types of other features are not precluded. Further, the terms "approximately" and "about" are used herein to mean within at least within 10 percent of a given value or limit. Purely by way of example, an approximate ratio means within a ten percent of the given ratio.

From the foregoing, it will also be appreciated that various modifications may be made without deviating from the disclosure or the technology. For example, one of ordinary skill in the art will understand that various components of the technology can be further divided into subcomponents, or that various components and functions of the technology may be combined and integrated. In addition, certain aspects of the technology described in the context of particular embodiments may also be combined or eliminated in other embodiments. Furthermore, although advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for manufacturing microneedle biosensors to improve an accuracy of measurements, the method comprising:
- generating a map of at least a portion of a wafer, the map indicating a plurality of locations corresponding to one or more components of respective ones of the microneedle biosensors;
- assigning a unique identifier to each of the plurality of locations in the map, wherein the unique identifier is specific to each of the plurality of locations in the map and the wafer;
- performing one or more measurements on the one or more components at a selected location from the plurality of locations; and
- generating, using the one or more measurements, a production data for the one or more components at the selected location, wherein the production data tracks a development and/or a performance of the one or more components at the selected location for detecting one or more analytes.

2. The method of claim 1, further comprising:
- analyzing the production data to determine a performance prediction for the one or more components, wherein the performance prediction is associated with detection of the one or more analytes;
- generating one or more calibration adjustments to operating parameters for a resulting microneedle biosensor based on the performance prediction to improve analyte detection accuracy of the resultant microneedle biosensor; and
- linking, using the linking of the production data to the one or more components, the one or more calibration adjustments to the one or more components at the selected location via the unique identifier.

3. The method of claim 1 wherein each of the locations corresponds to a disposable microsensor having one or more arrays of microneedles, and further comprising generating one or more calibration adjustments that include at least one of a modification to an input bias for the disposable microsensor or a filter for signals resulting from the disposable microsensor.

4. The method of claim 1, further comprising linking the production data to the one or more components at the selected location via the unique identifier.

5. The method of claim 1, further comprising:
- generating, using the production data for the one or more components at the selected location, a production data for one or more components at a second location in the plurality of locations; and
- linking the production data to the one or more components at the second location via the unique identifier for the second location.

6. The method of claim 5, wherein generating the production data for one or more components at the second location includes:
- training a computer model using the production data for complete wafers, the computer model relating the production data for developing components at a first position to production data for developing components at a second relative position;
- determining a first relative position of the selected location and the second relative position of the second location; and
- applying the computer model the production data for the one or more components at the selected location.

7. The method of claim 1, further comprising,
- after completing a first stage of manufacturing of the microneedle biosensors and before completing a second stage of manufacturing of the microneedle biosensors:
  - retrieving the production data linked to the one or more components at the selected location;
  - determining whether the production data meets an expected metric for the one or more components after the first stage of manufacturing; and
  - in response to the production data not meeting the expected metric, determining an adjustment for the second stage of manufacturing, performing the second stage of manufacturing with the adjustment, and
- in response to the production data meeting the expected metric, performing the second stage of manufacturing.

8. The method of claim 7 wherein the wafer has a first classification indicating a first function for each of the one or more components in each of the plurality of locations, and wherein the adjustment includes:

determining a second classification indicating a second function for each of the one or more components different from the first function, and wherein the second function has an alternative expected metric after the first stage of manufacturing.

9. The method of claim 7 wherein determining the adjustment to the further manufacturing processes includes:

identifying, based on the production data, a shortcoming in development from the first stage of manufacturing; and identifying an additional manufacturing stage to address the shortcoming.

10. The method of claim 9 wherein the shortcoming includes at least one of an underdeveloped structure in the one or more components, an overdeveloped structure in the one or more components, an electrical short in at least one of the one or more components, or a thermal short in at least one of the one or more components.

11. The method of claim 1, further comprising:

receiving an operational data indicating a performance of the one or more components in the selected location within an operating microneedle biosensors;

identifying one or more components at a second location of the plurality of locations related to the selected location via the unique identifier for each of the selected location and the second location;

generating one or more updates to the production data for the one or more components at the second location using the operational data for the one or more components in the selected location; and linking the one or more updates to the production data for the one or more components at the second location via the unique identifier for the second location.

12. The method of claim 1, further comprising:

receiving operational data indicating a performance of the one or more components in the selected location within an operating microneedle biosensors;

determining an unacceptable performance of the one or more components using the operational data, the unacceptable performance indicating a recall for the one or more components at a second location of the plurality of locations related to the selected location;

generating a recall notification for the one or more components at the second location; and linking the recall notification to the one or more components at the second location via the unique identifier for the second location.

13. The method of claim 1 wherein the one or more measurements are first measurements performed after a first stage of manufacturing, and wherein the method further comprises:

performing a second stage of manufacturing;

performing second measurements on the one or more components at the selected location;

generating, using the second measurements, updates to the production data for the one or more components at the selected location; and updating the production data linked to the one or more components at the selected location via the unique identifier.

14. The method of claim 1 wherein the manufacturing includes a layer-by-layer deposition process to construct a microsensor for the microneedle biosensor, and wherein the microsensor includes an electrode comprising a plurality of microneedles configured to access interstitial fluid in a user's skin and generate one or more signals in response to analytes in the interstitial fluid.

15. The method of claim 14 wherein the production data tracks at least one of an overall height of the plurality of microneedles, an average height of the plurality of microneedles; a conductivity of the plurality of microneedles, a sensitivity conductivity of the plurality of microneedles, and an electrical performance of the microsensor.

16. The method of claim 14 wherein the one or more measurements are performed after deposition of each layer.

17. The method of claim 1 wherein the one or more measurements are first measurements performed after a first stage of manufacturing, and wherein the method further comprises:

generating an analysis of a health of a manufacturing tool using the production data; and predicting, using the analysis of the health of the manufacturing tool, a time before needed maintenance for the manufacturing tool.

18. The method of claim 17 wherein the manufacturing tool is a first manufacturing tool, and wherein the method further comprises, if the predicted time before the needed maintenance is below a predetermined threshold, performing a second stage of manufacturing on a second manufacturing tool.

19. The method of claim 17, further comprising using the predicted time before the needed maintenance to identify a time to perform maintenance on the manufacturing tool ahead of the predicted time.

20. The method of claim 1 wherein each of the locations includes an array of microneedles configured to detect one or more analytes of interest, and wherein at least one of the one or more measurements is performed on only a sub-array of the array of microneedles at the selected location.

21. The method of claim 20 wherein the wafer is a first wafer, and wherein the method further includes:

attaching the first wafer to a second wafer having a plurality of electronic components corresponding to the plurality of locations in the map of the first wafer, wherein at least one of the one or more measurements is taken by the plurality of electronic components of the second wafer.

* * * * *